(12) United States Patent
Billen et al.

(10) Patent No.: US 7,514,464 B2
(45) Date of Patent: *Apr. 7, 2009

(54) SUBSTITUTED ARYLPYRAZOLES

(75) Inventors: Denis Billen, Sandwich (GB); Nathan Anthony Logan Chubb, Sandwich (GB); David Morris Gethin, Sandwich (GB); Kim Thomas Hall, Sandwich (GB); Lee Richard Roberts, Sandwich (GB); Nigel Derek Arthur Walshe, Sandwich (GB)

(73) Assignee: Pfizer Limited, Sandwich, Kent (GB)

( * ) Notice: Subject to any disclaimer, the term of this patent is extended or adjusted under 35 U.S.C. 154(b) by 334 days.

This patent is subject to a terminal disclaimer.

(21) Appl. No.: 11/153,103

(22) Filed: Jun. 15, 2005

(65) Prior Publication Data
US 2006/0014802 A1    Jan. 19, 2006

Related U.S. Application Data

(63) Continuation-in-part of application No. 11/013,176, filed on Dec. 15, 2004.

(60) Provisional application No. 60/571,337, filed on May 13, 2004.

(30) Foreign Application Priority Data
Dec. 8, 2003    (GB) ................. 0329314.9

(51) Int. Cl.
  *A61K 31/4439*    (2006.01)
  *C07D 231/10*    (2006.01)
(52) U.S. Cl. .................... 514/406; 548/377.1
(58) Field of Classification Search ............. 514/406; 548/377.1
See application file for complete search history.

(56) References Cited

U.S. PATENT DOCUMENTS

| 5,232,940 | A | 8/1993 | Hatton et al. | 514/406 |
| 5,547,974 | A | 8/1996 | Hatton et al. | 514/407 |

FOREIGN PATENT DOCUMENTS

| EP | 0050335 | 10/1981 |
| EP | 0249409 | 12/1987 |
| EP | 0280991 | 2/1988 |
| EP | 0295227 | 5/1988 |
| EP | 0295117 | 6/1988 |
| EP | 0295118 | 12/1988 |
| EP | 0273862 | 7/1991 |
| EP | 0579280 | 1/1994 |
| EP | 0234119 | 8/1994 |
| EP | 0780378 | 6/1997 |
| EP | 0933363 | 8/1999 |
| EP | 0957094 | 11/1999 |
| GB | 1586258 | 3/1981 |
| GB | 2085302 | 4/1982 |
| WO | WO93/06089 | 4/1993 |
| WO | WO94/16732 | 8/1994 |
| WO | WO95/24219 | 9/1995 |
| WO | WO97/07102 | 2/1997 |
| WO | WO97/07202 | 2/1997 |
| WO | WO97/11602 | 4/1997 |
| WO | WO97/12521 | 4/1997 |
| WO | WO97/36483 | 10/1997 |
| WO | WO97/36484 | 10/1997 |
| WO | WO97/36485 | 10/1997 |
| WO | WO97/36486 | 10/1997 |
| WO | WO98/24767 | 6/1998 |

OTHER PUBLICATIONS

Elkaschef et al., *Chemical Abstracts*, vol. 81, No. 1520695, 1974.

*Primary Examiner*—Kamal A Saeed
(74) *Attorney, Agent, or Firm*—Lucy X. Yang; Paul M. Misiak

(57) ABSTRACT

This invention relates to a combination product comprising a compound of formula I (I)

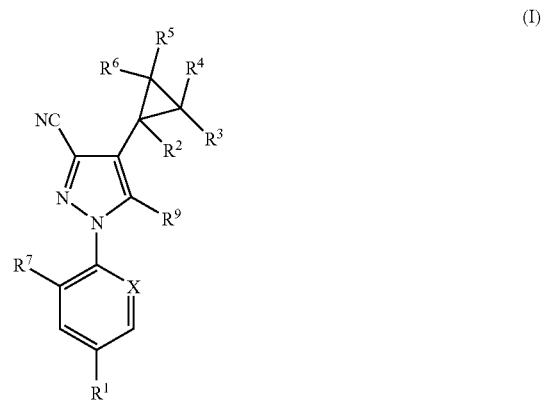

wherein X, $R^1$, $R^2$, $R^3$, $R^4$, $R^5$, $R^6$, $R^7$ and $R^9$ are as described herein, and one or more further biologically active compounds as described herein, particularly anti-parasitic agents.

16 Claims, No Drawings

SUBSTITUTED ARYLPYRAZOLES

CROSS-REFERENCE TO RELATED APPLICATIONS

This application is a Continuation-in-Part of application Ser. No. 11/013,176, filed on Dec. 15, 2004, now pending, which claims the benefit of U.S. provisional application Ser. No. 60/571,337, filed May 13, 2004, and claims the benefit of United Kingdom Application No. 0329314.9, filed Dec. 18, 2003, which are incorporated herein by reference.

FIELD OF THE INVENTION

This invention relates to a combination product comprising a pyrazole derivative of formula (I) in combination with one or more biologically active compounds as described herein, particularly anti-parasitic agents. The compounds of interest of formula (I) are cyclopropylarylpyrazoles and, more particularly, the invention relates to 1-aryl-4-cyclopropylpyrazoles in which there is at least one fluorine attached to the cyclopropyl ring.

International Patent Application Publication No. (WO) 9824767, European Patent Application Publication No. (EP) 933363 and EP957094 describe 4-cyclopropyl arypyrazoles having parasiticidal activity for the control of arthropods.

The prior art compounds do not always demonstrate good activity or a long duration of action against parasites. Similarly, some parasiticidal agents are useful only for a narrow spectrum of parasites. It is an aim of the present invention to overcome various disadvantages of or improve on the properties of prior art compounds. Thus it is an aim of the invention to provide an arylpyrazole which has improved activity relative to prior art compounds against parasites. The compounds of the present invention have especially good ability to control a broad spectrum of arthropods as shown by the results of tests demonstrating their potency and efficacy. In particular, the compounds of the present invention are significantly more active against fleas than similar prior art compounds.

It is a further aim to provide compounds with a long duration of action. Most preferably, the compounds control infestation by arthropods for a period of at least twenty-eight days. The extended duration of action is generally attributed to an extended half life of the compound in vivo in the host mammal.

It is also desirable that the compounds of the present invention should have an improved pharmacokinetic profile, improved safety, improved persistence and improved solubility.

Thus, according to the present invention, there is provided a compound of formula (I):

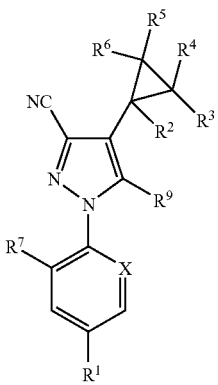

(I)

wherein:
$R^1$ is $CF_3$, $OCF_2H$, $OCF_3$, —$SCF_3$, —$SOCF_3$, —$SO_2CF_3$, or $SF_5$;
$R^2$ is H, fluoro, or $C_{1-4}$ alkyl optionally substituted by 1 to 5 halogen atoms independently selected from chloro and fluoro;
$R^3$, $R^4$, $R^5$, and $R^6$ independently represent H, $C_{1-4}$ alkyl optionally substituted by 1 to 5 halogen groups independently selected from chloro and fluoro, or a chloro or fluoro;
$R^7$ is Cl or fluoro;
X is $CR^8$ or N where $R^8$ is Cl or fluoro; and
$R^9$ is $NR^aR^b$;
$R^a$ is selected from hydrogen, $C_{1-6}$ alkyl, $C_{2-6}$ alkenyl, $C_{3-8}$ cycloalkyl, $C(O)OC_{1-6}$ alkyl and $C_{1-6}$ alkanoyl, wherein each of the above groups may include one or more optional substituents where chemically possible independently selected from halo, het, phenyl, hydroxy, —C(O)OH, —C(O)O $C_{1-6}$ alkyl, $C_{1-6}$ alkyl, $C_{1-6}$ haloalkyl, $C_{3-8}$ cycloalkyl, $C_{1-6}$ alkoxy, $C_{1-6}$ haloalkoxy, amino, $C_{1-6}$ alkyl amino and di $C_{1-6}$ alkyl amino;
$R^b$ is selected from hydrogen, $C_{1-6}$ alkyl, $C_{2-6}$ alkenyl, $C_{1-6}$ alkanoyl and $C(O)OC_{1-6}$ alkyl, wherein each of the above groups may include one or more optional substituents where chemically possible independently selected from, halo, phenyl, hydroxy, —COOH, —C(O)O $C_{1-6}$ alkyl, $C_{1-6}$ alkyl, $C_{1-6}$ haloalkyl, $C_{3-8}$ cycloalkyl, $C_{1-6}$ alkoxy, $C_{1-6}$ haloalkoxy, amino, $C_{1-6}$ alkyl amino and di $C_{1-6}$ alkyl amino;
or $R^a$ and $R^b$ together with the N atom to which they are attached may form a three to seven-membered heterocyclic ring containing one or more further N, O or S atoms and wherein said heterocyclic ring may bear one or more optional substituents selected from oxo, halo, het, phenyl, hydroxy, —COOH, —C(O)O $C_{1-6}$ alkyl, $C_{1-6}$ alkyl, $C_{1-6}$ haloalkyl, $C_{3-8}$ cycloalkyl, $C_{1-6}$ alkoxy, $C_{1-6}$ haloalkoxy, amino, $C_{1-6}$ alkyl amino and di $C_{1-6}$ alkyl amino; and
het represents a four- to seven-membered heterocyclic group, which is aromatic or non-aromatic and which contains one or more heteroatoms selected from nitrogen, oxygen, sulfur and mixtures thereof, and wherein said heterocyclic ring is optionally substituted, where the valence allows, with one or more substituents selected from halo, cyano, nitro, $C_{1-6}$ alkyl, $C_{1-6}$ haloalkyl, $C_{1-6}$ alkoxy, $OC(O)C_{1-6}$ alkyl, $C(O)C_{1-6}$ alkyl, $C(O)OC_{1-6}$ alkyl and $NR^cR^d$, where $R^c$ and $R^d$ are independently selected from hydrogen, $C_{1-6}$ alkyl and $C_{2-6}$ alkenyl, wherein each of the above groups may include one or more optional substituents where chemically possible independently selected from halo, phenyl, hydroxy, —COOH, $C(O)OC_{1-6}$ alkyl, $C_{1-6}$ alkyl, $C_{1-6}$ haloalkyl, $C_{3-8}$ cycloalkyl, $C_{1-6}$ alkoxy, $C_{1-6}$ haloalkoxy, amino, $C_{1-6}$ alkyl amino and di $C_{1-6}$ alkyl amino; or a pharmaceurtically acceptable salt or prodrug thereof;

with the proviso that at least one of $R^2$, $R^3$, $R^4$, $R^5$, or $R^6$ is fluoro.

In the compounds of formula (I) within the scope of this invention, the variables of said formula (I) (ie, $R^1$, $R^2$, $R^3$, $R^4$, $R^5$, $R^6$, $R^7$, $R^8$, $R^9$, $R^a$, $R^b$, and X) may have any definition provided herein for that specific variable. Formula I and Formula (I) are used interchangeably.

In the compounds according to formula (I), $C_{1-6}$ haloalky or $C_{1-6}$ haloalkoxy means a $C_{1-6}$ halky or $C_{1-6}$ alkoxy substituted by 1 to 5 chloro or fluoro groups chosen independently. Also, 'halo' means a group selected from fluoro, bromo, chloro, bromo or iodo.

Suitably, $R^1$ is $CF_3$ or $SF_5$, preferably $CF_3$.

Suitably $R^2$ is $CF_3$ or $CHF_2$, preferably $CF_3$. In an alternative suitable embodiment, $R^2$ is fluoro.

Suitably, $R^3$, $R^4$, $R^5$ and $R^6$ independently represent H or fluoro.

Preferably, $R^2$ is $CF_3$ and $R^3$, $R^4$, $R^5$ and $R^6$ independently represent 2, 3 or 4 fluoro groups, more preferably 2 fluoro groups, most preferably on $R^3$ and $R^4$ and $R^5$ and $R^6$ represent H.

Similarly preferably, $R^2$ is $CHF_2$ and $R^3$, $R^4$, $R^5$, and $R^6$ independently represent 2, 3 or 4 fluoro groups, more preferably 2 fluoro groups, most preferably on $R^3$ and $R^4$ and $R^5$ and $R^6$ represent H.

Similarly preferably, $R^2$ is fluoro and $R^3$, $R^4$, $R^5$, and $R^6$ independently represent 2, 3 or 4 fluoro groups, more preferably $R^3$ and $R^4$ are both fluoro and $R^5$ and $R^6$ represent H or all of $R^3$, $R^4$, $R^5$, and $R^6$ are fluoro.

Preferably X is $CR^8$. More preferably $R^8$ is chloro.

Other preferred compounds are those in which $R^7$ and $R^8$ are the same. More preferably, both $R^7$ and $R^8$ are Cl.

Suitably, $R^a$ is $C(O)OC_{1-6}$ alkyl, e.g. ethyl, propyl or isopropyl, with optional substitution selected from one to five fluoro groups, e.g. to form 2,2,2,-trifluoroethyl, di-$C_{1-6}$ alkylamino, e.g. dimethylamino and het, e.g. pyrrolidinyl, pyridyl and imidazolyl. More suitably, $R^a$ is ethoxycarbonyl, dimethylaminoethoxycarbonyl, 2,2,2-trifluoroethoxycarbonyl, isopropoxycarbonyl, 4-pyridylmethoxycarbonyl, 3-pyridylmethoxycarbonyl, 2-pyridylmethoxycarbonyl, 1H-imidazol-5-ylmethoxycarbonyl or 2-pyrrolidin-1-ylethoxycarbonyl.

Equally suitably, $R^a$ is $C_{1-6}$ alkyl, e.g. methyl, with optional substitution selected from one to five fluoro groups, e.g. to form trifluoromethyl, $C_{3-8}$ cycloalkyl, e.g. cyclohexyl, phenyl and het, e.g. pyridyl, e.g. 4-pyridyl, piperidinyl, morpholinyl, pyrrolidinyl or piperazinyl. More suitably, $R^a$ is methyl or 4-pyridylmethyl.

Equally suitably, $R^a$ and $R^b$ together with the N atom to which they are attached form a pyrrolidinyl, piperidinyl, piperazinyl, morpholinyl or 2-oxo-oxazolidinyl, e.g. 2-oxo-1,3-oxazolidin-3-yl group, more suitably, a 2-oxo-1,3-oxazolidin-3-yl group.

Suitably, $R^b$ is hydrogen.

Preferably or alternatively, $R^9$ is selected from $NH_2$, $C_{1-6}$ alkoxycarbonylamino, with optional substitution on the alkoxy group by one to five fluoro groups, di-$C_{1-6}$ alkylamino and het, and $C_{1-6}$ alkylamino, with optional substitution on the alkyl group by one to five fluoro groups, $C_{3-8}$ cycloalkyl, phenyl and het. Most preferably, $R^9$ is $NH_2$.

Preferred individual compounds of formula (I) of the invention are selected from:

5-amino-1-[2,6-dichloro-4-pentafluorothiophenyl]-4-[2,2-difluoro-1-(trifluoromethyl)cyclopropyl]-1H-pyrazole-3-carbonitrile;

5-amino-1-[2,6-dichloro-4-(trifluoromethyl)phenyl]-4-[2,2-difluoro-1-(trifluoromethyl)cyclopropyl]-1H-pyrazole-3-carbonitrile;

5-amino-1-[2,6-dichloro-4-(trifluoromethyl)phenyl]-4-(1,2,2-trifluorocyclopropyl)-1H-pyrazole-3-carbonitrile;

5-amino-1-[2,6-dichloro-4-(trifluoromethyl)phenyl]-4-(pentafluorocyclopropyl)-1H-pyrazole-3-carbonitrile;

5-amino-4-(2,2-dichloro-1-fluorocyclopropyl)-1-[2,6-dichloro-4-(trifluoromethyl)phenyl]-1H-pyrazole-3-carbonitrile;

5-amino-1-[2,6-dichloro-4-pentafluorothiophenyl]-4-(pentafluorocyclopropyl)-1H-pyrazole-3-carbonitrile;

5-amino-1-[2,6-dichloro-4-pentafluorothiophenyl]-4-(1,2,2-trifluorocyclopropyl)-1H-pyrazole-3-carbonitrile;

5-amino-1-[2,6-dichloro-4-(trifluoromethyl)phenyl]-4-[1-(difluoromethyl)-2,2-difluorocyclopropyl]-1H-pyrazole-3-carbonitrile;

5-amino-1-[2,6-dichloro-4-(trifluoromethyl)phenyl]-4-(2,2-difluorocyclopropyl)-1H-pyrazole-3-carbonitrile;

5-amino-4-[2,2-difluoro-1-(trifluoromethyl)cyclopropyl]-1-[2,6-difluoro-4-(trifluoromethyl)phenyl]-1H-pyrazole-3-carbonitrile;

5-amino-1-[2,6-dichloro-4-pentafluorothiophenyl]-4-[1-(difluoromethyl)-2,2-difluorocyclopropyl]-1H-pyrazole-3-carbonitrile;

5-amino-4-{1-[chloro(fluoro)methyl]-2,2-difluorocyclopropyl}-1-[2,6-dichloro-4-(trifluoromethyl)phenyl]-1H-pyrazole-3-carbonitrile;

5-amino-1-[2,6-dichloro-4-(trifluoromethyl)phenyl]-4-[1-(difluoromethyl)-2,2,3,3-tetrafluorocyclopropyl]-1H-pyrazole-3-carbonitrile;

5-amino-1-[2,6-dichloro-4-(trifluoromethyl)phenyl]-4-[2,2,3,3-tetrafluoro-1-(trifluoromethyl)cyclopropyl]-1H-pyrazole-3-carbonitrile;

1-[2,6-dichloro-4-(trifluoromethyl)phenyl]-4-[2,2-difluoro-1-(trifluoromethyl)cyclopropyl]-5-(methylamino)-1H-pyrazole-3-carbonitrile 5-amino-1-[2,6-dichloro-4-(trifluoromethoxy)phenyl]-4-[2,2-difluoro-1-(trifluoromethyl)cyclopropyl]-1H-pyrazole-3-carbonitrile;

5-amino-1-[2,6-dichloro-4-(trifluoromethoxy)phenyl]-4-[1-(difluoromethyl)-2,2,3,3-tetrafluorocyclopropyl]-1H-pyrazole-3-carbonitrile;

5-amino-1-[2,6-dichloro-4-(trifluoromethoxy)phenyl]-4-[1-(difluoromethyl)-2,2-difluorocyclopropyl]-1H-pyrazole-3-carbonitrile;

5-amino-1-[2,6-dichloro-4-(trifluoromethyl)phenyl]-4-[2,2-difluoro-1-(fluoromethyl)cyclopropyl]-1H-pyrazole-3-carbonitrile;

5-amino-1-[2,6-dichloro-4-(trifluoromethyl)phenyl]-4-(2,2-difluoro-1-methylcyclopropyl)-1H-pyrazole-3-carbonitrile;

5-amino-1-{2,6-dichloro-4-[(trifluoromethyl)thio]phenyl}-4-[2,2-difluoro-1-(trifluoromethyl)cyclopropyl]-1H-pyrazole-3-carbonitrile;

ethyl 3-cyano-1-[2,6-dichloro-4-(trifluoromethyl)phenyl]-4-[2,2-difluoro-1-(trifluoromethyl)cyclopropyl]-1H-pyrazol-5-ylcarbamate;

1-[2,6-dichloro-4-(trifluoromethyl)phenyl]-4-[2,2-difluoro-1-(trifluoromethyl)cyclopropyl]-5-(2-oxo-1,3-oxazolidin-3-yl)-1H-pyrazole-3-carbonitrile;

5-amino-1-[3-chloro-5-(trifluoromethyl)pyridin-2-yl]-4-[2,2-difluoro-1-(trifluoromethyl)cyclopropyl]-1H-pyrazole-3-carbonitrile;

2-(dimethylamino)ethyl 3-cyano-1-[2,6-dichloro-4-(trifluoromethyl)phenyl]-4-[2,2-difluoro-1-(trifluoromethyl)cyclopropyl]-1H-pyrazol-5-ylcarbamate;

2,2,2-trifluoroethyl 3-cyano-1-[2,6-dichloro-4-(trifluoromethyl)phenyl]-4-[2,2-difluoro-1-(trifluoromethyl)cyclopropyl]-1H-pyrazol-5-ylcarbamate;

5-amino-1-{2,6-dichloro-4-[(trifluoromethyl)sulfonyl]phenyl}-4-[2,2-difluoro-1-(trifluoromethyl)cyclopropyl]-1H-pyrazole-3-carbonitrile;

1-[2,6-dichloro-4-(trifluoromethyl)phenyl]-4-[2,2-difluoro-1-(trifluoromethyl)cyclopropyl]-5-[(pyridin-4-ylmethyl)amino]-1H-pyrazole-3-carbonitrile;

5-amino-1-[2,6-dichloro-4-(difluoromethoxy)phenyl]-4-[2,2-difluoro-1-(trifluoromethyl)cyclopropyl]-1H-pyrazole-3-carbonitrile;

5-amino-1-[2,6-dichloro-4-pentafluorothiophenyl]-4-[1-(difluoromethyl)-2,2,3,3-tetrafluorocyclopropyl]-1H-pyrazole-3-carbonitrile;

Isopropyl 3-cyano-1-[2,6-dichloro-4-(trifluoromethyl)phenyl]-4-[2,2-difluoro-1-(trifluoromethyl)cyclopropyl]-1H-pyrazol-5-ylcarbamate;

pyridin-4-ylmethyl 3-cyano-1-[2,6-dichloro-4-(trifluoromethyl)phenyl]-4-[2,2-difluoro-1-(trifluoromethyl)cyclopropyl]-1H-pyrazol-5-ylcarbamate;

pyridin-3-ylmethyl 3-cyano-1-[2,6-dichloro-4-(trifluoromethyl)phenyl]-4-[2,2-difluoro-1-(trifluoromethyl)cyclopropyl]-1H-pyrazol-5-yl]-carbamate;

pyridin-2-ylmethyl 3-cyano-1-[2,6-dichloro-4-(trifluoromethyl)phenyl]-4-[2,2-difluoro-1-(trifluoromethyl)cyclopropyl]-1H-pyrazol-5-ylcarbamate;

1H-imidazol-5-ylmethyl 3-cyano-1-[2,6-dichloro-4-(trifluoromethyl)phenyl]-4-[2,2-difluoro-1-(trifluoromethyl)cyclopropyl]-1H-pyrazol-5-ylcarbamate;

2-pyrrolidin-1-ylethyl 3-cyano-1-[2,6-dichloro-4-(trifluoromethyl)phenyl]-4-[2,2-difluoro-1-(trifluoromethyl)cyclopropyl]-1H-pyrazol-5-ylcarbamate; and 5-amino-4-{1-[chloro(difluoro)methyl]-2,2-difluorocyclopropyl}-1-[2,6-dichloro-4-(trifluoromethyl)phenyl]-1H-pyrazole-3-carbonitrile; or a pharmaceutically acceptable salt or prodrug thereof.

More preferred individual compounds of formula (I) of the present invention are selected from:

5-amino-1-[2,6-dichloro-4-(trifluoromethyl)phenyl]-4-[2,2-difluoro-1-(trifluoromethyl)cyclopropyl]-1H-pyrazole-3-carbonitrile;

(−)-5-amino-1-[2,6-dichloro-4-(trifluoromethyl)phenyl]-4-[2,2-difluoro-1-(trifluoromethyl)cyclopropyl]-1H-pyrazole-3-carbonitrile;

5-amino-1-[2,6-dichloro-4-(trifluoromethyl)phenyl]-4-[1-(difluoromethyl)-2,2-difluorocyclopropyl]-1H-pyrazole-3-carbonitrile;

5-amino-1-[2,6-dichloro-4-pentafluorothiophenyl]-4-[1-(difluoromethyl)-2,2-difluorocyclopropyl]-1H-pyrazole-3-carbonitrile;

5-amino-4-{1-[chloro(fluoro)methyl]-2,2-difluorocyclopropyl}-1-[2,6-dichloro-4-(trifluoromethyl)phenyl]-1H-pyrazole-3-carbonitrile;

5-amino-1-[2,6-dichloro-4-(trifluoromethyl)phenyl]-4-[1-(difluoromethyl)-2,2,3,3-tetrafluorocyclopropyl]-1H-pyrazole-3-carbonitrile; and 5-amino-1-[2,6-dichloro-4-(trifluoromethyl)phenyl]-4-[2,2,3,3-tetrafluoro-1-(trifluoromethyl)cyclopropyl]-1H-pyrazole-3-carbonitrile; or a pharmaceutically acceptable salt or prodrug thereof.

Within the scope of the invention are so-called 'prodrugs' of the compounds of the invention. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. It will be appreciated that certain compounds of formula (I) may themselves act as prod-drugs of other compounds of formula (I). Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs in accordance with the invention can, for example, be produced by replacing the 5-amino substituent on the pyrazole ring in the compounds of formula (I) with certain moieties known to those skilled in the art as 'pro-drug moieties' as described, for example, in "Design of Prodrugs" by H Bundgaard (Elsevier, 1985); "Design and application of prodrugs," Textbook of Drug Design and Discovery, ($3^{rd}$ Edition), 2002, 410-458, (Taylor and Francis Ltd., London); and references therein.

Suitable prodrugs may have an N-containing group at the 5-position of the pyrazole ring /////of formula (I) and are bound to the ring through N. The 5-N group can be substituted once or twice. Examples of substituents include: alkyl amines, aryl amines, amides, ureas, carbamates, cyclic carbamates, imines, enamines, imides, cyclic imides, sulfenamides, and sulfonamides. The hydrocarbon portion of these groups contain $C_{1-6}$ alkyl, phenyl, heteroaryl such as pyridyl, $C_{2-6}$ alkenyl, and $C_{3-8}$ cycloalkyl; wherein each of the above groups may include one or more optional substituents where chemically possible independently selected from: halo; hydroxy; $C_{1-6}$ alkyl and $C_{1-6}$ alkoxy.

Further examples of replacement groups in accordance with the foregoing example and examples of other prodrug types may be found in the aforementioned references.

A prodrug according to the invention can be readily identified by administering it to a test animal and sampling a body fluid for a compound of the invention.

In a further aspect, the present invention provides processes for the preparation of a compound of formula (I), or a pharmaceutically, veterinarily or agriculturally acceptable salt thereof, or a pharmaceutically, veterinarily or agriculturally acceptable solvate (including hydrate) of either entity, as illustrated below.

It will be apparent to those skilled in the art that sensitive functional groups may need to be protected and deprotected during synthesis of a compound of formula (I) of the invention. This may be achieved by conventional methods, for example as described in "Protective Groups in Organic Synthesis" by T W Greene and P G M Wuts, John Wiley & Sons Inc (1999), and references therein.

Thus, the following processes are illustrative of the general synthetic procedures which may be adopted in order to obtain the compounds of formula (I) of the invention.

A compound of formula (I) may be prepared by cyclopropanation of an alkene of formula (II):

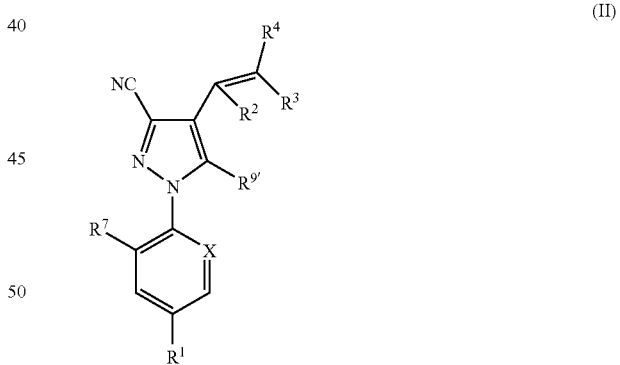

(II)

wherein $R^1$, $R^2$, $R^3$, $R^4$, $R^7$ and X are as previously defined for formula (I) and $R^{9'}$ represents $R^9$ or N-protected $R^9$, followed by deprotection where necessary. Suitable protection includes imidoformamide protection, for example using N,N-dimethylimidoformamide, which may be deprotected under standard conditions. Compounds of formula (II) may be reacted with a carbenoid species, :$CR^5R^6$, in which $R^5$ and $R^6$ are as previously defined for formula (I), which may be generated in situ. For example, when $R^5$=$R^6$=F, a reactive species such as trimethylsilyl difluoro(fluorosulfonyl)acetate (TFDA) may be reacted with a compound of formula (II), where $R^{9'}$ represents N-protected $R^9$, with an optional apolar solvent at elevated temperature in the presence of sodium fluoride to yield a product of formula (I) after deprotection.

Other specific methods include treatment of chloroform with base, preferably under phase transfer catalysis conditions, thermolysis of a suitable organometallic precursor such as an aryl trifluoromethyl, trichloromethyl, or phenyl(trifluoromethyl) mercury derivative or treatment with a diazoalkane in the presence of a transition metal catalyst and treatment with a diazoalkane in the absence of a transition metal catalyst followed by thermolysis of the intermediate pyrazoline, or generation from a sulphur ylid.

A compound of formula (II), where $R^{9'}$ represents an N-protected group, may be obtained from a compound of formula (IV):

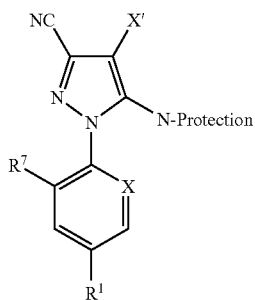

(IV)

wherein X' is bromo or iodo, and $R^1$, $R^7$ and X are as previously defined for formula (IIa), for example, by a transition metal-catalysed cross-coupling reaction of (IV) with an appropriate vinylation reagent in a suitable, optionally degassed, solvent. Suitably, the transition metal is palladium and the vinylation reagent is an organotin, organoboronic acid, or organozinc derivative. Alternatively, (IV) may be heated at reflux with suitably substituted alkenylboronic acids in the presence of tetrakis(triphenyiphosphine)-palladium (0) and sodium hydrogen carbonate in a suitable solvent. Alternatively, (IV) may be treated with an organozinc compound, for example, activated zinc (such as Rieke zinc) under an inert atmosphere with a suitable bromoalkene such as bromotrifluoroethylene or bromodifluoroethylene in an aprotic solvent in the presence of a palladium (0) species such as tetrakis(triphenylphosphine)palladium (0) at elevated temperature. Alternatively, (IV) may be treated with activated zinc (Rieke zinc) in an aprotic solvent to yield the organozincate, which can then be crossed coupled to the haloalkene in the presence of a palladium (II) species such as dichlorobis (triphenylphosphine)palladium (II) and a reducing agent such as diisobutylaluminium hydride under reflux in an aprotic solvent.

Compounds of formula (IV) may be useful for accessing intermediates of formula (V).

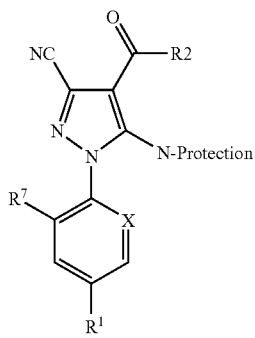

(V)

Thus, formula (IV) can be treated with a Grignard reagent such as isopropylmagnesium chloride under inert conditions using an aprotic solvent at reduced temperature before treatment with a chloroalkanoic acid chloride or anhydride, upon warming to room temperature the desired ketone species represented by formula (V) is produced.

Compounds of formula (V) can be utilised to access compounds of formula (II) wherein $R^3$ and $R^4$ are H and $R^9$ is N-protected. Thus, formula (V) can be methylenated by treatment with a Wittig reagent under inert conditions at reduced temperature in a solvent such as tetrahydrofuran.

Compounds of formula (II), where $R^9$ is N-protected, can also be obtained from compounds of formula (V), by treatment with a haloalkene such as dibromodifluoromethane in the presence of triphenylphosphine and Rieke zinc in an aprotic solvent.

Alternatively, compounds of formula (II), where $R^9$ is N-protected, may be prepared from compounds of formula (IV) via an appropriate tertiary alcohol followed by standard chlorination-dehydrochlorination procedures.

A compound of formula (IV) may be obtained from a compound of formula (VI) wherein $R^1$, $R^7$, and X are as previously defined for formula (I):

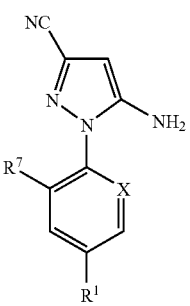

(VI)

by two standard bromination/iodination and protection steps, either of which may be carried out first. Compounds of formula (VI) may be readily protected, for example as the imidoformamide, and can then be transformed directly into compounds of formula (V) by reaction with a reactive acid anhydride, in an apolar solvent.

A compound of formula (I) may also be prepared by generating the required carbenoid species from a pyrazole-containing precursor and treating it with an appropriate alkene. For example, the alkyl metal salt, preferably lithium, of a compound of formula (VII):

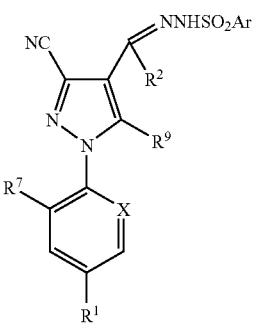

(VII)

wherein Ar is phenyl or naphthyl, either of which is optionally substituted with $C_1$ to $C_4$ alkyl, $C_1$ to $C_4$ alkoxy or halo, and $R^1$, $R^2$, $R^7$, $R^9$ and X are as previously defined, may be thermally decomposed in the presence of a transition metal catalyst, such as rhodium (II) acetate, and an alkene of formula (VIII):

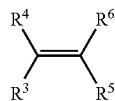

(VIII)

wherein $R^3$, $R^4$, $R^5$ and $R^6$ are as previously defined for formula (I), optionally in a suitable solvent such as dichloromethane and optionally under pressure, to give a compound of formula (I).

Compounds of formula (I) may be prepared by the Japp-Klingemann reaction. This reaction is described in Org. React., 1959, 10, 143-178. It is usually necessary to perform further synthetic steps to form 3,4,5-trisubstituted pyrazoles with more varied 4-substituents. Futhermore, the groups that can be introduced in this way are limited to those derivable from the 4-substituent originally introduced. However, we have found a process by which 3,4,5-trisubstituted 1-arylpyrazoles may be produced directly in a reaction which involves coupling of an aryldiazonium species with an appropriately substituted precursor bearing a desired substituent. The desired substituent is introduced concomitantly at the C-4 position in a process, which does not involve any rearrangement. Furthermore, the reaction produces the tri-substitued pyrazole directly. This removes the need for a lengthy synthetic procedure and the need for several work-ups of the intermediate products and results in good yields. The process has the significant advantage that the C-4 substituent may be built into the original tetrasubstituted ethane derivative which is one of the starting materials and which is reacted with the aryldiazonium species to form the pyrazole. Control of the position of substitution on the resulting pyrazole ring is therefore absolute in the reaction. Furthermore, a very wide variety of 4-substituents may be introduced conveniently and directly.

Thus, a compound of formula (I) in which $R^9$ is $NH_2$, can be prepared by reacting a compound of formula (IX)

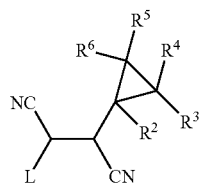

(IX)

with a compound of formula (X)

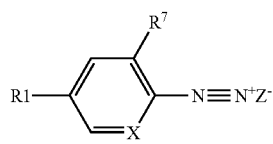

(X)

optionally in the presence of an acid, wherein:

$R^1$ to $R^8$ are as defined above in relation to the compounds of formula (I);

L is an activating group; and

Z is a compatible counter ion, followed by removal of group L.

The counter ion $Z^-$ may be any suitable counter ion normally found in diazonium reactions. Preferably, $Z^-$ is halogen, $HSO_4^-$, or tetrafluoroborate and most preferably is tetrafluoroborate.

The group L is an electron withdrawing group which stabilises the anion intermediate in the process. Thus, preferably, L is a group which is capable of stabilising a negative charge on an adjacent carbon atom. The group L must also be removable. L can be removed under basic conditions, for example by base hydrolysis or can be removed by reduction and/or elimination. The group L is important as it serves to direct the reaction of the diazonium species with the compound of formula (IX) but then is removed in the subsequent stages of the reaction. Preferably L is an ester group or a group $COR^{10}$. More preferably, L is a group selected from: $-S(O)_pR^{11}$ where p is 1 or 2, $(R^{11}O)_2PO$, $COOR^{11}$ and $-COR^{10}$, wherein $R^{10}$ is selected from: $C_{1-8}$ alkyl, di-$C_{1-8}$ alkylamino, $C_{1-8}$ alkylthio, $C_{3-8}$ cycloalkyl, $(CH_2)_n$Ph and $(CH_2)_n$ heteroaryl wherein n=0, 1 or 2, each of which groups may be optionally substituted on any carbon atom by one or more groups selected independently from: halogen, hydroxy, cyano, nitro, $C_{1-4}$ alkoxy, $C_{1-4}$ haloalkoxy, $C_{1-4}$ alkanoyl, $C_{1-4}$ haloalkanoyl, $C_{1-4}$ alkylsulphinyl, $C_{1-4}$ haloalkylsulphinyl, $C_{1-4}$ alkylsulphonyl, $C_{1-4}$ haloalkylsulphonyl, $C_{3-8}$ cycloalkyl and $C_{3-8}$ halocycloalkyl; and $R^{10}$ can be hydrogen; and wherein $R^{11}$ is selected from: $C_{1-8}$ alkyl, $C_{3-8}$ cycloalkyl, $(CH_2)_n$Ph and $(CH_2)_n$ heteroaryl wherein n=0, 1 or 2, each of which groups may be optionally substituted on any carbon atom by one or more groups selected independently from: halogen, hydroxy, cyano, nitro, $C_{1-4}$ alkoxy, $C_{1-4}$ haloalkoxy, $C_{1-4}$ alkanoyl, $C_{1-4}$ haloalkanoyl, $C_{1-4}$ alkylsulphinyl, $C_{1-4}$ haloalkylsulphinyl, $C_{1-4}$ alkylsulphonyl, $C_{1-4}$ haloalkylsulphonyl, $C_{3-8}$ cycloalkyl and $C_{3-8}$ halocycloalkyl; and $R^{11}$ can be hydrogen. Preferably L is a group selected from $COR^{10}$ and $COOR^{11}$. Most preferably L is $-COOMe$ or $-COOEt$.

In certain cases, the nature of the leaving group L means that the resulting intermediate is in the wrong oxidation state. Thus, where necessary, one or more reaction steps may be added to ensure the correct oxidation state is reached prior to cyclising to form the aryl pyrazole.

The aforementioned coupling process can be used to prepare any of the compounds of formula (I). For example, Schemes 1 and 2 below illustrate the general methods as applied in the preparation of 5-amino-1-[2,6-dichloro-4-(trifluoromethyl)phenyl]-4-[2,2-difluoro-1-(trifluoromethyl)cyclopropyl]-1H-pyrazole-3-carbonitrile.

Scheme 1

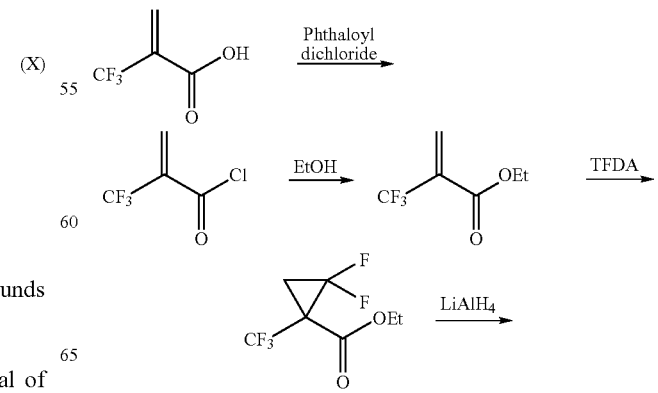

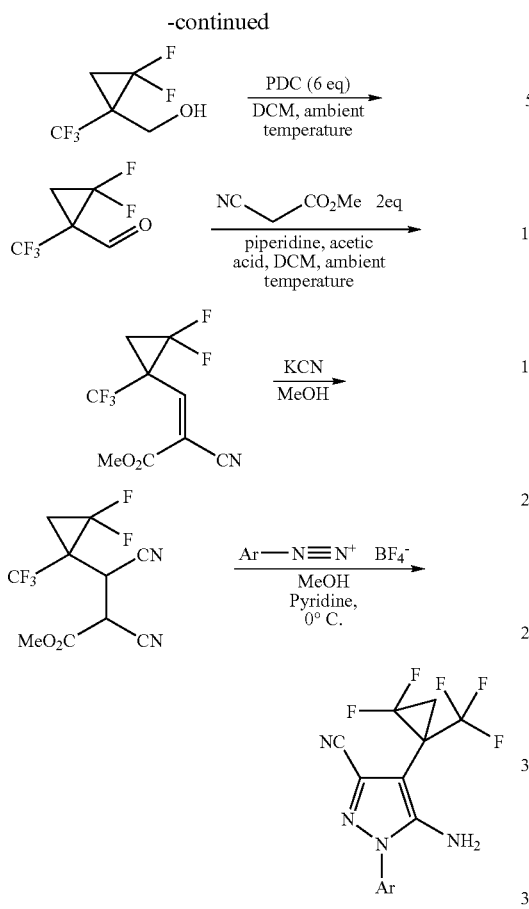

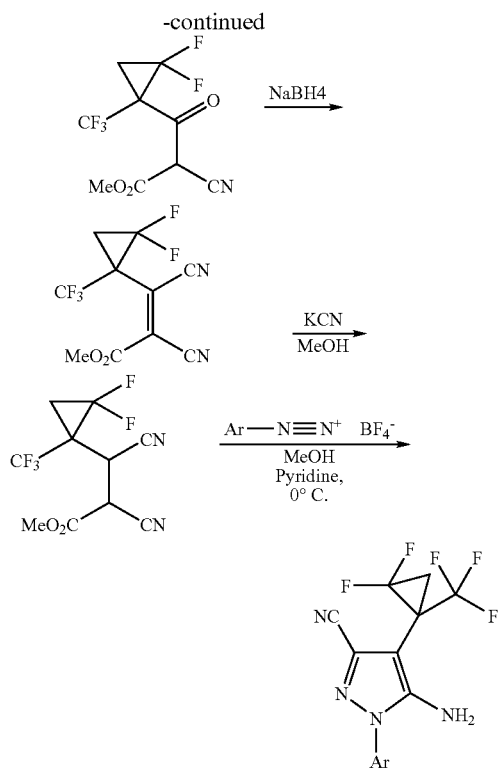

Ideally, for the coupling reaction to form the compound of formula (I), the solvent should be a polar solvent which does not react with either the diazonium salt or cation, or with the compound of formula (IX). The reaction may optionally be carried out under mildly acidic conditions.

The diazonium salt of formula (X) can be produced by conventional means and may be prepared in situ for further reaction or can be isolated and used in a subsequent reaction step. Specific examples of compounds of formula (IX) and (XI) are depicted in Scheme 1 and 2. Alternative compounds of formula (IX) can be similarly obtained from compounds of formula (XI) wherein $R^2$, $R^3$, $R^4$, $R^5$, $R^6$ and L are as defined above, for example, by treating a compound of formula (XI) with a source of cyanide ions.

(XI)

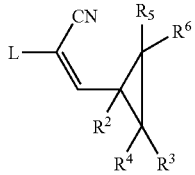

Compounds of the formula (XI) can be obtained by reducing and then dehydrating a compound of formula (XII).

(XII)

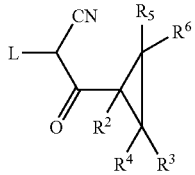

Scheme 2

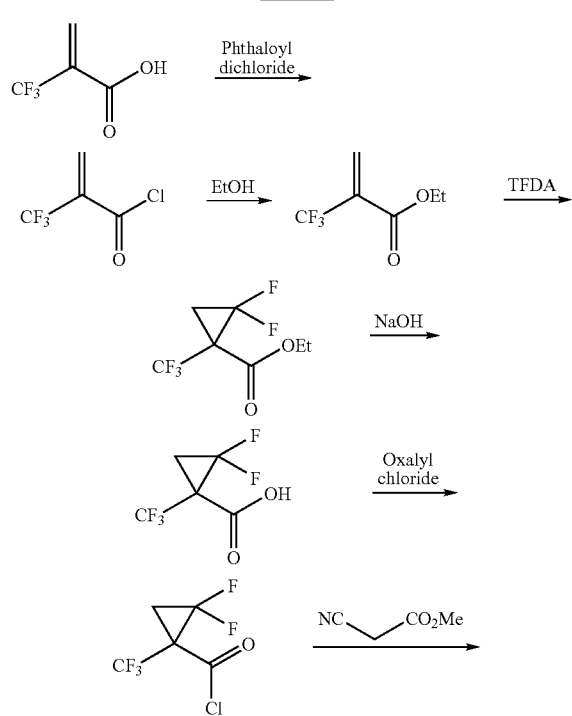

Compounds of formula (XII) can, for example, be made by condensation of an alkyl cyanoalkanoate e.g. methyl cyanoacetate with an acid chloride in an aprotic solvent such as dichloromethane in the presence of a Lewis acid, such as magnesium chloride and a mild base, such as triethylamine, at reduced temperature.

Alternatively as shown in Scheme 1, compounds of formula (XI) can be accessed by Knoevenagel condensation of a suitable aldehyde with an alkyl alkanoate such as methyl cyanoacetate.

Effective conditions for preparing cyclopropyl substituted compounds using trimethylsilyl-2,2-difluoro-2-(fluorosulfonyl)acetate (TFDA), a difluorocarbene source, are described by Dolbier et al., in J. Fluor Chem., 2004, 125, 459.

Compounds of formula (XIII) may also be utilised in the Japp Klingemann upon reaction with compounds of formula (X) in order to synthesise compounds of formula (VI), by analogy with the above conditions.

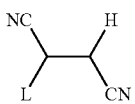

(XIII)

Compounds of formula (XIII) wherein L=$CO_2C_1$ to $C_6$ alkyl are synthesised by the slow addition of glycolonitrile optionally at decreased temperatures to a $C_1$ to $C_6$ alkyl cyanoacetate, in an aprotic solvent such as dimethylformamide, followed by the addition of a base such as potassium carbonate.

The intermediates of formula (VIII), (XI) and (XII) can also be obtained either by analogy with Schemes 1 and 2 or by using conventional synthetic procedures, in accordance with standard textbooks on organic chemistry or literature precedent, from readily accessible starting materials using appropriate reagents and reaction conditions.

In another aspect, the invention provides processes for the preparation of compounds of formula (I) from alternative compounds of formula (I). For example, compounds in which $R^9$=$NR^aR^b$, where $R^a$ and $R^b$ are as defined in formula (I) may be prepared by standard reactions from a compound of formula (I) where $R^9$ represents $NH_2$.

Compounds of formula (VI) may be prepared from compounds of formula (XIV)

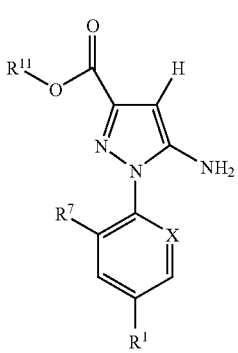

where $CO_2R^{11}$ represents a suitable ester group, by conversion of the ester into the amide (XV) followed by reduction with phosphorous oxychloride at elevated temperature.

Compounds of formula (XIV) can be obtained by reaction of a suitable 3-cyano-2-oxo-propionic acid ester, e.g. ethyl ester, with a suitably substituted hydrazine of compound (XVII) in an alcoholic solvent at elevated temperature followed by addition of a base such as sodium carbonate and further heating.

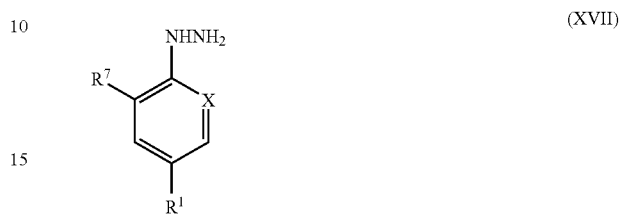

(XVII)

Compounds of formula (XVII) are readily accessed using standard conditions, for example by substitution of the corresponding fuoro derivative with a hydrazine reagent such as hydrazine monohydrate at reflux in an alcoholic solvent such as ethanol.

A compound of formula (I), where $R^2$ is $CF_3$, $R^3$ and $R^4$ are fluoro, R and $R^6$ are hydrogen and $R^9$ is $NH_2$, may conveniently be prepared according to the following Scheme 3:—

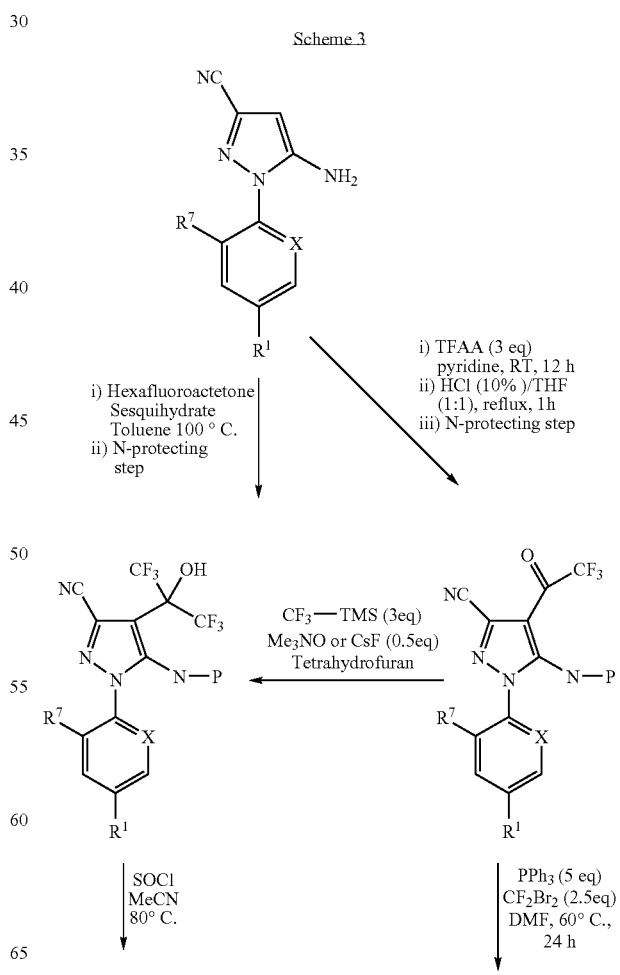

Scheme 3

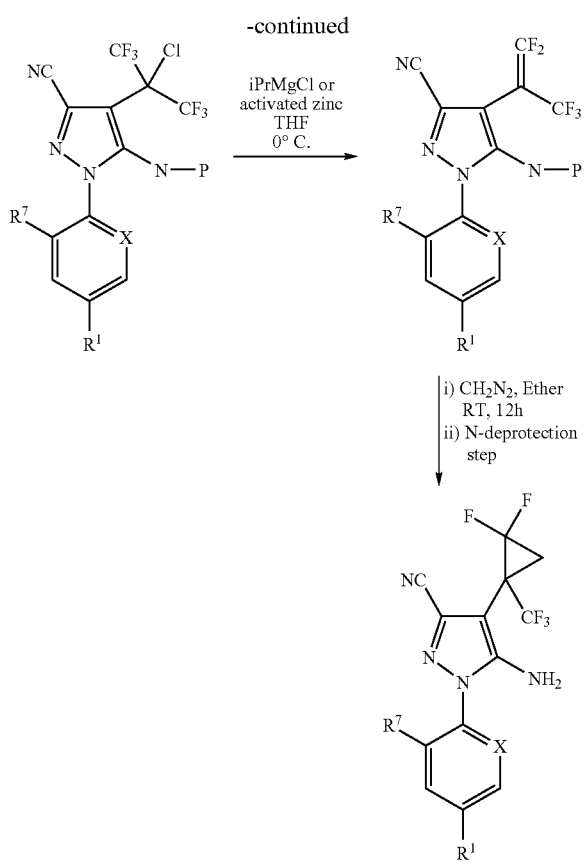

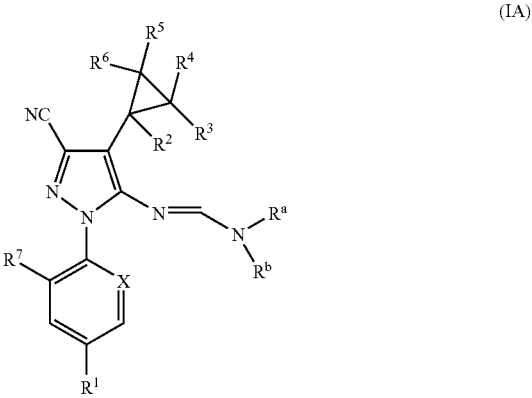

chemist will exercise his judgement and skill as to the most efficient sequence of reactions for synthesis of a given target compound.

The present invention also relates to intermediates of formula (IA) below:

(IA)

wherein $R^1$ to $R^7$, X and $R^a$ and $R^b$ are as defined in relation to compounds of formula (I) and where the preferences applied to $R^1$ to $R^7$ and X apply equally to formula (IA). With reference to formula (IA), suitably $R^a=R^b=$methyl.

It is to be understood that compounds of formula (I) may contain one or more asymmetric carbon atoms, thus compounds of the invention can exist as two or more stereoisomers.

Included within the scope of the present invention are all stereoisomers such as enantiomers and diasteromers, all geometric isomers and tautomeric forms of the compounds of formula (I), including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Geometric isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer (s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art—see, The N-protecting group is a suitable acid labile protecting group, e.g. a dimethylamidoformamido group, which may be incorporated according to methods described herein and removed under acidic conditions, e.g. hydrochloric acid in methanol and dioxan at elevated temperature. The transformations described are well known to hose skilled in the art and, in part, are described in more detail herein.

Persons skilled in the art will be aware of variations of, and alternatives to, the processes described which allow the compounds defined by formula (I) to be obtained.

It will also be appreciated by persons skilled in the art that, within certain of the processes described, the order of the synthetic steps employed may be varied and will depend inter alia on factors such as the nature of other functional groups present in a particular substrate, the availability of key intermediates, and the protecting group strategy (if any) to be adopted. Clearly, such factors will also influence the choice of reagent for use in the said synthetic steps.

The skilled person will appreciate that the compounds of formula (I) of the invention could be made by methods other than those herein described, by adaptation of the methods herein described and/or adaptation of methods known in the art, for example the art described herein, or using standard textbooks such as "Comprehensive Organic Transformations-A Guide to Functional Group Transformations", R C Larock, Wiley-VCH (1999 or later editions).

It is to be understood that the synthetic transformation methods mentioned herein are exemplary only and they may be carried out in various different sequences in order that the desired compounds can be efficiently assembled. The skilled for example, "Stereochemistry of Organic Compounds" by E L Eliel (Wiley, New York, 1994).

The pharmaceutically, veterinarily and agriculturally acceptable acid addition salts of certain of the compounds of formula (I) may also be prepared in a conventional manner. For example, a solution of a free base may be treated with the appropriate acid, either neat or in a suitable solvent, and the resulting salt isolated either by filtration or by evaporation under reduced pressure of the reaction solvent. For a review on suitable salts, see "Handbook of Pharmaceutical Salts: Properties, Selection, and Use" by Stahl and Wermuth (Wiley-VCH, Weinheim, Germany, 2002).

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

The compounds of the invention, i.e. those of formula (I), possess parasiticidal activity in humans, animals and plants. They are particularly useful in the treatment of ectoparasites.

Regarding the use of the compounds of the invention in mammals, there is provided:

a pharmaceutical parasiticidal composition comprising a compound of formula (I), or a pharmaceutically acceptable salt thereof, or a pharmaceutically acceptable solvate of either entity, together with a pharmaceutically acceptable diluent or carrier, which may be adapted for oral, parenteral or topical administration;

a compound of formula (I), or a pharmaceutically acceptable salt thereof, or a pharmaceutically acceptable solvate of either entity, or a pharmaceutical composition containing any of the foregoing, for use as a medicament;

the use of a compound of formula (I), or a pharmaceutically acceptable salt thereof, or a pharmaceutically acceptable solvate of either entity, or a pharmaceutical composition containing any of the foregoing, for the manufacture of a medicament for the treatment of a parasitic infestation; and a method of treating a parasitic infestation in a mammal which comprises treating said mammal with an effective amount of a compound of formula (I), or a pharmaceutically acceptable salt thereof, or a pharmaceutically acceptable solvate of either entity, or a pharmaceutical composition containing any of the foregoing.

According to another aspect of the present invention, there is provided a method for the control of arthropod, plant nematode or helminth pests at a locus which comprises the treatment of the locus (e.g. by application or administration) with an effective amount of a compound of general formula I, or a pesticidally acceptable salt thereof.

The present invention includes all pharmaceutically acceptable isotopically-labelled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Compounds of the invention can also be mixed with one or more biologically active compounds or agents including insecticides, acaricides, anthelmintics, fungicides, nematocides, antiprotozoals, bactericides, growth regulators, entomopathogenic bacteria, viruses or fungi to form a multi-component pesticide giving an even broader spectrum of pharmaceutical, veterinary or agricultural utility. Thus, the present invention also pertains to a composition comprising a biologically effective amount of compounds of formula I of the invention and an effective amount of at least one additional biologically active compound or agent and can further comprise one or more of surfactant, a solid diluent or a liquid diluent. Specific further active compounds include those described in UK Patent Application No. GB0406137.0, at pages 37 to 41.

The following list of biologically active compounds together with which the compounds of formula I of the invention can be used is intended to illustrate the possible combinations, but not to impose any limitation. The invention includes, by example and not limitation, any one individually or more than one of the biologically active compounds discussed herein together with any compound of formula I, with any variable or specific compound of formula I, as discussed herein.

For example, compounds of the present invention may be co-administered or used in combination with anthelmintic agents. Such anthelmintic agents include, compounds selected from the macrocyclic lactone class of compounds such as any one one or more of the following: ivermectin, avermectin, abamectin, emamectin, eprinomectin, doramectin, selamectin, moxidectin, nemadectin and milbemycin derivatives as described in EP-357460, EP-444964 and EP-594291. Additional anthelmintic agents include semisynthetic and biosynthetic avermectin/milbemycin derivatives such as those described in U.S. Pat. No. 5,015,630, WO-9415944 and WO-9522552. Additional anthelmintic agents include the benzimidazoles such as albendazole, cambendazole, fenbendazole, flubendazole, mebendazole, oxfendazole, oxibendazole, parbendazole, and other members of the class. Additional anthelmintic agents include imidazothiazoles and tetrahydropyrimidines such as tetramisole, levamisole, pyrantel pamoate, oxantel or morantel. Additional anthelmintic agents include flukicides, such as triclabendazole and clorsulon and the cestocides, such as praziquantel and epsiprantel.

Compounds of this invention may also be used in combination with derivatives and analogues of the paraherquamide/marcfortine class of anthelmintic agents, as well as the antiparasitic oxazolines such as those disclosed in U.S. Pat. No. 5,478,855, U.S. Pat. No. 4,639,771 and DE-19520936.

Compounds of this invention may be co-administered or used in combination with derivatives and analogues of the general class of dioxomorpholine antiparasitic agents as described in WO-9615121 and also with anthelmintic active cyclic depsipeptides such as those described in WO-9611945, WO-9319053, WO-9325543, EP-626375, EP-382173, WO-9419334, EP-382173, and EP-503538.

Compounds of this invention may be co-administered or used in combination with other ectoparasiticides; for example, any one one or more of the following: fipronil; pyrethroids; organophosphates; insect growth regulators such as lufenuron; ecdysone agonists such as tebufenozide and the like; neonicotinoids such as imidacloprid and the like.

The compounds of the invention may be co-administered or used in combination with terpene alkaloids, for example those described in International Patent Application Publication Numbers WO95/19363 or WO04/72086, particularly the compounds disclosed therein.

Other examples of such biologically active compounds include but are not restricted to any one one or more the following independently being:

Organophosphates: acephate, azamethiphos, azinphos-ethyl, azinphos-methyl, bromophos, bromophos-ethyl, cadusafos, chlorethoxyphos, chlorpyrifos, chlorfenvinphos, chlormephos, demeton, demeton-S-methyl, demeton-S-methyl sulphone, dialifos, diazinon, dichlorvos, dicrotophos, dimethoate, disulfoton, ethion, ethoprophos, etrimfos, famphur, fenamiphos, fenitrothion, fensulfothion, fenthion, flupyrazofos, fonofos, formothion, fosthiazate, heptenophos, isazophos, isothioate, isoxathion, malathion, methacriphos, methamidophos, methidathion, methyl-parathion, mevinphos, monocrotophos, naled, omethoate, oxydemeton-methyl, paraoxon, parathion, parathion-methyl, phenthoate, phosalone, phosfolan, phosphocarb, phosmet, phosphamidon, phorate, phoxim, pirimiphos, pirimiphos-methyl, profenofos, propaphos, proetamphos, prothiofos, pyraclofos, pyridapenthion, quinalphos, sulprophos, temephos, terbufos, tebupirimfos, tetrachlorvinphos, thimeton, triazophos, trichlorfon, vamidothion.

Carbamates: alanycarb, aldicarb, 2-sec-butylphenyl methylcarbamate, benfuracarb, carbaryl, carbofuran, carbosulfan, cloethocarb, ethiofencarb, fenoxycarb, fenthiocarb, furathiocarb, HCN-801, isoprocarb, indoxacarb, methiocarb, methomyl, 5-methyl-m-cumenylbutyryl(methyl)carbamate, oxamyl, pirimicarb, propoxur, thiodicarb, thiofanox, triazamate, UC-51717

Pyrethroids: acrinathin, allethrin, alphametrin, 5-benzyl-3-furylmethyl (E)-(1R)-cis-2,2-dimethyl-3-(2-oxothiolan-3-ylidenemethyl)cyclopropanecarboxylate, bifenthrin, β-cyfluthrin, cyfluthrin, α-cypermethrin, β-cypermethrin, bioallethrin, bioallethrin((S)-cyclopentylisomer), bioresmethrin, bifenthrin, NCI-85193, cycloprothrin, cyhalothrin, cythithrin, cyphenothrin, deltamethrin, empenthrin, esfenvalerate, ethofenprox, fenfluthrin, fenpropathrin, fenvalerate, flucythrinate, flumethrin, fluvalinate (D isomer), imiprothrin, cyhalothrin, λ-cyhalothrin, permethrin, phenothrin, prallethrin, pyrethrins (natural products), resmethrin, tetramethrin, transfluthrin, theta-cypermethrin, silafluofen, τ-fluvalinate, tefluthrin, tralomethrin, Zeta-cypermethrin.

Arthropod growth regulators: a) chitin synthesis inhibitors: benzoylureas: chlorfluazuron, diflubenzuron, fluazuron, flucycloxuron, flufenoxuron, hexaflumuron, lufenuron, novaluron, teflubenzuron, triflumuron, buprofezin, diofenolan, hexythiazox, etoxazole, chlorfentazine; b) ecdysone antagonists: halofenozide, methoxyfenozide, tebufenozide; c) juvenoids: pyriproxyfen, methoprene, fenoxycarb; d) lipid biosynthesis inhibitors: spirodiclofen Other antiparasitics: acequinocyl, amitraz, AKD-1022, ANS-118, azadirachtin, Bacillus thuringiensis, bensultap, bifenazate, binapacryl, bromopropylate, BTG-504, BTG-505, camphechlor, cartap, chlorobenzilate, chlordimeform, chlorfenapyr, chromafenozide, clothianidine, cyromazine, diacloden, diafenthiuron, DBI-3204, dinactin, dihydroxymethyldihydroxypyrrolidine, dinobuton, dinocap, endosulfan, ethiprole, ethofenprox, fenazaquin, flumite, MTI-800, fenpyroximate, fluacrypyrim, flubenzimine, flubrocythrinate, flufenzine, flufenprox, fluproxyfen, halofenprox, hydramethylnon, IKI-220, kanemite, NC-196, neem guard, nidinorterfuran, nitenpyram, SD-3565 1, WL-108477, pirydaryl, propargite, protrifenbute, pymethrozine, pyridaben, pyrimidifen, NC-111, R-195, RH-0345, RH-2485, RYI-210, S-1283, S-1833, SI-8601, silafluofen, silomadine, spinosad, tebufenpyrad, tetradifon, tetranactin, thiacloprid, thiocyclam, thiamethoxam, tolfenpyrad, triazamate, triethoxyspinosyn, trinactin, verbutin, vertalec, YI-5301

Fungicides: acibenzolar, aldimorph, ampropylfos, andoprim, azaconazole, azoxystrobin, benalaxyl, benomyl, bialaphos, blasticidin-S, Bordeaux mixture, bromuconazole, bupirimate, carpropamid, captafol, captan, carbendazim, chlorfenazole, chloroneb, chloropicrin, chlorothalonil, chlozolinate, copper oxychloride, copper salts, cyflufenamid, cymoxanil, cyproconazole, cyprodinil, cyprofuram, RH-7281, diclocymet, diclobutrazole, diclomezine, dicloran, difenoconazole, RP-407213, dimethomorph, domoxystrobin, diniconazole, diniconazole-M, dodine, edifenphos, epoxiconazole, famoxadone, fenamidone, fenarimol, fenbuconazole, fencaramid, fenpiclonil, fenpropidin, fenpropimorph, fentin acetate, fluazinam, fludioxonil, flumetover, flumorf/flumorlin, fentin hydroxide, fluoxastrobin, fluquinconazole, flusilazole, flutolanil, flutriafol, folpet, fosetyl-aluminium, furalaxyl, furametapyr, hexaconazole, ipconazole, iprobenfos, iprodione, isoprothiolane, kasugamycin, krsoxim-methyl, mancozeb, maneb, mefenoxam, mepronil, metalaxyl, metconazole, metominostrobin/fenominostrobin, metrafenone, myclobutanil, neo-asozin, nicobifen, orysastrobin, oxadixyl, penconazole, pencycuron, probenazole, prochloraz, propamocarb, propioconazole, proquinazid, prothioconazole, pyrifenox, pyraclostrobin, pyrimethanil, pyroquilon, quinoxyfen, spiroxamine, sulfur, tebuconazole, tetrconazole, thiabendazole, thifluzamide, thiophanate-methyl, thiram, tiadinil, triadimefon, triadimenol, tricyclazole, trifloxystrobin, triticonazole, validamycin, vinclozin Biological agents: *Bacillus thuringiensis* ssp aizawai, kurstaki, *Bacillus thuringiensis* delta endotoxin, baculovirus, entomopathogenic bacteria, virus and fungi Bactericides: chlortetracycline, oxytetracycline, streptomycin, A suitable combination according to the present invention includes a compound of formula (I), more suitably an exemplified compound of formula (I), even more suitably a preferred individual compound as hereinbefore listed, most suitably 5-amino-1-[2,6-dichloro-4-(trifluoromethyl)phenyl]-4-[2,2-difluoro-1-(trifluoromethyl)cyclopropyl]-1H-pyrazole-3-carbonitrile in combination with one or more, preferably one, of the active compounds recited above, suitably an anthelmintic agent, such as a compound selected from the macrocyclic lactone class of compounds such as ivermectin, avermectin, abamectin, emamectin, eprinomectin, doramectin, selamectin, moxidectin and nemadectin, more suitably doramectin or selamectin.

The compounds and components of this invention should be considered independent and or capable of being combined in any fashion. Definitions in the specification and claims may be independent, dependent or multiply dependent according to their description.

Compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

With respect to their use in mammals, the compounds may be administered alone or in a formulation appropriate to the specific use envisaged, the particular species of host mammal being treated and the parasite involved.

The methods by which the compounds may be administered include oral administration by capsule, bolus, tablet, powders, lozenges, chews, multi and nanoparticulates, gels, solid solution, films, sprays, or liquid formulation. Liquid forms include suspensions, solutions, syrups, drenches and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet. Oral drenches are commonly prepared by dissolving or suspending the active ingredient in a suitable medium.

Thus compositions useful for oral administration may be prepared by mixing the active ingredient with a suitable finely divided diluent and/or disintegrating agent and/or binder, and/or lubricant etc. Other possible ingredients include antioxidants, colourants, flavouring agents, preservatives and taste-masking agents.

For oral dosage forms, depending on dose, the drug may make up from 1 wt % to 80 wt % of the dosage form, more typically from 5 wt % to 60 wt % of the dosage form. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Examples of diluents include lactose (monohydrate, spray-dried monohydrate, anhydrous and the like), mannitol, xylitol, dextrose, sucrose, sorbitol, microcrystalline cellulose, starch and dibasic calcium phosphate dihydrate.

Oral formulations may also optionally comprise surface active agents, such as sodium lauryl sulfate and polysorbate 80, and glidants such as silicon dioxide and talc. When present, surface active agents may comprise from 0.2 wt % to 5 wt % of the tablet, and glidants may comprise from 0.2 wt % to 1 wt % of the tablet.

Lubricants include magnesium stearate, calcium stearate, zinc stearate, sodium stearyl fumarate, and mixtures of magnesium stearate with sodium lauryl sulphate. Lubricants generally comprise from 0.25 wt % to 10 wt %, preferably from 0.5 wt % to 3 wt % of the tablet.

Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant.

The formulation of tablets is discussed in "Pharmaceutical Dosage Forms: Tablets, Vol. 1", by H. Lieberman and L. Lachman, Marcel Dekker, N.Y., N.Y., 1980 (ISBN 0-8247-6918-X).

The compounds may be administered topically to the skin or mucosa, that is dermally or transdermally. Typical formulations for this purpose include pour-on, spot-on, dip, spray, mousse, shampoo, powder formulation, gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958 by Finnin and Morgan (October 1999). Pour-on or spot-on formulations may be prepared by dissolving the active ingredient in an acceptable liquid carrier vehicle such as butyl digol, liquid paraffin or a non-volatile ester, optionally with the addition of a volatile component such as propan-2-ol. Alternatively, pour-on, spot-on or spray formulations can be prepared by encapsulation, to leave a residue of active agent on the surface of the animal. Injectable formulations may be prepared in the form of a sterile solution which may contain other substances, for example enough salts or glucose to make the solution isotonic with blood. Acceptable liquid carriers include vegetable oils such as sesame oil, glycerides such as triacetin, esters such as benzyl benzoate, isopropyl myristate and fatty acid derivatives of propylene glycol, as well as organic solvents such as pyrrolidin-2-one and glycerol formal. The formulations are prepared by dissolving or suspending the active ingredient in the liquid carrier such that the final formulation contains from 0.01 to 10% by weight of the active ingredient.

Alternatively, the compounds can be administered parenterally, or by injection directly into the blood stream, muscle or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques. Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as powdered a dried form to be used in conjunction with a suitable vehicle such as sterile, pyrogen-free water. The preparation of parenteral formulations under sterile conditions, for example, by lyophilisation, may readily be accomplished using standard pharmaceutical techniques well known to those skilled in the art. The solubility of compounds of formula (I) used in the preparation of parenteral solutions may be increased by the use of appropriate formulation techniques, such as the incorporation of solubility-enhancing agents.

Such formulations are prepared in a conventional manner in accordance with standard medicinal or veterinary practice.

These formulations will vary with regard to the weight of active compound contained therein, depending on the species of host animal to be treated, the severity and type of infection and the body weight of the host. For parenteral, topical and oral administration, typical dose ranges of the active ingredient are 0.01 to 100 mg per kg of body weight of the animal. Preferably the range is 0.1 to 10 mg per kg.

Formulations may be immediate and/or modified controlled release. Controlled release formulations include Modified release formulations including delayed-, sustained-, pulsed-, controlled, targeted, or programmed release. Suitable modified release formulations for the purposes of the invention are described in U.S. Pat. No. 6,106,864. Details of other suitable release technologies such as high energy dispersions and osmotic and coated particles are to be found in Verma et al, Pharmaceutical Technology On-line, 25(2), 1-14 (2001). The use of chewing gum to achieve controlled release is described in WO 00/35298. Alternatively, compounds of the invention may be formulated as a solid, semi-solid, or thixotropic liquid for administration as an implanted depot providing modified release of the active compound. Examples of such formulations include drug-coated stents and PGLA microspheres.

As an alternative the compounds may be administered to a non-human animal with the feedstuff and for this purpose a concentrated feed additive or premix may be prepared for mixing with the normal animal feed.

The compounds of the invention have utility in the control of arthropod pests. They may, in particular, be used in the fields of veterinary medicine, livestock husbandry and the maintenance of public health: against arthropods which are parasitic internally or externally upon vertebrates, particularly warm-blooded vertebrates, including man and domestic animals such as dogs, cats, cattle, sheep, goats, equines, swine, poultry and fish. Also, in the field of control of plant pests, soil inhabiting pests and other environmental pests.

The liquid compositions of this invention may, in addition to normal agricultural use applications be used for example to treat substrates or sites infested or liable to infestation by arthropods (or other pests controlled by compounds of this invention) including premises, outdoor or indoor storage or processing areas, containers or equipment or standing or running water.

All these aqueous dispersions or emulsions or spraying mixtures can be applied, for example, to crops by any suitable means, chiefly by spraying, at rates which are generally of the order of about 100 to about 1,200 liters of spraying mixture per hectare, but may be higher or lower (eg. low or ultra-low volume) depending upon the need or application technique. The compounds or compositions according to the invention are conveniently applied to vegetation and in particular to roots or leaves having pests to be eliminated. Another method of application of the compounds or compositions according to the invention is by chemigation, that is to say, the addition of a formulation containing the active ingredient to irrigation water. This irrigation may be sprinkler irrigation for foliar pesticides or it can be ground irrigation or underground irrigation for soil or for systemic pesticides.

The concentrated suspensions, which can be applied by spraying, are prepared so as to produce a stable fluid product which does not settle (fine grinding) and usually contain from about 10 to about 75% by weight of active ingredient, from about 0.5 to about 30% of surface-active agents, from about 0.1 to about 10% of thixotropic agents, from about 0 to about 30% of suitable additives, such as anti-foaming agents, corrosion inhibitors, stabilizers, penetrating agents, adhesives and, as the carrier, water or an organic liquid in which the active ingredient is poorly soluble or insoluble Some organic solids or inorganic salts may be dissolved in the carrier to help prevent settling or as antifreezes for water.

The wettable powders (or powder for spraying) are usually prepared so that they contain from about 10 to about 80% by weight of active ingredient, from about 20 to about 90% of a solid carrier, from about 0 to about 5% of a wetting agent, from about 3 to about 10% of a dispersing agent and, when necessary, from about 0 to about 80% of one or more stabilizers and/or other additives, such as penetrating agents, adhesives, anti-caking agents, colorants, or the like. To obtain these wettable powders, the active ingredient(s) is(are) thoroughly mixed in a suitable blender with additional substances which may be impregnated on the porous filler and is(are) ground using a mill or other suitable grinder. This produces wettable powders, the wettability and the suspendability of which are advantageous. They may be suspended in water to give any desired concentration and this suspension can be employed very advantageously in particular for application to plant foliage.

The "water dispersible granules (WG)" (granules which are readily dispersible in water) have compositions which are substantially close to that of the wettable powders. They may be prepared by granulation of formulations described for the wettable powders, either by a wet route (contacting finely divided active ingredient with the inert filler and a little water, e.g. 1 to 20% by weight, or with an aqueous solution of a dispersing agent or binder, followed by drying and screening), or by a dry route (compacting followed by grinding and screening).

The rates and concentrations of the formulated compositions may vary according to the method of application or the nature of the compositions or use thereof. Generally speaking, the compositions for application to control arthropod, plant nematode, helminth or protozoan pests usually contain from about 0.00001% to about 95%, more particularly from about 0.0005% to about 50% by weight of one or more compounds of formula (I), or pesticidally acceptable salts thereof, or of total active ingredients (that is to say the compound of formula (I), or a pesticidally acceptable salt thereof, together with: other substances toxic to arthropods or plant nematodes, anthelmintics, anticoccidials, synergists, trace elements or stabilizers). The actual compositions employed and their rate of application will be selected to achieve the desired effect(s) by the farmer, livestock producer, medical or veterinary practitioner, pest control operator or other person skilled in the art.

The compounds of the invention also have utility in the control of arthropod pests of plants. The active compound is generally applied to the locus at which the arthropod infestation is to be controlled at a rate of about 0.005 kg to about 25 kg of active compound per hectare (ha) of locus treated, preferably 0.02 to 2 kg/ha. Under ideal conditions, depending on the pest to be controlled, the lower rate may offer adequate protection. On the other hand, adverse weather conditions and other factors may require that the active ingredient be used in higher proportions. For foliar application, a rate of 0.01 to 1 kg/ha may be used.

Preferably, the locus is the plant surface, or the soil around the plant to be treated.

The compounds of the invention are of particular value in the control of arthropods which are injurious to, or spread or act as vectors of diseases in, man and domestic animals, for example those hereinbefore mentioned, and more especially in the control of ticks, mites, lice, fleas, midges and biting, nuisance and myiasis flies. They are particularly useful in controlling arthropods which are present inside domestic host animals or which feed in or on the skin or suck the blood of the animal, for which purpose they may be administered orally, parenterally, percutaneously or topically.

They are also valuable in the protection of timber (standing, felled, converted, stored or structural) from attack by sawflies or beetles or termites. They have applications in the protectiqn of stored products such as grains, fruits, nuts, spices and tobacco, whether whole, milled or compounded into products, from moth, beetle and mite attack. Also protected are stored animal products such as skins, hair, wool and feathers in natural or converted form (e.g. as carpets or textiles) from moth and beetle attack; also stored meat and fish from beetle, mite and fly attack. Solid or liquid compositions for application topically to timber, stored products or household goods usually contain from about 0.00005% to about 90%, more particularly from about 0.001% to about 10%, by weight of one or more compounds of formula (I) or pesticidally acceptable salts thereof.

The present invention also relates to a method of cleaning animals in good health comprising the application to the animal of compound of formula (I) or a veterinarily acceptable salt. The purpose of such cleaning is to reduce or eliminate the infestation of humans with parasites carried by the animal and to improve the environment which humans inhabit.

The compounds of the invention have utility in the control of arthropod pests. They may, in particular, be used in the fields of veterinary medicine, livestock husbandry and the maintenance of public health: against arthropods which are parasitic internally or externally upon vertebrates, particularly warm-blooded vertebrates, including man and domestic animals such as dogs, cats, cattle, sheep, goats, equines, swine, poultry and fish, for example *Acarina*, including ticks (e.g. *Ixodes* spp., *Boophilus* spp. e.g. *Boophilus microplus*, *Amblyonmma* spp., *Hyalomma* spp., *Rhipicephalus* spp. e.g. *Rhipicephalus appendiculatus*, *Haemaphysalis* spp., *Dermacentor* spp., *Ornithodorus* spp. (e.g. *Omithodorus moubata*), mites (e.g. *Damalinia* spp., *Dermanyssus gallinae*, *Sarcoptes* spp. e.g. *Sarcoptes scabiei*, *Psoroptes* spp., *Chorioptes* spp., *Demodex* spp., *Eutrombicula* spp.); *Diptera* (e.g. *Aedes* spp., *Anopheles* spp., *Muscidae* spp. e.g. *Stomoxys calcitrans* and *Haematobia irritans*, *Hypoderma* spp., *Gastrophilus* spp., *Simulium* spp.); *Hemiptera* (e.g. *Triatoma* spp.); *Phthiraptera* (e.g. *Damalinia* spp., *Linognathus* spp.); *Siphonaptera* (e.g. *Ctenocephalides* spp.); *Dictyoptera* (e.g. *Periplaneta* spp., *Blatella* spp.) and *Hymenoptera* (e.g. *Monomorium pharaonis*);

For the avoidance of doubt, references herein to "treatment" include references to curative, palliative and prophylactic treatment, references to "control" (of parasites and/or pests etc.) include kill, repel, expel, incapacitate, deter, eliminate, alleviate, minimise, eradicate.

The flea membrane feed screen is used to measure the biological activities of the compounds claimed. The assay involves in vitro testing against *Ctenocephalides felis* conducted according to the following general procedure.

Fleas are cultured in vitro using dog blood. 25-30 adult *Ctenocephalides felis* (cat flea) were collected and placed in a test chamber (50 ml polystyrene tube with fine nylon mesh sealing the end). Citrated dog blood was prepared by adding aqueous sodium citrate solution (10 ml, 20% w/v, 20 g sodium citrate in 100 ml water) to dog blood (250 ml). Test compounds were dissolved in dimethylsulfoxide to give a working stock solution of 4 mg/ml. The stock solution (12.5 µl) was added to citrated dog blood (5 ml) to give an initial test concentration of 10 µg/ml. For testing at 30 µg/ml, working stock solutions of 12 mg/ml were prepared. Citrated dog blood containing the test compound (5 ml, 10 µg/ml) was placed into a plastic petri dish lid, which was kept at 37° C on a heated pad. Parafilm was stretched over the open top to form a tight membrane for the fleas to feed through. The test chamber containing the fleas was placed carefully onto the parafilm membrane and the fleas commenced feeding.

The fleas were allowed to feed for 2 hours and the test chambers were then removed and stored overnight at room temperature.

The fleas were observed and the percentage of fleas killed recorded. Compounds active at 10 µg/ml were tested at lower doses. For active molecules, 4 point dose responses (10, 3, 1, 0.3, 0.1 µg/ml) were repeated n=5. Data was plotted to generate ED80 values.

All the exemplified compounds of the present invention which were tested have flea ED80 values less than or equal to 3 in contrast to relevant comparator compounds in the prior art, for example, 3-cyano-5-amino arylpyrazole compounds in which there is a halogen on the 4-cyclopropyl ring described in WO98/24767. For example, 5-amino-3-cyano-4-(2,2-dibromocyclopropyl)-1-(2,6-dichlorophenyl-4-trifluoromethyl-)pyrazole was inactive in the $ED_{80}$ flea screen described above at 30 µg/ml.

In the following experimental details, nuclear magnetic resonance spectral data were obtained using Varian Inova 300, Varian Inova 400, Varian Mercury 400, Varian Unityplus 400, Bruker AC 300 MHz, Bruker AM 250 MHz or Varian T60 MHz spectrometers, the observed chemical shifts being consistent with the proposed structures. Mass spectral data were obtained on a Finnigan Masslab Navigator, a Fisons Instrument Trio 1000, or a Hewlett Packard GCMS System Model 5971 spectrometer. The calculated and observed ions quoted refer to the isotopic composition of lowest mass. HPLC means high performance liquid chromatography. Room temperature means 20 to 25°C.

EXAMPLE 1

5-amino-1-[2,6-dichloro-4-pentafluorothiophenyl]-4-[2,2-difluoro-1-(trifluoromethyl)cyclopropyl]-1H-pyrazole-3-carbonitrile To a solution of Preparation 1 (62 mg, 0.12 mmol) in methanol (10 ml) was added p-toluenesulphonic acid (0.5 g, 2.63 mmol) and the reaction mixture was heated at reflux overnight. The reaction mixture was poured into saturated sodium hydrogen carbonate solution (50 ml) and the resulting mixture was extracted with ethyl acetate (2×20 ml). The combined extracts were dried (MgSO$_4$) and concentrated in vacuo. The crude product was dissolved in acetonitrile (1.5 ml) and water (0.9 ml) and the solution was purified by automated preparative liquid chromatography (Gilson system, 150 mm×30 mm Phenomenex LUNA C18(2) column) using a water:acetonitrile gradient [45:55 to 5:95]. The appropriate fractions were combined and concentrated in vacuo to give racemic title compound (22 mg).

MS (ES): M/Z [MH+] 523.2; expected mass for C14H6Cl2F10N4S+H is 523.0 $^1$H-NMR (CDCl3): 2.05-2.20 (1H), 2.42-2.53 (1H), 3.83-3.99 (2H), 7.87-7.93 (2H)

Racemic Example 1 was dissolved in ethanol/hexane (2:3) and the enantiomers were separated by automated preparative liquid chromatography (Gilson system, 250×20 mm ID Chiralcel OD, 10 µm column) using ethanol/hexane [5:95] as the mobile phase. The appropriate fractions were combined and concentrated to give two enantiomerically enriched products Example 1a and Example 1b.

Example 1a: MS (ES): MH+ 523.0, C14H6Cl2F10N4S+H requires 523.0 HPLC: (Gilson system, 250×20 mm ID Chiralcel OD, 10 µm column), ethanol/hexane [5:95], retention time 10.73 min, enantiomeric purity 100%

Example 1b: MS (ES): MH+ 523.0, C14H6Cl2F10N4S+H requires 523.0 HPLC: (Gilson system, 250×20 mm ID

EXAMPLE 2

5-amino-1-[2,6-dichloro-4-(trifluoromethyl)phenyl]-4-[2,2-difluoro-1-(trifluoromethyl)cyclopropyl]-1H-pyrazole-3-carbonitrile To a solution of Preparation 2 (234 mg, 0.45 mmol) in methanol (10 ml) was added p-toluenesulphonic acid (500 mg, 2.63 mmol) and the reaction mixture was heated at reflux overnight. To the reaction mixture was added ethyl acetate (100 ml) and the organic phase was separated, washed with saturated aqueous sodium hydrogen carbonate solution (2×100 ml), dried ($MgSO_4$) and concentrated in vacuo. The residue was purified by column chromatography (silica, 20 g), eluting with dichloromethane/pentane [2:1]. The appropriate fractions were combined and concentrated to give racemic title compound (160 mg) as a pale yellow solid.

MS (ES): M/Z [MH+] 465.1; expected mass for $C_{15}H_6Cl_2F_8N_4$+H is 465.0 $^1$H-NMR (CDCl3): 2.05-2.20 (1H), 2.42-2.53 (1H), 3.86-3.95 (2H), 7.74-7.79 (2H)

Racemic Example 2 was dissolved in ethanol/hexane (1:1) and the enantiomers were separated by automated preparative liquid chromatography (Gilson system, 250×20 mm ID Chiralcel OD, 10 µm column) using ethanol/hexane [1:9] as the mobile phase. The appropriate fractions were combined and concentrated to give two enantiomerically enriched products Example 2a and Example 2b.

Example 2a: MS (ES): MH$^+$ 464.8, $C_{15}H_6Cl_2F_8N_4$+H requires 465.0 HPLC: (Gilson system, 250×20 mm ID Chiralcel OD, 10 µm column), ethanol/hexane [1:9], retention time 12.09 min, enantiomeric purity 99%, (−) isomer.

Example 2b: MS (ES): MH$^+$ 464.8, $C_{15}H_6Cl_2F_8N_4$+H requires 465.0 HPLC: (Gilson system, 250×20 mm ID Chiralcel OD, 10 µm column), ethanol/hexane [1:9], retention time 14.63 min, enantiomeric purity 100%, (+) isomer.

Similarly prepared were:

EXAMPLE 3

5-amino-1-[2,6-dichloro-4-(trifluoromethyl)phenyl]-4-(1,2,2-trifluorocyclopropyl)-1H-pyrazole-3-carbonitrile; from the compound of Preparation 3 (22 mg, 0.047 mmol) to give the title compound (9.4 mg).

MS (ES): M/Z [MH+] 415.1; expected mass for $C_{14}H_6Cl_2F_6N_4$+H is 415.0 $^1$H-NMR (CDCl3): 2.16-2.27 (2H), 4.02-4.12 (2H), 7.76-7.80 (2H)

EXAMPLE 4

5-amino-1-[2,6-dichloro-4-(trifluoromethyl)phenyl]-4-(pentafluorocyclopropyl)-1H-pyrazole-3-carbonitrile; from the compound of Preparation 4 (32 mg, 0.063 mmol) to give the title compound (10 mg).

MS (ES): M/Z [MH+] 451.1; expected mass for $C_{14}H_4Cl_2F_8N_4$+H is 451.0 $^1$H-NMR (CDCl3): 4.16-4.24 (2H), 7.77-7.81 (2H)

EXAMPLE 5

5-amino4-(2,2-dichloro-1-fluorocyclopropyl)-1-[2,6-dichloro-4-(trifluoromethyl)phenyl]-1H-pyrazole-3-carbonitrile; from the compound of Preparation 5 (29 mg, 0.06 mmol) to give the title compound (5 mg) as a white solid.

MS (ES): M/Z [MH+] 446.8; expected mass for $C_{14}H_6Cl_4F_4N_4$+H is 447.0 $^1$H-NMR (CDCl3): 2.25-2.34 (1H), 2.41-2.47 (1H), 4.09-4.18 (2H), 7.75-7.80 (2H)

EXAMPLE 6

5-amino-1-[2,6-dichloro-4-pentafluorothiophenyl]-4-(pentafluorocyclopropyl)-1H-pyrazole-3-carbonitrile; from the compound of Preparation 6 (40 mg, 0.07 mmol) to give the title compound (20 mg) as a white solid.

MS (ES): M/Z [MH+] 509.2; expected mass for $C_{13}H_4Cl_2F_{10}N_4S$+H is 509.0 $^1$H-NMR (CDCl3): 4.16-4.22 (2H), 7.91-7.93 (2H)

EXAMPLE 7

5-amino-1-[2,6-dichloro-4-pentafluorothiophenyl]-4-(1,2,2-trifluorocyclopropyl)-1H-pyrazole-3-carbonitrile; from the compound of Preparation 7 (92 mg, 0.17 mmol) to give the title compound (46 mg).

MS (ES): M/Z [MH+] 472.9; expected mass for $C_{13}H_6Cl_2F_8N_4S$+H is 473.0 $^1$H-NMR (CDCl3): 2.14-2.27 (2H), 4.05-4.14 (2H), 7.89-7.92 (2H)

EXAMPLE 8

5-amino-1-[2,6-dichloro-4-(trifluoromethyl)phenyl]-4-[1-(difluoromethyl)-2,2-difluorocyclopropyl]-1H-pyrazole-3-carbonitrile To a solution of Preparation 23 (4.0 g, 8.0 mmol) in 1,4-dioxane (50 ml) was added methanol (5 ml) and hydrochloric acid (10% in water, 5 ml). The reaction mixture was then heated at reflux for 4 h.

To the reaction mixture was added saturated aqueous sodium hydrogen carbonate solution and the aqueous phase was separated and extracted with ethyl acetate (3×20 ml). The combined organic phases were then dried ($MgSO_4$) and concentrated in vacuo. The residue was purified by column chromatography (silica, 70 g) with gradient elution, petroleum ether:diethyl ether [1:0 to 0:1]. The appropriate fractions were combined and concentrated to give racemic Example 8 (3.2 g).

MS (ES): M/Z [MH+] 448.9; expected mass for $C_{15}H_7Cl_2F_7N_4$+H is 447.0 $^1$H-NMR (CDCl3): 2.04-2.11 (1H), 2.13-2.20 (1H), 3.82-3.90 (2H), 5.63-5.89 (1H), 7.73-7.79 (2H)

Racemic Example 8 (88 mg) was dissolved in ethanol/hexane (1:1) and the enantiomers were separated by automated preparative liquid chromatography (Gilson system, 250×20 mm ID Chiralcel OD, 10 µm column) using ethanol/hexane [2:8] as the mobile phase. The appropriate fractions were combined and concentrated to give Example 8a (40 mg) and Example 8b (40 mg).

Example 8a: MS (ES): MH$^+$ 446.8, $C_{15}H_7Cl_2F_7N_4$+H requires 447.0 HPLC: (Gilson system, 250×20 mm ID Chiralcel OD, 10 µm column), ethanol/hexane [2:8], retention time 7.3 min, enantiomeric purity 100%.

Example 8b: MS (ES): MH$^+$ 446.8, $C_{15}H_7Cl_2F_7N_4$+H requires 447.0 HPLC: (Gilson system, 250×20 mm ID Chiralcel OD, 10 µm column), ethanol/hexane [2:8], retention time 17.4 min, enantiomeric purity 100%.

EXAMPLE 9

5-amino-1-[2,6-dichloro-4-(trifluoromethyl)phenyl]-4-(2,2-difluorocyclopropyl)-1H-pyrazole-3-carbonitrile To a solution of Preparation 31 (560 mg, 1.40 mmol) and sodium fluoride (4.0 mg, 0.12 mmol) in toluene (0.8 ml), at 100° C., was added trimethylsilyl-2,2-difluoro-2-(fluorosulphonyl)acetate (700 mg, 2.8 mmol) over a period of 1 h, using a syringe. The reaction mixture was then heated at reflux for 1 h.

To the cooled reaction mixture was added silica and the solution was concentrated in vacuo. The product/silica mix was partially purified by column chromatography, eluting with diethyl ether/hexane [1:1], and the product-containing fractions were concentrated in vacuo. To the residue was added methanol (5 ml) and hydrochloric acid (2N, 5 ml) and the reaction mixture was heated at reflux for 6 h. The reaction mixture was concentrated in vacuo and the residue partitioned between diethyl ether and water (20 ml). The two layers were separated and the organic layer dried ($MgSO_4$) and concentrated in vacuo.

The residue was purified by column chromatography with gradient elution, diethyl ether:hexane [1:2 to 1:1]. The appropriate fractions were combined and concentrated to give Example 9 (96 mg) as a white solid.

MS (ES): M/Z [MH+] 397.1; expected mass for $C14H7Cl2F5N4+H$ is 397.0 $^1$H-NMR (CDCl3): 1.74-1.83 (1H), 1.95-2.05 (1H), 2.44-2.56 (1H), 3.72-3.84 (2H), 7.76-7.81 (2H)

Similarly prepared to Example 2 was:

EXAMPLE 10

5-amino-4-[2,2-difluoro-1-(trifluoromethyl)cyclopropyl]-1-[2,6-difluoro-4-(trifluoromethyl)phenyl]-1H-pyrazole-3-carbonitrile; from the compound of Preparation 10 (250 mg, 0.51 mmol) to give the title compound (11 mg).

MS (ES): M/Z [MH+] 433.0; expected mass for $C15H6F10N4+H$ is 433.1 $^1$H-NMR (CDCl3): 2.02-2.09 (2H), 2.29-2.42 (1H), 4.63-4.76 (1H), 7.30-7.37 (2H), Similarly prepared to Example 8 were:

EXAMPLE 11

5-amino-1-[2,6-dichloro-4-pentafluorothiophenyl]-4-[1-(difluoromethyl)-2,2-difluorocyclopropyl]-1H-pyrazole-3-carbonitrile; from the compound of Preparation 11 (655 mg, 1.17 mmol) to give the racemic title compound (284 mg).

MS (ES): M/Z [MH+] 504.9; expected mass for $C14H7Cl2F9N4S+H$ is 505.0 $^1$H-NMR (CDCl3): 2.00-2.09 (1H), 2.12-2.20 (1H), 3.87-3.96 (2H), 5.61-5.90 (1H), 7.88-7.91 (2H)

Racemic Example 11 was dissolved in ethanol/hexane (1:1) and the enantiomers were separated by automated preparative liquid chromatography (Gilson system, 250×20 mm ID Chiralcel OD, 10 µm column) using ethanol/hexane [2:8] as the mobile phase. The appropriate fractions were combined and concentrated to give two enantiomerically enriched products Example 11a and Example 11b.

Example 11a: MS (ES): MH+ 504.9, $C14H7Cl2F9N4S+H$ requires 505.0 HPLC: (Gilson system, 250×20 mm ID Chiralcel OD, 10 µm column), ethanol/hexane [2:8], retention time 6.40 min, enantiomeric purity 100%

Example 11b: MS (ES): MH+ 504.9, $C14H7Cl2F9N4S+H$ requires 505.0 HPLC: (Gilson system, 250×20 mm ID Chiralcel OD, 10 µm column), ethanol/hexane [2:8], retention time 13.89 min, enantiomeric purity 100%

EXAMPLE 12

5-amino4-{1-[chloro(fluoro)methyl]-2,2-difluorocyclopropyl}-1-[2,6-dichloro-4-(trifluoromethyl)phenyl]-1H-pyrazole-3-carbonitrile; from the compound of Preparation 12 (100 mg, 0.19 mmol) to give racemic title compound (20 mg).

MS (ES): M/Z [MH+] 462.8; expected mass for $C15H7Cl3F6N4+H$ is 463.0 $^1$H-NMR (CDCl3): 2.03-2.11 (1H), 2.16-2.25 (1H), 3.84-3.95 (2H), 6.02-6.16 (1H), 7.73-7.80 (2H)

Racemic Example 12 was dissolved in ethanol/hexane (1:1) and the enantiomers were separated by automated preparative liquid chromatography (Gilson system, 250×20 mm ID Chiralcel OD, 10 µm column) using ethanol/hexane [2:8] as the mobile phase. The appropriate fractions were combined and concentrated to give two enantiomerically enriched products Example 12a and Example 12b.

Example 12a: MS (ES): MH+ 462.9, $C15H7Cl3F6N4+H$ requires 463.0 HPLC: (Gilson system, 250×20 mm ID Chiralcel OD, 10 µm column), ethanol/hexane [2:8], retention time 7.07 min, enantiomeric purity 99%

Example 12b: MS (ES): MH+ 462.9, $C15H7Cl3F6N4+H$ requires 463.0 HPLC: (Gilson system, 250×20 mm ID Chiralcel OD, 10 µm column), ethanol/hexane [2:8], retention time 21.44 min, enantiomeric purity 100%

EXAMPLE 13

5-amino-1-[2,6-dichloro-4-(trifluoromethyl)phenyl]-4-[1-(difluoromethyl)-2,2,3,3-tetrafluorocyclopropyl]-1H-pyrazole-3-carbonitrile; from the compound of Preparation 13 (48 mg, 0.09 mmol) to give the title compound (17 mg).

MS (ES): M/Z [MH+] 482.7; expected mass for $C15H5Cl2F9N4+H$ is 483.0 $^1$H-NMR (CDCl3): 3.84-3.91 (2H), 5.95-6.24 (1H), 7.76-7.79 (2H)

EXAMPLE 14

5-amino-1-[2,6-dichloro-4-(trifluoromethyl)phenyl]-4-[2,2,3,3-tetrafluoro-1-(trifluoromethyl)cyclopropyl]-1H-pyrazole-3-carbonitrile; from the compound of Preparation 14 (7 mg, 0.01 mmol) to give the title compound (4 mg).

MS (ES): M/Z [MH+] 500.9; expected mass for $C15H4Cl2F10N4+H$ is 501.0

EXAMPLE 15

1-[2,6-dichloro4-(trifluoromethyl)phenyl]-4-[2,2-difluoro-1-(trifluoromethyl)cyclopropyl]-5-(methylamino)-1H-pyrazole-3-carbonitrile To a solution of Example 2 (500 mg, 1.08 mmol) in triethyl orthoformate (13.4 ml) was added concentrated hydrochloric acid (few drops). The reaction mixture was then heated at reflux for 2.5 h. The reaction mixture was concentrated in vacuo and the residue was re-dissolved in toluene and re-concentrated (×2). To a solution of the residue in ethanol (10 ml), at 0° C., was added sodium borohydride (90 mg, 2.37 mmol). The reaction mixture was then stirred at room temperature overnight. To the reaction mixture was added acetic acid (0.5 ml) and water (10 ml) and the mixture was extracted with ethyl acetate (3×10 ml). The combined organic phases were dried ($MgSO_4$) and concentrated in vacuo. The residue was purified by column chromatography (silica), loading on in toluene and eluting with toluene. The appropriate fractions were combined and concentrated to give racemic Example 15 (323 mg).

MS (ES): M/Z [MH+] 478.8; expected mass for $C16H8Cl2F8N4+H$ is 479.0 $^1$H-NMR (CDCl3): 2.07-2.23 (1H), 2.42-2.58 (1H), 2.71-2.76 (3H), 3.51-3.66 (1H), 7.73-7.77 (2H)

Racemic Example 15 was dissolved in ethanol/hexane (1:1) and the enantiomers were separated by automated preparative liquid chromatography (Gilson system, 250×20 mm ID Chiralcel OD, 10 µm column) using ethanol/hexane [1:9] as the mobile phase. The appropriate fractions were combined and concentrated to give two enantiomerically enriched products Example 15a and Example 15b.

Example 15a: MS (ES): MH+ 478.9, C16H8Cl2F8N4+H requires 479.0 HPLC: (Gilson system, 250×20 mm ID Chiralcel OD, 10 µm column), ethanol/hexane [1:9], retention time 8.67 min, enantiomeric purity 100%

Example 15b: MS (ES): MH+ 478.9, C16H8Cl2F8N4+H requires 479.0 HPLC: (Gilson system, 250×20 mm ID Chiralcel OD, 10 µm column), ethanol/hexane [1:9], retention time 11.26 min, enantiomeric purity 100%

Similarly prepared to Example 8 were:

EXAMPLE 16

5-amino-1-[2,6-dichloro-4-(trifluoromethoxy)phenyl]-4-[2,2-difluoro-1-(trifluoromethyl)cyclopropyl]-1H-pyrazole-3-carbonitrile; from the compound of Preparation 15 (1.0 g, 1.86 mmol) to give the racemic title compound (630 mg).

MS (ES): M/Z [MH+] 480.9; expected mass for C15H6Cl2F8N4O+H is 481.0 $^1$H-NMR (CDCl3): 2.05-2.18 (1H), 2.41-2.52 (1H), 3.87-3.95 (2H), 7.37-7.40 (2H)

Racemic Example 16 was dissolved in ethanol/hexane (1:1) and the enantiomers were separated by automated preparative liquid chromatography (Gilson system, 250×20 mm ID Chiralcel OD, 10 µm column) using ethanol/hexane [5:95] as the mobile phase. The appropriate fractions were combined and concentrated to give two enantiomerically enriched products Example 16a and Example 16b.

Example 16a: MS (ES): MH+ 480.9, C15H6Cl2F8N4O+H requires 481.0 HPLC: (Gilson system, 250×20 mm ID Chiralcel OD, 10 µm column), ethanol/hexane [5:95], retention time 8.86 min, enantiomeric purity 99%

Example 16b: MS (ES): MH+ 480.9, C15H6Cl2F8N4O+H requires 481.0 HPLC: (Gilson system, 250×20 mm ID Chiralcel OD, 10 µm column), ethanol/hexane [5:95], retention time 9.91 min, enantiomeric purity 100%

EXAMPLE 17

5-amino-1-[2,6-dichloro-4-(trifluoromethoxy)phenyl]-4-[1-(difluoromethyl)-2,2,3,3-tetrafluorocyclopropyl]-1H-pyrazole-3-carbonitrile; from the compound of Preparation 16 (50 mg, 0.09 mmol) to give the title compound (10 mg).

MS (ES): M/Z [MH+] 498.9; expected mass for C15H5Cl2F9N4O+H is 499.0 $^1$H-NMR (CDCl3): 3.86-3.91 (2H), 5.95-6.23 (1H), 7.38-7.40 (2H)

EXAMPLE 18

5-amino-1-[2,6-dichloro-4-(trifluoromethoxy)phenyl]-4-[1-(difluoromethyl)-2,2-difluorocyclopropyl]-1H-pyrazole-3-carbonitrile; from the compound of Preparation 17 (3.6 g, 7.0 mmol) to give the racemic title compound (3.0 g).

MS (ES): M/Z [MH+] 463.0; expected mass for C15H7Cl2F7N4O+H is 463.0 $^1$H-NMR (CDCl3): 2.00-2.08 (1H), 2.10-2.19 (1H), 3.82-4.00 (2H), 5.60-5.90 (1H), 7.35-7.40 (2H)

Racemic Example 18 was dissolved in ethanol/hexane (1:2) and the enantiomers were separated by automated preparative liquid chromatography (Gilson system, 250×20 mm ID Chiralcel OD, 10 µm column) using ethanol/hexane [1:9] as the mobile phase. The appropriate fractions were combined and concentrated to give two enantiomerically enriched products Example 18a and Example 18b.

Example 18a: MS (ES): MH+ 463.0, C15H7Cl2F7N4O+H requires 463.0 HPLC: (Gilson system, 250×20 mm ID Chiralcel OD, 10 µm column), ethanol/hexane [1:9], retention time 13.35 min, enantiomeric purity 99%

Example 18b: MS (ES): MH+ 463.0, C15H7Cl2F7N4O+H requires 463.0 HPLC: (Gilson system, 250×20 mm ID Chiralcel OD, 10 µm column), ethanol/hexane [1:9], retention time 31.58 min, enantiomeric purity 100%

EXAMPLE 19

5-amino-1-[2,6-dichloro-4-(trifluoromethyl)phenyl]-4-[2,2-difluoro-1-(fluoromethyl)cyclopropyl]-1H-pyrazole-3-carbonitrile; from the compound of Preparation 18 (100 mg, 0.21 mmol) to give the racemic title compound (17 mg).

MS (ES): M/Z [MH+] 428.9; expected mass for C15H8Cl2F6N4+H is 429.0 $^1$H-NMR (CDCl3): 1.84-1.93 (1H), 1.93-2.02 (1H), 3.68-4.06 (2H), 4.42-4.82 (2H), 7.73-7.78 (2H)

Racemic Example 19 was dissolved in ethanol/hexane (1:1) and the enantiomers were separated by automated preparative liquid chromatography (Gilson system, 250×20 mm ID Chiralcel OD, 10 µm column) using ethanol/hexane [1:9] as the mobile phase. The appropriate fractions were combined and concentrated to give two enantiomerically enriched products Example 19a and Example 19b.

Example 19a: MS (ES): MH+ 429.0, C15H8Cl2F6N4+H requires 429.0 HPLC: (Gilson system, 250×20 mm ID Chiralcel OD, 10 µm column), ethanol/hexane [1:9], retention time 14.99 min, enantiomeric purity 100%

Example 19b: MS (ES): MH+ 429.0, C15H8Cl2F6N4+H requires 429.01 HPLC: (Gilson system, 250×20 mm ID Chiralcel OD, 10 µm column), ethanol/hexane [1:9], retention time 20.89 min, enantiomeric purity 100%

EXAMPLE 20

5-amino-1-[2,6-dichloro-4-(trifluoromethyl)phenyl]-4-(2,2-difluoro-1-methylcyclopropyl)-1H-pyrazole-3-carbonitrile; from the compound of Preparation 19 (80 mg, 0.17 mmol) to give the title compound (56 mg).

MS (ES): M/Z [MH+] 411.0; expected mass for C15H9Cl2F5N4+H is 411.0 $^1$H-NMR (CDCl3): 1.46-1.50 (3H), 1.56-1.63 (1H), 1.69-1.78 (1H), 3.62-3.76 (2H), 7.72-7.77 (2H)

EXAMPLE 21

5-amino-1-{2,6-dichloro-4-[(trifluoromethyl)thio]phenyl}-4-[2,2-difluoro-1-(trifluoromethyl)cyclopropyl]-1H-pyrazole-3-carbonitrile; from the compound of Preparation 20 (1.8 g, 3.3 mmol to give the title compound (1.1 g).

MS (ES): M/Z [MH+] 496.9; expected mass for C15H6Cl2F8N4S+H is 496.9 $^1$H-NMR (CDCl3): 2.05-2.18 (1H), 2.42-2.52 (1H), 3.86-3.97 (2H), 7.75-7.80 (2H)

EXAMPLE 22 ethyl 3-cyano-1-[2,6-dichloro-4-(trifluoromethyl)phenyl]-4-[2,2-difluoro-1-(trifluoromethyl)cyclopropyl]-1H-pyrazol-5-ylcarbamate To a solution of Example 2a (100 mg, 0.20 mmol) in N,N-dimethylformamide (3 ml) was added sodium hydride (10 mg, 0.20 mmol), followed by 1-chloroethyl ethyl carbonate (37 mg, 0.24 mmol). The reaction mixture was then stirred at room temperature overnight. The reaction mixture was concentrated in vacuo and the residue was dissolved in acetonitrile (2 ml). The solution was purified by automated preparative liquid chromatography (Gilson system, 150 mm×30 mm LUNA II C18 10 μm column) using an acetonitrile:water gradient [60:40 to 95:5]. The appropriate fractions were combined and concentrated to give Example 22 (50 mg).

MS (ES): M/Z [MH+] 536.9; expected mass for C18H10Cl2F8N4O2+H is 537.0 $^1$H-NMR (CDCl3): 1.07-1.14 (3H), 2.09-2.19 (1H), 2.48-2.57 (1H), 3.99-4.06 (2H), 6.16-6.24 (1H), 7.71-7.76 (2H)

Similarly prepared was:

EXAMPLE 23

1-[2,6-dichloro-4-(trifluoromethyl)phenyl]-4-[2,2-difluoro-1-(trifluoromethyl)cyclopropyl]-5-(2-oxo-1,3-oxazolidin-3-yl)-1H-pyrazole-3-carbonitrile; from the compound of Example 2a (135 mg, 0.30 mmol) and 2-bromoethyl chloroformate (60 mg, 0.33 mmol) to give the title compound (47 mg).

MS (ES): M/Z [MH+] 534.9; expected mass for C18H8Cl2F8N4O2+H is 535.0 $^1$H-NMR (CDCl3): 2.31-2.39 (1H), 2.54-2.64 (1H), 4.00-4.10 (2H), 4.43-4.50 (2H), 7.75-7.78 (2H)

Similarly preared to Example 8 was:

EXAMPLE 24

5-amino-1-[3-chloro-5-(trifluoromethyl)pyridin-2-yl]-4-[2,2-difluoro-1-(trifluoromethyl)cyclopropyl]-1H-pyrazole-3-carbonitrile; from the compound of Preparation 22 (164 mg, 0.34 mmol to give the title compound (60 mg).

MS (ES): M/Z [MH+] 432.0; expected mass for C14H6ClF8N5+H is 432.0 $^1$H-NMR (CDCl3): 2.02-2.19 (1H), 2.40-2.54 (1H), 5.13-5.22 (2H), 8.19-8.23 (1H), 8.63-8.67 (1H)

EXAMPLE 25

Hydrochloride salt of 2-(dimethylamino)ethyl 3-cyano-1-[2,6-dichloro-4-(trifluoromethyl)phenyl]-4-[2,2-difluoro-1-(trifluoromethyl)cyclopropyl]-1H-pyrazol-5-ylcarbamate To a solution of Example 2a (100 mg, 0.22 mmol) in anhydrous dichloromethane/toluene (3:2, 2 ml) was added pyridine (40 μl, 0.50 mmol) and molecular sieves (4A). This solution was added to phosgene (20% in toluene, 1.7N, 300 μl, 0.50 mmol), at 0° C. and under nitrogen, and the reaction mixture was allowed to stand for 1 h. 2-(dimethylamino) ethanol (1 ml) was added and the reaction mixture was allowed to stand overnight before being concentrated in vacuo. The residue was dissolved in acetonitrile (1.8 ml) and the solution was purified by automated preparative liquid chromatography (Gilson system, 150 mm×30 mm LUNA II C18 10 μm column) using an acetonitrile: 0.1% trifluoroacetic acid gradient [35:65 to 95:5]. The appropriate fractions were combined and concentrated and to the residue was added hydrochloric acid to give Example 25 (100 mg).

MS (ES): M/Z [MH+] 580.0; expected mass for C20H15Cl2F8N5O2+H is 580.1 $^1$H-NMR (CDCl3): 2.21-2.30 (1H), 2.47-2.56 (2H), 2.84-2.88 (6H), 3.19-3.24 (2H), 4.27-4.39 (2H), 7.71-7.74 (2H)

Similarly prepared was:

EXAMPLE 26

2,2,2-trifluoroethyl 3-cyano-1-[2,6-dichloro-4-(trifluoromethyl)phenyl]-4-[2,2-difluoro-1-(trifluoromethyl)cyclopropyl]-1H-pyrazol-5-ylcarbamate; from the compound of Example 2a (100 mg, 0.22 mmol) and 2,2,2-trifluoroethanol to give the title compound (100 mg).

MS (ES): M/Z [MH+] 590.9; expected mass for C18H7Cl2F11N4O2+H is 591.0 $^1$H-NMR (DMSO): 2.61-2.71 (1H), 2.89-2.99 (1H), 4.62-4.73 (2H), 8.26-8.29 (2H), 10.89-10.97 (1H)

EXAMPLE 27

5-amino-1-{2,6-dichloro-4-[(trifluoromethyl)sulfonyl]phenyl}-4-[2,2-difluoro-1-(trifluoromethyl)cyclopropyl]-1H-pyrazole-3-carbonitrile A mixture of Example 21 (600 mg, 1.2 mmol) and 3-chloroperoxybenzoic acid (929 mg, 5.4 mmol) in dichloromethane (20 ml) was stirred at room temperature for 48 h. The reaction mixture was washed with aqueous sodium hydroxide solution, followed by water and brine. The organic phase was then dried and concentrated in vacuo. The residue was purified by flash chromatography (silica) with gradient elution, toluene:dichloromethane [1:0 to 0:1]. The appropriate fractions were combined and concentrated in vacuo. The residue was dissolved in acetonitrile/water (1 ml) and the solution was purified by automated preparative liquid chromatography (Gilson system, 150 mm×30 mm LUNA II C18 10 μm column) using an acetonitrile:water gradient [60:40 to 95:5]. The appropriate fractions were combined and concentrated to give Example 27 (27 mg).

MS (ES): M/Z [MH+] 529.0; expected mass for C15H6Cl2F8N4O2S+H is 529.0 $^1$H-NMR (DMSO): 2.11-2.22 (1H), 2.59-2.70 (1H), 6.68-6.73 (2H), 8.55-8.59 (2H)

EXAMPLE 28

1-[2,6-dichloro-4-(trifluoromethyl)phenyl]-4-[2,2-difluoro-1-(trifluoromethyl)cyclopropyl]-5-[(pyridin-4-ylmethyl)amino]-1H-pyrazole-3-carbonitrile To a solution of Preparation 25 (200 mg, 0.36 mmol) in anhydrous methanol (10 ml), under nitrogen and at 0° C., was added sodium borohydride (34 mg, 0.90 mmol). The reaction mixture was then stirred at room temperature for 2 h. To the reaction mixture was added water and the mixture was adjusted to pH 2 by addition of hydrochloric acid (4N). The mixture was then neutralised by addition of saturated aqueous sodium carbonate solution, extracted with ethyl acetate (3×10 ml) and the combined extracts dried (MgSO$_4$) and concentrated in vacuo. The residue was dissolved in acetonitrile/water (3.6 ml) and the solution was purified by automated preparative liquid chromatography (Gilson system, 150×30 mm, LUNA II C18 10 μm column) using an acetonitrile:water gradient [55:45 to 95:5]. The appropriate fractions were concentrated to give Example 28 (34 mg).

MS (ES): M/Z [MH+] 556.0; expected mass for C21H11Cl2F8N5+H is 556.0 $^1$H-NMR (CDCl3): 2.20-2.34 (1H), 2.53-2.67 (1H), 4.10-4.17 (1H), 4.18-4.28 (2H), 7.01-7.05 (2H), 7.60-7.63 (2H), 8.44-8.48 (2H)

Similarly prepared to Example 2 were:

EXAMPLE 29

5-amino-1-[2,6-dichloro-4-(difluoromethoxy)phenyl]-4-[2,2-difluoro-1-(trifluoromethyl)cyclopropyl]-1H-pyrazole-3-carbonitrile; from the compound of Preparation 26 (110 mg, 0.21 mmol) to give the title compound (48 mg).

MS (ES): M/Z [MH+] 463.0; expected mass for C15H7Cl2F7N4O+H is 463.0 $^1$H-NMR (CDCl3): 2.01-2.19 (1H), 2.38-2.51 (1H), 3.83-3.98 (2H), 6.38-6.77 (1H), 7.27-7.32 (2H)

EXAMPLE 30

5-amino-1-[2,6-dichloro-4-pentafluorothiophenyl]-4-[1-(difluoromethyl)-2,2,3,3-tetrafluorocyclopropyl]-1H-pyrazole-3-carbonitrile; from the compound of Preparation 27 (138 mg, 0.23 mmol) to give the title compound (100 mg).

MS (ES): M/Z [MH+] 541.0; expected mass for C14H5Cl2F11N4S+H is 541.0 $^1$H-NMR (DMSO): 6.51-6.71 (1H), 6.73-6.76 (2H), 8.43-8.46 (2H)

Similarly prepared to Example 25 were:

EXAMPLE 31

Isopropyl 3-cyano-1-[2,6-dichloro-4-(trifluoromethyl)phenyl]-4-[2,2-difluoro-1-(trifluoromethyl)cyclopropyl]-1H-pyrazol-5-ylcarbamate; from the compound of Example 2a (50 mg, 0.11 mmol) and 2-propanol to give the title compound (44 mg).

MS (ES): M/Z [MH+] 551.0; expected mass for C19H12Cl2F8N4O2+H is 551.0 $^1$H-NMR (DMSO): 0.96-1.04 (6H), 2.61-2.71 (1H), 2.87-2.99 (1H), 4.59-4.67 (1H), 8.28-8.32 (2H), 10.15-10.22 (1H)

EXAMPLE 32

Hydrochloride salt of pyridin-4-ylmethyl 3-cyano-1-[2,6-dichloro-4-(trifluoromethyl)phenyl]-4-[2,2-difluoro-1-(trifluoromethyl)cyclopropyl]-1H-pyrazol-5-ylcarbamate; from the compound of Example 2a (50 mg, 0.11 mmol) and pyridine-4-methanol to give the title compound (5 mg).

MS (ES): M/Z [MH+] 600.0; expected mass for C22H11Cl2F8N5O2+H is 600.0 $^1$H-NMR (CD3OD): 2.24-2.35 (1H), 2.55-2.65 (1H), 5.21-5.23 (2H), 7.65-7.68 (2H), 7.92-7.94 (2H), 8.64-8.68 (2H)

EXAMPLE 33

Hydrochloride salt of pyridin-3-ylmethyl 3-cyano-1-[2,6-dichloro-4-(trifluoromethyl)phenyl]-4-[2,2-difluoro-1-(trifluoromethyl)cyclopropyl]-1H-pyrazol-5-yl]-carbamate; from the compound of Example 2a (50 mg, 0.11 mmol) and pyridine-3-methanol to give the title compound (24 mg).

MS (ES): M/Z [MH+] 600.0; expected mass for C22H11Cl2F8N5O2+H is 600.0 $^1$H-NMR (DMSO): 2.63-2.73 (1H), 2.84-2.95 (1H), 5.11-5.16 (2H), 7.68-7.74 (1H), 7.95-8.01 (1H), 8.20-8.26 (2H), 8.61-8.64 (1H), 8.68-8.73 (1H),

EXAMPLE 34

Hydrochloride salt of pyridin-2-ylmethyl 3-cyano-1-[2,6-dichloro-4-(trifluoromethyl)phenyl]-4-[2,2-difluoro-1-(trifluoromethyl)cyclopropyl]-1H-pyrazol-5-ylcarbamate; from the compound of Example 2a (50 mg, 0.11 mmol) and pyridine-2-methanol to give the title compound (31 mg).

MS (ES): M/Z [MH+] 600.0; expected mass for C22H11Cl2F8N5O2+H is 600.0 $^1$H-NMR (DMSO): 2.65-2.75 (1H), 2.86-2.97 (1H), 5.05-5.11 (2H), 7.11-7.16 (1H), 7.31-7.37 (1H), 7.77-7.82 (1H), 8.21-8.28 (2H), 8.46-8.51 (1H), 10.56-10.70 (1H),

EXAMPLE 35

Hydrochloride salt of 1H-imidazol-5-ylmethyl 3-cyano-1-[2,6-dichloro-4-(trifluoromethyl)phenyl]-4-[2,2-difluoro-1-(trifluoromethyl)cyclopropyl]-1H-pyrazol-5-ylcarbamate; from the compound of Example 2a (50 mg, 0.11 mmol) and 5-(hydroxymethyl)imidazole to give the title compound (2 mg).

MS (ES): M/Z [MH+] 589.0; expected mass for C20H10Cl2F8N6O2+H is 589.0

EXAMPLE 36

Hydrochloride salt of 2-pyrrolidin-1-ylethyl 3-cyano-1-[2,6-dichloro-4-(trifluoromethyl)phenyl]-4-[2,2-difluoro-1-(trifluoromethyl)cyclopropyl]-1H-pyrazol-5-ylcarbamate; from the compound of Example 2a (50 mg, 0.11 mmol) and 1-(2-hydroxyethyl)pyridine to give the title compound (10 mg).

MS (ES): M/Z [MH+] 606.1; expected mass for C22H17Cl2F8N5O2+H is 606.1 $^1$H-NMR (CD3OD): 1.93-2.01 (4H), 2.31-2.38 (1H), 2.56-2.64 (1H), 3.18-3.23 (4H), 3.30-3.35 (2H), 4.21-4.26 (2H), 7.95-7.99 (2H)

Similarly prepared to Example 8 was:

EXAMPLE 37

5-amino-4-{1-[chloro(difluoro)methyl]-2,2-difluorocyclopropyl}-1-[2,6-dichloro-4-(trifluoromethyl)phenyl]-1H-pyrazole-3-carbonitrile; from a compound of Preparation 55 (124 mg, 0.23 mmol) to give the title compound (17 mg).

MS (ES): M/Z [MH+] 480.9; expected mass for C15H6Cl3F7N4+H is 480.96 $^1$H-NMR (CDCl3): 2.08-2.24 (1H), 2.46-2.61 (1H), 3.87-4.00 (2H), 7.75-7.79 (2H), Racemic Example 37 was dissolved in ethanol/hexane (1:4) and the enantiomers were separated by automated preparative liquid chromatography (Gilson system, 250×20 mm ID Chiralcel IA, 5 µm column) using ethanol/hexane [5:95] as the mobile phase. The appropriate fractions were combined and concentrated to give one enantiomerically pure product, Example 37a, and several mixed fractions.

Example 37a: MS (ES): MH+ 481.0, C15H6Cl3F7N4+H requires 481.0 HPLC: (Gilson system, 250×20 mm ID Chiralcel OD, 10 µm column), ethanol/hexane [5:95], retention time 10.55 min, enantiomeric purity 98%.

The following Preparations illustrate the synthesis of certain intermediates used in the preparation of the preceding Examples.

Preparation 1

N'-{3-cyano-1-[2,6-dichloro-4-(pentafluorothio)phenyl]-4-[2,2-difluoro-1-(trifluoromethyl)cyclopropyl]-1H-pyrazol-5-yl}-N,N-dimethylimidoformamide A mixture of Preparation 32 (264 mg, 0.5 mmol), methyl benzoate (100 µl) and sodium fluoride (6 mg) was heated at 105° C. under nitrogen. Trimethylsilyl-2,2-difluoro-2-(fluorosulphonyl)acetate (197 µl, 1.0 mmol) was added dropwise over 1 h and the reaction mixture was stirred at 105° C. Further trimethylsilyl-2,2-difluoro-2-(fluorosulphonyl)acetate (700 µl, 3.6 mmol) was added over 7 h, maintaining the temperature of the reaction mixture at 105° C. To the reaction mixture was added dichloromethane (15 ml) and the solution was washed with saturated aqueous sodium hydrogen carbonate. The organic phase was separated, dried (MgSO$_4$) and concentrated in vacuo. The residue was purified using an Isolute™ cartridge (silica, 20 g), eluting with toluene. The appropriate fractions were combined and concentrated to give Preparation 1 (62 mg) as an off-white solid.

MS (ES): M/Z [MH+] 578.3; expected mass for C17H11Cl2F10N5S+H is 578.0 $^1$H-NMR (CDCl3): 2.15-

2.20 (1H), 2.45-2.55 (1H), 2.79-2.81 (3H), 3.01-3.03 (3H), 7.79-7.81 (2H), 7.88-7.90 (1H)

Similarly prepared was:

Preparation 2

N'-{3-cyano-1-[2,6-dichloro-4-(trifluoromethyl)phenyl]-4-[2,2-difluoro-1-(trifluoromethyl)cyclopropyl]-1H-pyrazol-5-yl}-N,N-dimethylimidoformamide; from the compound of Preparation 33 (160 mg, 0.34 mmol) to give the title compound (94 mg) as a pale yellow solid.

MS (ES): M/Z [MH+] 520.2; expected mass for C18H11Cl2F8N5+H is 520.0 $^1$H-NMR (CDCl3): 1.99-2.31 (2H), 2.74-2.80 (3H), 2.99-3.00 (3H), 7.64-7.69 (2H), 7.82-8.02 (1H)

Preparation 3

N'-{3-cyano-1-[2,6-dichloro-4-(trifluoromethyl)phenyl]-4-[(1R)-1,2,2-trifluorocyclopropyl]-1H-pyrazol-5-yl}-N,N-dimethylimidoformamide To a solution of Preparation 34 (11 mg, 0.026 mmol) in toluene (0.2 ml), under nitrogen, was added phenyl-(trifluoromethyl)-mercury (45 mg, 0.13 mmol) and sodium iodide (59 mg, 0.39 mmol). The reaction mixture was then heated at 85° C. for 18 h. To the reaction mixture was added toluene (5 ml) and the solution was filtered through Arbocel, to remove any Hg residues. The filtrate was concentrated in vacuo to give Preparation 3 (22 mg). MS (ES): M/Z [MH+] 470.2; expected mass for C17H11Cl2F6N5+H is 470.0 $^1$H-NMR (CDCl3): 2.08-2.31 (2H), 2.81-2.84 (3H), 3.04-3.08 (3H), 7.65-7.69 (2H), 7.85-7.88 (1H)

Similarly prepared were:

Preparation 4

N'-[3-cyano-1-[2,6-dichloro-4-(trifluoromethyl)phenyl]-4-(pentafluorocyclopropyl)-1-H-pyrazol-5-yl]-N,N-dimethylimidoformamide; from the compound of Preparation 35 (46 mg, 0.1 mmol) to give the title compound (35 mg) as a white solid.

MS (ES): M/Z [MH+] 506.2; expected mass for C17H9Cl2F8N5+H is 506.0 $^1$H-NMR (CDCl3): 2.85-2.87 (3H), 3.07-3.09 (3H), 7.67-7.69 (2H), 7.69-7.71 (1H),

Preparation 5

N'-{3-cyano-4-(2,2-dichloro-1-fluorocyclopropyl)-1-[2,6-dichloro-4-(trifluoromethyl)phenyl]-1H-pyrazol-5-yl}-N,N-dimethylimidoformamide; from the compound of Preparation 34 (42 mg, 0.1 mmol) and phenyl(trichloromethyl)mercury (40 mg, 0.1 mmol) to give the title compound (29 mg) as a white solid.

$^1$H-NMR (CDCl3): 2.31-2.34 (1H), 2.35-2.38 (1H), 2.82-2.86 (3H), 3.09-3.13 (2H), 7.66-7.69 (2H), 7.99-8.03 (1H)

Preparation 6

N'-[3-cyano-1-[2,6-dichloro-4-(pentafluorothio)phenyl]-4-(pentafluorocyclopropyl)-1H-pyrazol-5-yl]-N,N-dimethylimidoformamide To a solution of Preparation 37 (102 mg, 0.20 mmol) in methyl benzoate (4 ml) was added sodium fluoride (3 mg). The mixture was heated to 130° C. and trimethylsilyl-2,2-difluoro-2-(fluorosulphonyl)acetate (1 ml, 0.33 mmol) was added over 10 h.

The reaction mixture was concentrated in vacuo and the residue was purified by column chromatography (silica, 10 g), eluting with toluene. The appropriate fractions were combined and concentrated to give Preparation 6 (75 mg) as a pale yellow solid.

MS (ES): M/Z [MH+] 564.2; expected mass for C16H9Cl2F10N5S+H is 564.0 $^1$H-NMR 2.86-2.90 (3H), 3.07-3.10 (3H), 7.69-7.72 (1H), 7.80-7.85 (2H)

Similarly prepared to Preparation 3 was:

Preparation 7

N'-[3-cyano-1-[2,6-dichloro-4-(pentafluorothio)phenyl]-4-(1,2,2-trifluorocyclopropyl)-1H-pyrazol-5-yl]-N,N-dimethylimidoformamide; from the compound of Preparation 38 (100 mg, 0.21 mmol) to give the title compound (90 mg) as a white solid.

MS (ES): M/Z [MH+] 527.9; expected mass for C16H11Cl2F8N5S+H is 528.0 $^1$H-NMR (CDCl3): 2.09-2.29 (2H), 2.82-2.86 (3H), 3.04-3.09 (3H), 7.79-7.83 (2H), 7.85-7.88 (1H)

Preparation 8

N'-{3-cyano-1-[2,6-dichloro-4-(trifluoromethyl)phenyl]-4-[1-(difluoromethyl)vinyl]-1H-pyrazol-5-yl}-N,N-dimethylimidoformamide To a suspension of methyl triphenyl phosphonium bromide (8.9 g, 25.0 mmol) in tetrahydrofuran (80 ml), at −10° C., was added dropwise butyllithium (1.6M in hexane, 16 ml, 25.0 mmol). The mixture was stirred at room temperature for 20 min, before addition of Preparation 39 (7.6 g, 16.7 mmol) in tetrahydrofuran (16.5 ml). The reaction mixture was then stirred at room temperature overnight. To the reaction mixture was added water and the mixture was extracted with ethyl acetate (2×50 ml). The combined organic phases were separated and concentrated onto silica. The silica/product mixture was purified by column chromatography, eluting with dichloromethane. The appropriate fractions were then combined and concentrated to give Preparation 8 (5.2 g).

MS (ES): M/Z [MH+] 454.0; expected mass for C17H12Cl2F5N5+H is 452.1 $^1$H-NMR (CDCl3): 2.74-2.76 (3H), 2.91-2.94 (3H), 5.77-5.79 (1H), 5.91-5.94 (1H), 6.16-6.45 (1H), 7.62-7.64 (1H), 7.65-7.68 (2H)

Preparation 9

3-Cyano-2-oxo-propionic acid ethyl ester may be prepared according to Achmatowicz, O., Jr; Szymoniak, J. Tetrahedron (1982), 38(9), 1299-1302

Similarly prepared to Preparation 1 was:

Preparation 10

N'-{3-cyano-4-[2,2-difluoro-1-(trifluoromethyl)cyclopropyl]-1-[2,6-difluoro-4-(trifluoromethyl)phenyl]-1H-pyrazol-5-yl}-N,N-dimethylimidoformamide; from the compound of Preparation 40 (250 mg, 0.57 mmol) to give the title compound (250 mg).

MS (ES): M/Z [MH+] 488.1; expected mass for C18H11F10N5+H is 488.1

Similarly prepared to Preparation 3 were:

Preparation 11

N'-{3-cyano-1-[2,6-dichloro-4-(pentafluorothiophenyl]-4-[1-(difluoromethyl)-2,2-difluorocyclopropyl]-1H-pyrazol-5-yl}-N,N-dimethylimidoformamide; from the compound of Preparation 41 (820 mg, 1.61 mmol) to give the title compound (655 mg).

MS (ES): M/Z [MH+] 559.9; expected mass for C17H12Cl2F9N5S+H is 560.0 $^1$H-NMR (CDCl3): 1.81-1.90 (1H), 2.03-2.12 (1H), 2.76-2.79 (3H), 2.99-3.01 (3H), 5.64-5.93 (1H), 7.78-7.81 (2H), 7.87-7.89 (1H)

Preparation 12

N'-{4-{1-[chloro(fluoro)methyl]-2,2-difluorocyclopropyl}-3-cyano-1-[2,6-dichloro-4-(trifluoromethyl)phenyl]-1H-pyrazol-5-yl}-N,N-dimethylimidoformamide; from the compound of Preparation 42 (150 mg, 0.32 mmol) to give the title compound (100 mg).

MS (ES): M/Z [MH+] 517.9; expected mass for C18H12Cl3F6N5+H is 518.0 $^1$H-NMR (CDCl3): 1.86-1.97 (1H), 2.05-2.15 (1H), 2.73-2.80 (3H), 2.95-3.01 (3H), 6.06-6.22 (1H), 7.63-7.71 (2H), 7.88-7.94 (1H)

Preparation 13

N'-{3-cyano-1-[2,6-dichloro-4-(trifluoromethyl)phenyl]-4-[1-(difluoromethyl)-2,2,3,3-tetrafluorocyclopropyl]-1H-pyrazol-5-yl}-N,N-dimethylimidoformamide; from the compound of Preparation 43 (200 mg, 0.41 mmol) to give the title compound (48 mg).

MS (ES): M/Z [MH+] 537.8; expected mass for C18H10Cl2F9N5+H is 538.0

Preparation 14

N'-{3-cyano-1-[2,6-dichloro-4-(trifluoromethyl)phenyl]-4-[2,2,3,3-tetrafluoro-1-(trifluoromethyl)cyclopropyl]-1H-pyrazol-5-yl}-N,N-dimethylimidoformamide; from the compound of Preparation 44 (28 mg, 0.06 mmol) to give the title compound (7 mg).

MS (ES): M/Z [MH+] 555.8; expected mass for C18H9Cl2F10N5+H is 556.0 $^1$H-NMR (CDCl3): 2.79-2.81 (3H), 2.99-3.00 (3H), 7.65-7.67 (1H), 7.67-7.69 (2H)

Preparation 15

N'-{3-cyano-1-[2,6-dichloro-4-(trifluoromethoxy)phenyl]-4-[2,2-difluoro-1-(trifluoromethyl)cyclopropyl]-1H-pyrazol-5-yl}-N,N-dimethylimidoformamide Using a Diazald® kit, a solution of Diazald® in diethyl ether (45 ml) was added dropwise to a solution of potassium hydroxide (1M, 89 ml) in water and ethanol (10 ml), at approximately 50° C. The trap was cooled to −30° C. and after the complete addition of Diazld®, diethyl ether (10 ml) was added to the mixture. Distillation was continued until the distillate was colourless and the diazomethane solution was added to Preparation 45 (1.0 g, 1.92 mmol) in diethyl ether (30 ml). The reaction mixture was then allowed to stand at room temperature overnight. Excess diazomethane was destroyed by addition of acetic acid and the reaction mixture was allowed to evaporate to give Preparation 15 (1.0 g).

MS (ES): M/Z [MH+] 536.0; expected mass for C18H11Cl2F8N5O+H is 536.0

Similarly prepared to Preparation 3 were:

Preparation 16

N'-{3-cyano-1-[2,6-dichloro-4-(trifluoromethoxy)phenyl]-4-[1-(difluoromethyl)-2,2,3,3,-tetrafluorocyclopropyl]-1H-pyrazol-5-yl}-N,N-dimethylimidoformamide; from the compound of Preparation 47 (650 mg, 1.3 mmol) in toluene to give the title compound (50 mg) as a mixture of products.

MS (ES): M/Z [MH+] 553.9; expected mass for C18H10Cl2F9N5O+H is 554.0

Preparation 17

N'-{3-cyano-1-[2,6-dichloro-4-(trifluoromethoxy)phenyl]-4-[1-(difluoromethyl)-2,2-difluorocyclopropyl]-1H-pyrazol-5-yl}-N,N-dimethylimidoformamide; from the compound of Preparation 48 (3.60 g, 7.7 mmol) to give the title compound (3.6 g).

MS (ES): M/Z [MH+] 518.1; expected mass for C18H12Cl2F7N5O+H is 518.0 $^1$H-NMR (CDCl3): 1.82-1.91 (1H), 2.02-2.11 (1H), 2.74-2.79 (3H), 2.97-3.00 (3H), 5.64-5.93 (1H), 7.26-7.31 (2H), 7.83-7.87 (1H)

Preparation 18

N'-{3-cyano-1-[2,6-dichloro-4-(trifluoromethyl)phenyl]-4-[2,2-difluoro-1-(fluoromethyl)cyclopropyl]-1H-pyrazol-5-yl}-N,N-dimethylimidoformamide; from the compound of Preparation 49 (100 mg, 0.23 mmol), to give the title compound (100 mg).

MS (ES): M/Z [MH+] 484.0; expected mass for C18H13Cl2F6N5+H is 484.1

Preparation 19

N'-[3-cyano-1-[2,6-dichloro-4-(trifluoromethyl)phenyl]-4-(2,2-difluoro-1-methylcyclopropyl)-1H-pyrazol-5-yl]-N,N-dimethylimidoformamide; from the compound of Preparation 50 (137 mg, 0.33 mmol) to give the title compound (80 mg).

MS (ES): M/Z [MH+] 466.0; expected mass for C18H14Cl2F5N5+H is 466.1

Similarly prepared to Preparation 15 was:

Preparation 20

N'-{3-cyano-1-{2,6-dichloro-4-[(trifluoromethyl)thio]phenyl}-4-[2,2-difluoro-1-(trifluoromethyl)cyclopropyl]-1H-pyrazol-5-yl}-N,N-dimethylimidoformamide; from the compound of Preparation 51 (2.50 g, 4.6 mmol) to give the title compound (1.8 g).

MS (ES): M/Z [MH+] 552.9; expected mass for C18H11Cl2F8N5S+H is 552.0

Preparation 21

(2,6-Difluoro-4-trifluoromethyl-phenyl)-hydrazine

A mixture of 1,2,3-trifluoro-5-(trifluoromethyl)benzene (300 g, 1.5 mmol) and hydrazine monohydrate (300 g, 6.0 mmol) in ethanol (1200 ml) was heated at reflux overnight.

The reaction mixture was concentrated in vacuo and the residue was re-crystallised from 2-propanol to give Preparation 21 (194 g).

MS (ES): M/Z [MH+] 213.2; expected mass for $C_7H_5F_5N_2$+H is 213.1 $^1$H-NMR (CDCl3): 3.81-4.08 (2H), 5.23-5.41 (1H), 7.03-7.14 (2H)

Similarly prepared to Preparation 3 were:

Preparation 22

N'-{1-[3-chloro-5-(trifluoromethyl)pyridin-2-yl]-3-cyano-4-[2,2-difluoro-1-(trifluoromethyl)cyclopropyl]-1H-pyrazol-5-yl}-N,N-dimethylimidoformamide; from the compound of Preparation 52 (800 mg, 1.83 mmol) to give the title compound (260 mg).

MS (ES): M/Z [MH+] 487.2; expected mass for $C_{17}H_{11}ClF_8N_6$+H is 487.1

Preparation 23

N'-{3-cyano-1-[2,6-dichloro-4-(trifluoromethyl)phenyl]-4-[1-(difluoromethyl)-2,2-difluorocyclopropyl]-1H-pyrazol-5-yl}-N,N-dimethylimidoformamide; from the compound of Preparation 8 (4.52 g, 10.0 mmol), to give the title compound (4.0 g).

MS (ES): M/Z [MH+] 501.92; expected mass for $C_{18}H_{12}Cl_2F_7N_5$+H is 502.04 $^1$H-NMR (CDCl3): 1.82-1.91 (1H), 2.03-2.11 (1H), 2.73-2.78 (3H), 2.97-3.01 (3H), 5.66-5.93 (1H), 7.63-7.69 (2H), 7.85-7.89 (1H)

Preparation 24

Ethyl 2,3-dicyanopropanoate may be prepared according to Hainzl, D.; Cole, L. M.; Casida, J. E. Chemical Research in Toxicology (1998), 11(12), 1529-1535

Preparation 25

1-[2,6-dichloro-4-(trifluoromethyl)phenyl]-4-[2,2-difluoro-1-(trifluoromethyl)cyclopropyl]-5-{[(1E)-pyridin-4-ylmethylene]amino}-1H-pyrazole-3-carbonitrile To Example 2a (120 mg, 0.26 mmol) and 4A molecular sieves in toluene (10 ml) was added isonicotinaldehyde (550 µl, 6.71 mmol) and p-toluenesulphonic acid (catalytic amount, 5 mg). The reaction mixture was then heated at reflux using a Dean Stark apparatus for 9 days. To the reaction mixture was added water and the mixture was adjusted to pH 2 by addition of hydrochloric acid (4N). The mixture was then neutralised by addition of saturated aqueous sodium carbonate solution, extracted with ethyl acetate (3×20 ml) and the combined extracts dried (MgSO4) and concentrated in vacuo to give Preparation 25 (200 mg).

MS (ES): M/Z [MH+] 554.0; expected mass for $C_{21}H_9Cl_2F_8N_5$+H is 554.0

Similarly prepared to Preparation 15 was:

Preparation 26

N'-{3-cyano-1-[2,6-dichloro-4-(difluoromethoxy)phenyl]-4-[2,2-difluoro-1-(trifluoromethyl)cyclopropyl]-1H-pyrazol-5-yl}-N,N-dimethylimidoformamide; from Preparation 53 (104 mg, 0.21 mmol) to give the title compound (110 mg).

MS (ES): M/Z [MH+] 518.0; expected mass for $C_{18}H_{12}Cl_2F_7N_5O$+H is 518.0 $^1$H-NMR (CDCl3): 2.05-2.21 (1H), 2.41-2.55 (1H), 2.77-2.81 (3H), 2.98-3.00 (3H), 6.36-6.72 (1H), 7.18-7.21 (2H), 7.22-7.24 (1H)

Similarly prepared to Preparation 3 was:

Preparation 27

N'-{3-cyano-1-[2,6-dichloro-4-pentafluorothiophenyl]-4-[1-(difluoromethyl)-2,2,3,3-tetrafluorocyclopropyl]-1H-pyrazol-5-yl}-N,N-dimethylimidoformamide; from the compound of Preparation 54 (618 mg, 1.13 mmol), to give the title compound (138 mg).

MS (ES): M/Z [MH+] 596.1; expected mass for $C_{17}H_{10}Cl_2F_{11}N_5S$+H is 596.0 $^1$H-NMR (CDCl3): 2.78-2.81 (3H), 2.99-3.02 (3H), 5.95-6.24 (1H), 7.76-7.79 (1H), 7.79-7.82 (2H)

Preparation 28

2,6-Dichloro-4-difluoromethoxy-aniline

To a solution of 4-[(difluoromethoxy)methyl]aniline (15.0 g, 94.3 mmol) in acetonitrile (150 ml) was added N-chlorosuccinimide (25.2 g, 18.9 mmol) and the reaction mixture was stirred under nitrogen for 2 h. The reaction mixture was concentrated in vacuo and the residue was partitioned between diethyl ether (500 ml) and water (125 ml). The organic layer was separated, washed with aqueous sodium thiosulphate solution, water and brine, dried (MgSO4) and treated with charcoal. The solution was then filtered and concentrated in vacuo. The residue was extracted with hexane (2×300 ml) and the combined extracts were concentrated in vacuo to give Preparation 28 (13.8 g).

MS (ES): M/Z [MH+] 228; expected mass for $C_7H_5Cl_2F_2NO$+H is 227.98

Preparation 29 ethyl 5-amino-1-[2,6-difluoro-4-(trifluoromethyl)phenyl]-1H-pyrazole-3-carboxylate To a solution of Preparation 9 (92.6 g, 0.66 mmol) in ethanol (2 l) was added Preparation 21 (95.0 g, 0.45 mmol) and the reaction mixture was heated at reflux overnight. The reaction mixture was cooled and sodium hydrogen carbonate (36.0 g, 0.43 mmol) was added. The mixture was then heated at reflux overnight. The reaction mixture was concentrated in vacuo and to the residue was added diethyl ether (1 l). The solution was filtered, washed with water, hydrochloric acid and further water, dried and concentrated in vacuo. The residue was purified by column chromatography (silica, 70 g), eluting with toluene. The appropriate fractions were combined and concentrated to give Preparation 29 (40 g).

MS (ES): M/Z [MH+] 336.1; expected mass for $C_{13}H_{10}F_5N_3O_2$+H is 336.1

Preparation 30

5-Amino-1-(2,6-dichloro-4-difluoromethoxy-phenyl)-1H-pyrazole-3-carbonitrile

To sulphuric acid (concentrated, 21 ml), at 15° C., was added sodium nitrite (4.8 g, 69.6 mmol). After stirring for 1 h, glacial acetic acid (17.3 ml) was added, followed by Preparation 28 (13.8 g, 60.3 mmol) in acetic acid (33.8 ml), added dropwise, keeping the temperature of the mixture below 25° C. The solution was heated at 50° C. for 1 h, cooled and added dropwise to a mixture of Preparation 24 (10.6 g, 69.6 mmol), acetic acid (42.8 ml) and ice/water (55 ml), at 0° C. The reaction mixture was then stirred at room temperature overnight. To the reaction mixture was added dichloromethane (300 ml) and the mixture was stirred. The two layers were separated and the organic layer was washed with water. To the organic layer was added ammonium hydroxide (concentrated, 125 ml) and ice and the mixture was stirred at 5° C. for 4 h. The organic layer was again separated and stirred overnight with activated charcoal. The mixture was filtered through Celite® and the filtrate was concentrated in vacuo. The residue was purified by column chromatography (Biotage, silica, 90 g), eluting with dichloromethane. The appropriate fractions were combined and concentrated to give Preparation 30 (3.1 g).

MS (ES): M/Z [MH+] 319.0; expected mass for $C_{11}H_6Cl_2F_2N_4O+H$ is 319.0 $^1$H-NMR (CDCl3): 3.60-3.88 (2H), 6.38-6.75 (1H), 7.22-7.23 (1H), 7.27-7.29 (2H)

Preparation 31

N'-{3-cyano-1-[2,6-dichloro-4-(trifluoromethyl)phenyl]-4-vinyl-1H-pyrazol-5-yl}-N,N-dimethylimidoformamide A solution of Preparation 57 (500 mg, 1.44 mmol) in N,N-dimethylformamide dimethyl acetal (6 ml) was heated at reflux for 1 h.

The reaction mixture was cooled and concentrated in vacuo. To the residue was added diethyl ether (10 ml), followed by hexane, until precipitation occurred. The solution was then concentrated under a stream of nitrogen to give the crude product. The crude product was washed with hexane and dried under vacuum to give Preparation 31 (560 mg) as a pale yellow solid.

MS (ES): M/Z [MH+] 402.2; expected mass for $C_{16}H_{12}Cl_2F_3N_5+H$ is 402.1 $^1$H-NMR (CDCl3): 2.81-2.87 (3H), 3.00-3.05 (3H), 5.29-5.36 (1H), 5.91-6.00 (1H), 6.35-6.46 (1H), 7.64-7.67 (1H), 7.68-7.72 (2H)

Preparation 32

N'-{3-cyano-1-[2,6-dichloro-4-(pentafluorothio)phenyl]-4-[1-(trifluoromethyl)vinyl]-1H-pyrazol-5-yl}-N,N-dimethylimidoformamide A mixture of Preparation 58 (4.0 g, 7.1 mmol), Preparation 59 (3.0 g, 14.0 mmol), aqueous sodium hydrogen carbonate solution (1M, 40 ml), toluene (100 ml) and methanol (40 ml) was degassed and placed under a nitrogen atmosphere. To the mixture was added tetrakis(triphenylphosphine)palladium(0) (360 mg) and the reaction mixture was degassed and heated at reflux for 8 h. The reaction mixture was partitioned between water (50 ml) and diethyl ether (75 ml). The two layers were separated and the aqueous layer was re-extracted with diethyl ether (3×50 ml). The combined organic phases were dried (Na2SO4) and concentrated in vacuo. The residue was purified using an Isolute™ cartridge (silica, 25 g) with gradient elution, ethyl acetate:cyclohexane [1:3 to 1:1]. The appropriate fractions were combined and concentrated and the residue was re-chromatographed using an Isolute™ cartridge (silica, 70 g), eluting with toluene. The product-containing fractions were concentrated to give Preparation 32 (1.34 g).

MS (ES): M/Z [MH+] 528.0; expected mass for $C_{16}H_{11}Cl_2F_8N_5S+H$ is 528.0 $^1$H-NMR (CDCl3): 2.74-2.78 (3H), 2.92-2.97 (3H), 5.85-5.89 (1H), 6.20-6.24 (1H), 7.63-7.66 (1H), 7.79-7.82 (2H)

Similarly prepared to Preparation 31 was:

Preparation 33

N'-{3-cyano-1-[2,6-dichloro-4-(trifluoromethyl)phenyl]-4-[1-(trifluoromethyl)vinyl]-1H-pyrazol-5-yl}-N,N-dimethylimidoformamide; from the compound of Preparation 60 (170 mg, 0.41 mmol) to give the title compound (140 mg) as a white solid.

MS (ES): M/Z [MH+] 470.2; expected mass for $C_{17}H_{11}Cl_2F_6N_5+H$ is 470.0 $^1$H-NMR (CDCl3): 2.76-2.80 (3H), 2.96-3.00 (3H), 5.90-5.92 (1H), 6.23-6.26 (1H), 7.66-7.68 (1H), 7.69-7.72 (2H)

Preparation 34

N'-[3-cyano-1-[2,6-dichloro-4-(trifluoromethyl)phenyl]-4-(1-fluorovinyl)-1H-pyrazol-5-yl]-N,N-dimethylimidoformamide To a solution of Preparation 62 (2.9 g, 5.7 mmol) and Preparation 61 (2.5 g, 7.5 mmol) in N,N-dimethylformamide (50 ml), under nitrogen, was added tetrakis(triphenylphosphine)palladium(0) (330 mg, 0.3 mmol). The reaction mixture was then heated at 80° C. for 4 h. To the reaction mixture was added water (150 ml) and the mixture was extracted with ethyl acetate (150 ml). The combined extracts were washed with water (2×100 ml) and saturated brine solution (100 ml), dried (MgSO4) and concentrated in vacuo. The residue was triturated with hexane and the precipitate collected by filtration and dried to give Preparation 34 (2.35 g) as a brown solid.

$^1$H-NMR (CDCl3): 2.76-2.78 (3H), 2.99-3.01 (3H), 4.92-5.10 (2H), 7.66-7.68 (2H), 7.70-7.73 (1H)

Preparation 35

N'-[3-cyano-1-[2,6-dichloro-4-(trifluoromethyl)phenyl]-4-(trifluorovinyl)-1H-pyrazol-5-yl]-N,N-dimethylimidoformamide To a suspension of dichlorobis(triphenylphosphine) palladium II (70 mg) in tetrahydrofuran (2 ml) was added diisobutylaluminium hydride (1.5M in toluene, 133 µl). To this solution was added bromofluoroethylene (200 mmol), followed by Preparation 64 (1.0 mmol) and the reaction mixture was heated at reflux, under nitrogen, overnight. The reaction mixture was partitioned between ethyl acetate (50 ml) and water and the organic phase was separated, washed with brine, dried (MgSO4) and concentrated in vacuo. The residue was purified using an Isolute™ column (silica, 20 g), eluting with dichloromethane. The appropriate fractions were combined and concentrated and the residue was dissolved in hexane. The resulting precipitate was isolated and dried to give Preparation 35 (200 mg) as a crystalline solid.

MS (ES): M/Z [MH+] 456.2; expected mass for $C_{16}H_9Cl_2F_6N_5+H$ is 456.0 $^1$H-NMR (CDCl3): 2.77-2.80 (3H), 3.02-3.05 (3H), 7.67-7.69 (2H), 7.74-7.77 (1H)

Preparation 36

2,6-dichloro-4-trifluoromethylthio-aniline

To a solution of Preparation 97 (4.8 g, 25.0 mmol) in acetonitrile (50 ml), at 50° C., was added N-chlorosuccinimide (6.7 g, 50.0 mmol). The reaction mixture was then stirred at 50° C. for 1 h. To the reaction mixture was added water (150 ml) and the mixture was extracted with dichloromethane (100 ml). The combined extracts were dried (MgSO$_4$) and concentrated in vacuo to give Preparation 36 (1.0 g).

Preparation 37

N'-[3-cyano-1-[2,6-dichloro-4-(pentafluorothio)phenyl]-4-(trifluorovinyl)-1H-pyrazol-5-yl]-N,N-dimethylimidoformamide A suspension of Rieke™ Zinc in tetrahydrofuran (5%, 26 ml, 20 mmol) was stirred under a nitrogen atmosphere. The nitrogen atmosphere was exchanged for bromotrifluoroethylene (approx. 40 mmol) and the solution was stirred for a further 3 h. Nitrogen was passed through the solution and the excess zinc was allowed to settle, leaving a supernatant solution of the desired zinc reagent. To a solution of Preparation 58 (2.24 g, 4.0 mmol) and tetrakis(triphenylphosphine)palladium(0) (231 mg) in tetrahydrofuran (5 ml) was added the zinc reagent solution (12 ml, approx. 5.0 mmol). The reaction mixture was then heated at reflux under nitrogen for 5 h. To the reaction mixture was added excess aqueous acetic acid (dilute) and the mixture was extracted with dichloromethane (150 ml). The extracts were washed with brine, dried (MgSO$_4$) and concentrated in vacuo. The residue was purified using an Isolute™ column (silica, 50 g), eluting with toluene. The appropriate fractions were combined and concentrated to give Preparation 37 (913 mg).

MS (ES): M/Z [MH+] 514.2; expected mass for C15H9Cl2F8N5S+H is 514.0 $^1$H-NMR (CDCl3): 2.79-2.82 (3H), 3.03-3.06 (3H), 7.75-7.77 (1H), 7.80-7.83 (2H)

Similarly prepared to Preparation 34 was:

Preparation 38

N'-[3-cyano-1-[2,6-dichloro-4-pentafluorothiophenyl]-4-(1-fluorovinyl)-1H-pyrazol-5-yl]-N,N-dimethylimidoformamide; from the compounds of Preparation 58 (380 mg, 0.68 mmol) and Preparation 61 (295 mg, 0.88 mmol) to give the title compound (85 mg).

MS (ES): M/Z [MH+] 477.9; expected mass for C15H11Cl2F6N5S+H is 478.0 $^1$H-NMR (CDCl3): 2.77-2.81 (3H), 2.99-3.03 (3H), 4.92-5.09 (2H), 7.70-7.73 (1H), 7.79-7.82 (2H)

Preparation 39

N'-[3-cyano-1-[2,6-dichloro-4-(trifluoromethyl)phenyl]-4-(difluoroacetyl)-1H-pyrazol-5-yl]-N,N-dimethylimidoformamide To a solution of Preparation 62 (12.5 g, 25.0 mmol) in tetrahydrofuran (50 ml), at −30° C., was added dropwise isopropylmagnesium chloride (2M in tetrahydrofuran, 13.75 ml, 27.5 mmol). The reaction mixture was stirred at −30° C. for 30 min, before addition of difluoroacetic acid chloride (2M in tetrahydrofuran, 18.75, 37.5 mmol). The reaction mixture was then allowed to warm to room temperature. To the reaction mixture was added saturated aqueous sodium hydrogen carbonate solution and the mixture was extracted with ethyl acetate (×3). The combined organic phases were washed with saturated sodium chloride solution, dried (MgSO$_4$) and concentrated in vacuo. The residue was re-crystallised from diethyl ether, by addition of petroleum ether, to give Preparation 39 (7.6 g).

$^1$H-NMR (CDCl3): 2.78-2.82 (3H), 3.08-3.12 (3H), 6.41-6.69 (1H), 7.67-7.71 (2H), 8.49-8.52 (1H)

Preparation 40

N'-{3-cyano-1-[2,6-difluoro-4-(trifluoromethyl)phenyl]-4-[1-(trifluoromethyl)vinyl]-1H-pyrazol-5-yl}-N,N-dimethylimidoformamide To Preparation 66 (2.0 g, 4.26 mmol) and tetrakis(triphenylphosphine)palladium(0) (246 mg, 0.21 mmol) in N,N-dimethylformamide (70 ml) was added a solution of Preparation 65 in tetrahydrofuran (15.75 ml, 6.3 mmol). The reaction mixture was then heated at 110° C. overnight in apparatus equipped with a Dean-Stark trap.

The reaction mixture was concentrated in vacuo and the residue was purified by flash chromatography (silica), eluting with toluene. The appropriate fractions were combined and concentrated to give Preparation 40 (1.5 g).

MS (ES): M/Z [MH+] 438.0; expected mass for C17H11F8N5+H is 438.1 $^1$H-NMR (CDCl3): 2.78-2.81 (3H), 2.95-2.99 (3H), 5.84-5.87 (1H), 6.20-6.23 (1H), 7.28-7.33 (2H), 7.64-7.68 (1H)

Preparation 41

N'-{3-cyano-1-[2,6-dichloro-4-pentafluorothiophenyl]-4-[1-(difluoromethyl)vinyl]-1H-pyrazol-5-yl}-N,N-dimethylimidoformamide To a solution of methyltriphenylphosphonium bromide (1.80 g, 5.05 mmol) in tetrahydrofuran (20 ml), at 0° C., was added n-butyllithium (1.6N in hexane, 3.2 ml, 5.05 mmol) via syringe. After stirring for 15 min, Preparation 67 (1.72 g, 3.37 mmol) in tetrahydrofuran (10 ml) was added and the reaction mixture was stirred at room temperature for 2.5 h. To the reaction mixture was added water (50 ml) and the mixture was extracted with ethyl acetate (3×30 ml). The combined organic phases were dried (MgSO$_4$) and concentrated in vacuo. The residue was purified by column chromatography (silica) with gradient elution, ethyl acetate:hexane [1:4 to 1:2]. The appropriate fractions were combined and concentrated to give Preparation 41 (1.40 g).

MS (ES): M/Z [MH+] 509.9; expected mass for C16H12Cl2F7N5S+H is 510.0 $^1$H-NMR (CDCl3): 2.75-2.78 (3H), 2.91-2.95 (3H), 5.76-5.78 (1H), 5.91-5.94 (1H), 6.14-6.43 (1H), 7.63-7.65 (1H), 7.79-7.82 (2H)

Similarly prepared to Preparation 41 was:

Preparation 42

N'-{4-{1-[chloro(fluoro)methyl]vinyl}-3-cyano-1-[2,6-dichloro-4-(trifluoromethyl)phenyl]-1H-pyrazol-5-yl}-N,N-dimethylimidoformamide; from the compound of Preparation 68 (800 mg, 1.70 mmol) to give the title compound (800 mg).

MS (ES): M/Z [MH+] 468.1; expected mass for C17H12Cl3F4N5+H is 468.0 $^1$H-NMR (CDCl3): 2.75-2.78 (3H), 2.91-2.94 (3H), 5.67-5.70 (1H), 5.91-5.95 (1H), 6.72-6.86 (1H), 7.65-7.68 (2H), 7.70-7.73 (1H)

Preparation 43

N'-{3-cyano-1-[2,6-dichloro-4-(trifluoromethyl)phenyl]-4-[1-(difluoromethyl)-2,2-difluorovinyl]-1H-pyrazol-5-yl}-N,N-dimethylimidoformamide To a solution of triphenylphosphine (524 mg, 2.0 mmol) in N,N-dimethylformamide (5 ml), under nitrogen, was added dibromodifluoromethane (420 mg, 2.0 mmol). The mixture was stirred at room temperature for 30 min, before the addition of Preparation 39 (454 mg, 1.0 mmol) in N,N-dimethylformamide (1 ml). To the mixture was added Rieke® zinc (130 mg, 2.0 mmol) and the reaction mixture was stirred for 1 h. The reaction mixture was concentrated in vacuo and the residue was purified by flash chromatography (silica), eluting with dichloromethane. The appropriate fractions were combined and concentrated to give Preparation 43 (410 mg).

MS (ES): M/Z [MH+] 487.8; expected mass for C17H10Cl2F7N5+H is 488.0 $^1$H-NMR (CDCl3): 2.74-2.77 (3H), 2.95-2.98 (3H), 6.43-6.72 (1H), 7.66-7.68 (2H), 7.69-7.70 (1H)

Preparation 44

N'-{3-cyano-1-[2,6-dichloro-4-(trifluoromethyl)phenyl]-4-[2,2-difluoro-1-(trifluoromethyl)vinyl]-1H-pyrazol-5-yl}-N,N-dimethylimidoformamide A suspension of Rieke® zinc in tetrahydrofuran (15.6 ml, 12.0 mmol) was allowed to settle and as much tetrahydrofuran as possible removed. To the Rieke® zinc was then added dry N,N-dimethylformamide (25 ml) and the solution was stirred under nitrogen. 2-bromopentafluoropropene (1.05 g, 5.0 mmol) was condensed into a cooled vessel, under nitrogen, and added slowly to the zinc solution via syringe. The reaction mixture was then stirred at room temperature for 12 h. To Preparation 62 (1.04 g, 2.0 mmol) and tetrakis(triphenylphosphine)palladium(0) (120 mg), under nitrogen, was added the solution of the zinc reagent in N,N-dimethylformamide (12 ml, approx. 4.0 mmol). The reaction mixture was stirred at 90° C. for 3 h and then at 100° C. for 6 h. The reaction mixture was partitioned between ethyl acetate and dilute hydrochloric acid. The organic layer was separated, dried (MgSO$_4$) and concentrated in vacuo. The residue was purified using an Isolute™ column (silica, 50 g), eluting with toluene. The product-containing fractions were concentrated and the residue was dissolved in acetonitrile/water/dimethyl sulphoxide (12:1:3, 1.6 ml). This solution was further purified by automated preparative liquid chromatography (Gilson system, 150×30 mm Luna C18 5 μ column) using an acetonitrile:water gradient [65:35 to 95:5]. The appropriate fractions were concentrated in vacuo to give Preparation 44 (28 mg).

MS (ES): M/Z [MH+] 506.0; expected mass for C17H9Cl2F8N5+H is 506.0 $^1$H-NMR (CDCl3): 2.74-2.81 (3H), 2.96-3.02 (3H), 7.62-7.66 (1H), 7.66-7.71 (2H)

Preparation 45

N'-{3-cyano-1-[2,6-dichloro-4-(trifluoromethoxy)phenyl]-4-[2,2-difluoro-1-(trifluoromethyl)vinyl]-1H-pyrazol-5-yl}-N,N-dimethylimidoformamide To a solution of Preparation 71 (6.7 g, 13.7 mmol) in N,N-dimethylformamide (60 ml) was added triphenylphosphine (21.6 g, 82.3 mmol) and dibromodifluoromethane (8.6 g, 41.2 mmol). The reaction mixture was then stirred under nitrogen at room temperature for 5 days. The reaction mixture was concentrated in vacuo and the residue was purified by flash chromatography (silica), with gradient elution, toluene: dichloromethane [1:0 to 1:2]. The appropriate fractions were combined and concentrated to give Preparation 45 (2.8 g).

MS (ES): M/Z [MH+] 522.0; expected mass for C17H9Cl2F8N5O+H is 522.0

Preparation 46

Ethyl 2,3-dicyanopropanoate

To a solution of ethyl cyanoacetate (916.0 g, 8.10 mol) in N,N-dimethylformamide (2.5 L) was added slowly glycolonitrile (700.0 g, 6.75 mol) in water (55% solution). To the mixture was added potassium carbonate (932.7 g, 6.75 mol), over 1.5 h, ensuring that the reaction temperature did not rise above 30° C. The reaction mixture was then stirred at room temperature overnight. The reaction mixture was filtered and the filtrate adjusted to pH 3 by addition of acid. The organic phase was separated and partially concentrated in vacuo. To the concentrate was added diethyl ether (1L) and the solution was washed with water (5×1 L), dried (MgSO$_4$) and concentrated in vacuo to give Preparation 46 (803 g).

$^1$H-NMR (CDCl3): 1.28-1.34 (3H), 2.95-3.01 (2H), 3.84-3.89 (1H), 4.27-4.33 (2H)

Similarly prepared to Preparation 43 was:

Preparation 47

N'-{3-cyano-1-[2,6-dichloro-4-(trifluoromethoxy)phenyl]-4-[1-(difluoromethyl)-2,2-difluorovinyl]-1H-pyrazol-5-yl}-N,N-dimethylimidoformamide; from the compound of Preparation 72 (1.1 g, 2.3 mmol) to give the title compound (650 mg).

$^1$H-NMR (CDCl3): 2.74-2.78 (3H), 2.93-2.98 (3H), 6.42-6.71 (1H), 7.28-7.31 (2H), 7.65-7.69 (1H)

Preparation 48

N'-{3-cyano-1-[2,6-dichloro-4-(trifluoromethoxy)phenyl]-4-[1-(difluoromethyl)vinyl]-1H-pyrazol-5-yl}-N,N-dimethylimidoformamide A mixture of potassium tert-butoxide (1M solution, 11.7 ml, 11.7 mmol) and methyltriphenylphosphonium bromide (3.91 g, 14.0 mmol) in cyclohexane (50 ml) was stirred at 50° C. for 45 min and then cooled to 10° C. A solution of Preparation 72 (4.40 g, 9.36 mmol) in dichloromethane (20 ml) was added and the reaction mixture was allowed to warm to room temperature. The reaction mixture was concentrated in vacuo and the residue was purified by flash chromatography (silica) with gradient elution, toluene:dichloromethane [1:0 to 0:1]. The appropriate fractions were combined and concentrated to give Preparation 48 (3.6 g).

MS (ES): M/Z [MH+] 468.0; expected mass for C17H12Cl2F5N5O+H is 468.0 $^1$H-NMR (CDCl3): 2.74-2.78 (3H), 2.90-2.95 (3H), 5.76-5.80 (1H), 5.89-5.93 (1H), 6.16-6.46 (1H), 7.27-7.31 (2H), 7.58-7.62 (1H)

Similarly prepared was:

Preparation 49

N'-{3-cyano-1-[2,6-dichloro-4-(trifluoromethyl)phenyl]-4-[1-(fluoromethyl)vinyl]-1H-pyrazol-5-yl}-N,N-dimethylimidoformamide; from the compound of Preparation 73 (370 mg, 0.85 mmol) to give the title compound (242 mg).

MS (ES): M/Z [MH+] 434.0; expected mass for C17H13Cl2F4N5+H is 434.1 $^1$H-NMR (CDCl3): 2.78-2.81 (3H), 2.92-2.95 (3H), 4.95-4.98 (1H), 5.07-5.10 (1H), 5.61-5.64 (2H), 7.61-7.64 (1H), 7.65-7.68 (2H)

Preparation 50

N'-{3-cyano-1-[2,6-dichloro-4-(trifluoromethyl)phenyl]-4-isopropenyl-1H-pyrazol-5-yl}-N,N-dimethylimidoformamide To a solution of tetrabutylammonium chloride (204 mg, 0.69 mmol) in acetonitrile (7 ml) were added molecular sieves (4 Å, 3.0 g). After 30 min, the solution was decanted off and added to Preparation 74 (100 mg, 0.23 mmol). This mixture was cooled to −10° C. and thionyl chloride (33.5 μl, 0.46 mmol) was added dropwise. After stirring for 15 min, sodium methylmercaptide (32 mg, 0.46 mmol) was added and the reaction mixture was allowed to warm to room temperature overnight. The reaction mixture was concentrated in vacuo and to the residue was added dichloromethane (50 ml). The solution was washed with water (3×35 ml), dried ($MgSO_4$) and concentrated in vacuo. The residue was passed through a silica plug, eluting with dichloromethane. The filtrate was concentrated in vacuo to give Preparation 50 (137 mg).

MS (ES): M/Z [MH+] 416.0; expected mass for $C17H14Cl2F3N5+H$ is 416.1 $^1$H-NMR (CDCl3): 2.01-2.03 (3H), 2.76-2.78 (3H), 2.93-2.97 (3H), 5.20-5.22 (1H), 5.30-5.33 (1H), 7.59-7.60 (1H), 7.64-7.67 (2H)

Similarly prepared to Preparation 43 was:

Preparation 51

N'-{3-cyano-1-{2,6-dichloro-4-[(trifluoromethyl)thio]phenyl}-4-[2,2-difluoro-1-(trifluoromethyl)vinyl]-1H-pyrazol-5-yl}-N,N-dimethylimidoformamide; from the compound of Preparation 75 (6.50 g, 12.9 mmol) to give the title compound (2.5 g).

MS (ES): M/Z [MH+] 537.9; expected mass for $C17H9Cl2F8N5S+H$ is 538.0 $^1$H-NMR (CDCl3): 2.74-2.77 (3H), 2.96-2.99 (3H), 7.60-7.63 (1H), 7.68-7.72 (2H)

Similarly prepared to Preparation 48 was:

Preparation 52

N'-{1-[3-chloro-5-(trifluoromethyl)pyridin-2-yl]-3-cyano4-[1-(trifluoromethyl)vinyl]-1H-pyrazol-5-yl}-N,N-dimethylimidoformamide; from the compound of Preparation 76 (1.00 g, 2.3 mmol) to give the title compound (820 mg).

MS (ES): M/Z [MH+] 437.0; expected mass for $C16H11ClF6N6+H$ is 437.1 $^1$H-NMR (CDCl3): 2.89-2.91 (3H), 2.98-3.01 (3H), 5.96-5.98 (1H), 6.26-6.28 (1H), 7.65-7.68 (1H), 8.14-8.16 (1H), 8.69-8.71 (1H)

Similarly prepared to Preparation 43 were:

Preparation 53

N'-{3-cyano-1-[2,6-dichloro-4-(difluoromethoxy)phenyl]-4-[2,2-difluoro-1-(trifluoromethyl)vinyl]-1H-pyrazol-5-yl}-N,N-dimethylimidoformamide; from the compound of Preparation 77 (425 mg, 0.9 mmol) to give the title compound (107 mg).

MS (ES): M/Z [MH+] 504.0; expected mass for $C17H10Cl2F7N5O+H$ is 504.0 $^1$H-NMR (CDCl3): 2.77-2.80 (3H), 2.96-2.99 (3H), 6.36-6.72 (1H), 7.20-7.22 (2H), 7.58-7.60 (1H)

Preparation 54

N'-{3-cyano-1-[2,6-dichloro-4-pentafluorothiophenyl]-4-[1-(difluoromethyl)-2,2-difluorovinyl]-1H-pyrazol-5-yl}-N,N-dimethylimidoformamide; from the compound of Preparation 67 (1.02 g, 2.0 mmol) to give the title compound (612 mg).

MS (ES): M/Z [MH+] 546.1; expected mass for $C16H10Cl2F9N5S+H$ is 546.0

Similarly prepared to Preparation 3 was:

Preparation 55

N'-{4-{1-[chloro(difluoro)methyl]-2,2-difluorocyclopropyl}-3-cyano-1-[2,6-dichloro-4-(trifluoromethyl)phenyl]-1H-pyrazol-5-yl}-N,N-dimethylimidoformamide; from the compound of Preparation 78 (100 mg, 0.2 mmol) to give the title compound (124 mg).

MS (ES): M/Z [MH+] 535.9; expected mass for $C18H11Cl3F7N5+H$ is 536.0

Preparation 56

5-amino-1-[2,6-difluoro-4-(trifluoromethyl)phenyl]-1H-pyrazole-3-carboxamide

A mixture of Preparation 29 (600 mg, 1.79 mmol), methanol (5 ml) and ammonium hydroxide (5 ml) was heated at 50° C. for 5 h. The reaction mixture was concentrated in vacuo and the residue was purified by column chromatography (silica), eluting with dichloromethane/ethyl acetate [1:1]. The appropriate fractions were combined and concentrated to give the title compound (210 mg).

MS (ES): M/Z [MH+] 307.1; expected mass for $C11H7F5N4O+H$ is 307.06 $^1$H-NMR (CD3OD): 5.93-5.95 (1H), 7.58-7.64 (2H)

Preparation 57

5-amino-1-[2,6-dichloro-4-(trifluoromethyl)phenyl]-4-vinyl-1H-pyrazole-3-carbonitrile may be prepared according to EP933363 A1, WO9824767 or WO9804530.

Similarly prepared to Preparation 31 was:

Preparation 58

N'-{3-cyano-1-[2,6-dichloro-4-(pentafluorothio)phenyl]-4-iodo-1H-pyrazol-5-yl}-N,N-dimethylimidoformamide; from the compound of Preparation 79 (52 g, 103 mmol) to give the title compound (45 g) as a light brown solid.

$^1$H-NMR (CDCl3): 2.77-2.81 (3H), 3.02-3.05 (3H), 7.78-7.81 (2H), 8.21-8.24 (1H)

Preparation 59

1-(trifluoromethyl)vinylboronic acid

To magnesium turnings (5.83 g, 0.24 mol) in tetrahydrofuran (400 ml) was added dropwise trimethyl borate (68.13 ml, 0.6 mol). The reaction mixture was cooled to 0° C. and 2-bromo-3,3,3-trifluoropropene (20.75 ml, 0.2 mol) was added dropwise. The reaction mixture was then allowed to warm to room temperature and stirred under nitrogen overnight. The reaction mixture was again cooled to 0°C and hydrochloric acid (5M, 200 ml) was added dropwise, ensuring that the temperature of the solution remained below 10°C. The reaction mixture was then stirred under nitrogen for 48 h. To the reaction mixture was added diethyl ether (100 ml) and water (200 ml) to give two phases. The aqueous layer was separated and extracted with diethyl ether (100 ml). The combined organic phases were washed with water (100 ml), dried (MgSO₄) and concentrated in vacuo. To the residue was added cyclohexane (50 ml), resulting in precipitate formation. The precipitate was isolated by decanting the solution, washed with cyclohexane, and dried in vacuo to give Preparation 59 (2.62 g, 0.02 mol) as a white solid.

¹H-NMR (DMSO): 5.50-5.57 (1H), 5.80-5.88 (1H), 6.22-6.36 (2H)

Preparation 60

5-amino-1-[2,6-dichloro-4-(trifluoromethyl)phenyl]-4-[1-(trifluoromethyl)vinyl]-1H-pyrazole-3-carbonitrile To a mixture of Preparation 82 (223 mg, 0.5 mmol) and Preparation 59 (212 mg, 1.0 mmol) was added, under nitrogen, a degassed solution of tetrakis(triphenylphosphine)palladium(0) (2 mol %, 23 mg) in toluene (10 ml) and methanol (2 ml). To this mixture was added aqueous sodium carbonate solution (1M, 2 ml) and the biphasic reaction mixture was heated under nitrogen, at 85° C., for 22 h. The reaction mixture was cooled, diluted with diethyl ether and the organic layer was separated. This was then washed with water (2×5 ml), dried (MgSO₄) and concentrated under a stream of nitrogen. The residue was purified using an Isolute$^{SM}$ cartridge (silica, 10 g) with gradient elution, cyclohexane:dichloromethane [3:2 to 1:1]. The appropriate fractions were combined and concentrated to give Preparation 60 (138 mg).

MS (ES): M/Z [MH+] 415.1; expected mass for C14H6Cl2F6N4+H is 415.0 ¹H-NMR (CDCl3): 3.90-3.98 (2H), 5.96-5.99 (1H), 6.25-6.28 (1H), 7.80-7.82 (2H)

Preparation 61 tributyl(1-fluorovinyl)stannane

To a solution of Preparation 83 (4.7 g, 19.4 mmol) in dry N,N-dimethylformamide (50 ml), under nitrogen, was added bis(tributyltin)oxide (6 ml, 11.7 mmol) and caesium fluoride (500 mg, 1.94 mmol). The reaction mixture was then stirred overnight at room temperature. The reaction mixture was diluted with water (100 ml) and extracted with a mixture of hexane and diethyl ether (3:1, 150 ml). The extracts were washed with water (2×50 ml) and saturated brine solution (50 ml), dried (MgSO₄) and concentrated in vacuo to give Preparation 61 (5.1 g) as a colourless oil.

¹H-NMR (CDCl3): 0.85-0.89 (9H), 0.91-1.06 (6H), 1.27-1.35 (7H), 1.40-1.63 (6H), 4.41-4.64 (1H), 5.14-5.43 (1H)

Similarly prepared to Preparation 31 were:

Preparation 62

N'-{3-cyano-1-[2,6-dichloro-4-(trifluoromethyl)phenyl]-4-iodo-1H-pyrazol-5-yl}-N,N-dimethylimidoformamide; from the compound of Preparation 82 (0.5 g, 1.12 mmol to give the title compound as a yellow crystalline solid.

MS (ES): M/Z [MH+] 502.1; expected mass for C14H9Cl2F3IN5+H is 501.9 ¹H-NMR (CDCl3): 2.78-2.82 (3H), 3.03-3.08 (3H), 7.67-7.71 (2H), 8.23-8.27 (1H)

Preparation 63

N'-{3-cyano-1-[2,6-dichloro-4-(difluoromethoxy)phenyl]-1H-pyrazol-5-yl}-N,N-dimethylimidoformamide; from the compound of Preparation 30 (3.1 g, 9.7 mmol) to give the title compound (3.5 g).

MS (ES): M/Z [MH+] 374.0; expected mass for C14H11Cl2F2N5O+H is 374.0 ¹H-NMR (CDCl3): 2.76-2.80 (3H), 2.99-3.03 (3H), 6.14-6.17 (1H), 6.35-6.72 (1H), 7.11-7.15 (1H), 7.21-7.24 (1H), 7.70-7.73 (1H)

Preparation 64

(3-cyano-1-[2,6-dichloro-4-(trifluoromethyl)phenyl]-5-{[(1E)-(dimethylamino)methylene]amino}-1H-pyrazol-4-yl)(iodo)zinc To a solution of Preparation 62 (5.02 g, 10.0 mmol) in tetrahydrofuran (24 ml), under nitrogen, was added Rieke® zinc (1.31 g, 20.0 mmol) as a slurry in tetrahydrofuran (26 ml). The reaction mixture was then stirred overnight at room temperature. The excess zinc metal was allowed to settle and the solution containing Preparation 64 (0.2 mol per liter) was used directly in the next stage.

Preparation 65

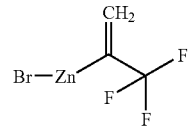

To a solution of Rieke® zinc (5% in tetrahydrofuran, 7.8 g, 157 ml, 120.0 mmol) in tetrahydrofuran (43 ml), under nitrogen, was added 2-bromo-3,3,3-trifluoroprop-1-ene (14.0 g, 80.0 mmol). The reaction mixture was stirred overnight and the solution of Preparation 65 used without further purification.

Similarly prepared to Preparation 31 was:

Preparation 66

N'-{3-cyano-1-[2,6-difluoro-4-(trifluoromethyl)phenyl]-4-iodo-1H-pyrazol-5-yl}-N,N-dimethylimidoformamide; from the compound of Preparation 84 (2.2 g, 5.3 mmol) to give the title compound (2.3 g).

¹H-NMR (CDCl3): 2.79-2.82 (3H), 3.03-3.06 (3H), 7.27-7.33 (2H), 8.22-8.25 (1H)

Similarly prepared to Preparation 39 were:

Preparation 67

N'-[3-cyano-1-[2,6-dichloro-4-pentafluorothiophenyl]-4-(difluoroacetyl)-1H-pyrazol-5-yl]-N,N-dimethylimidoformamide; from the compound of Preparation 58 (2.50 g, 4.47 mmol) isopropylmagnesium (1.72 g).

MS (ES): M/Z [MH+] 511.8; expected mass for C15H10Cl2F7N5OS+H is 512.0 ¹H-NMR (CDCl3): 2.81-2.83 (3H), 3.09-3.13 (3H), 6.41-6.69 (1H), 7.82-7.85 (2H), 8.51-8.54 (1H)

Preparation 68

N'-{4-[chloro(fluoro)acetyl]-3-cyano-1-[2,6-dichloro-4-(trifluoromethyl)phenyl]-1H-pyrazol-5-yl}-N,N-dimethylimidoformamide; from the compound of Preparation 62 (1.0 g, 1.99 mmol) isopropylmagnesium (800 mg).

MS (ES): M/Z [MH+] 470.0; expected mass for C16H10Cl3F4N5O+H is 470.0 ¹H-NMR (CDCl3): 2.79-2.84 (3H), 3.07-3.12 (3H), 7.20-7.24 (1H), 7.67-7.71 (2H), 8.45-8.48 (1H)

Preparation 69

5-Amino-1-(3-chloro-5-trifluoromethyl-pyridin-2-yl)-1H-pyrazole-3-carbonitrile may be prepared according to EP 500209.

Preparation 70

5-amino-1-{2,6-dichloro-4-[(trifluoromethyl)thio]phenyl}-1H-pyrazole-3-carbonitrile Sodium nitrite (224 mg, 3.25 mmol) was added carefully to sulphuric acid (concentrated, 1 ml), ensuring that the temperature did not rise above 30° C. After stirring at 15° C. for 1 h, acetic acid (2 ml) was added, followed by Preparation 36 (850 mg, 3.24 mmol) in acetic acid (3 ml). The reaction mixture was then heated at 50° C. for 1 h and cooled to room temperature. To a solution of Preparation 24 (500 mg, 3.29 mmol) in acetic acid (5 ml) was added ice water (5 ml), followed by the solution of the diazonium salt, added dropwise at 0° C. After complete addition, ammonium hydroxide (6 ml) was added and the reaction mixture was stirred overnight at room temperature.

The reaction mixture was filtered through Arbocel® and the filtrate was concentrated in vacuo. The residue was partitioned between dichloromethane and water and the organic phase was separated, dried ($Na_2SO_4$) and concentrated in vacuo to give Preparation 70 (1.0 g).

MS (ES): M/Z [MH+] 353.0; expected mass for $C_{11}H_5Cl_2F_3N_4S$+H is 353.0 $^1$H-NMR (CDCl3): 6.01-6.03 (1H), 7.75-7.78 (2H)

Preparation 71

N'-[3-cyano-1-[2,6-dichloro-4-(trifluoromethoxy)phenyl]-4-(trifluoroacetyl)-1H-pyrazol-5-yl]-N,N-dimethylimidoformamide To a solution of Preparation 87 (6.0 g, 15.3 mmol) in pyridine (75 ml) was added dropwise trifluoroacetic anhydride (4.32 ml, 6.4 g, 30.6 mmol). The reaction mixture was then stirred at room temperature, under nitrogen, overnight. The reaction mixture was concentrated in vacuo and the residue was purified by flash chromatography (silica), eluting with toluene. The appropriate fractions were combined and concentrated to give a mixture of protected and de-protected product. To the residue was added dichloromethane, followed by N,N-dimethylformamide dimethyl acetal (5 ml). The mixture was stirred overnight at room temperature and then concentrated in vacuo to give Preparation 71 (6.7 g).

MS (ES): M/Z [MH+] 488.0; expected mass for $C_{16}H_9Cl_2F_6N_5O_2$+H is 488.0 $^1$H-NMR (CDCl3): 2.80-2.84 (3H), 3.09-3.13 (3H), 7.30-7.33 (2H), 8.30-8.34 (1H)

Similarly prepared to Preparation 39 was:

Preparation 72

N'-[3-cyano-1-[2,6-dichloro-4-(trifluoromethoxy)phenyl]-4-(difluoroacetyl)-1H-pyrazol-5-yl]-N,N-dimethylimidoformamide; from the compound of Preparation 89 (6.20 g, 12.0 mmol) isopropylmagnesium (4.4 g).

MS (ES): M/Z [MH+] 470.0; expected mass for $C_{16}H_{10}Cl_2F_5N_5O_2$+H is 470.0 $^1$H-NMR (CDCl3): 2.79-2.83 (3H), 3.08-3.12 (3H), 6.41-6.69 (1H), 7.30-7.33 (2H), 8.46-8.49 (1H)

Preparation 73

N'-[3-cyano-1-[2,6-dichloro-4-(trifluoromethyl)phenyl]-4-(fluoroacetyl)-1H-pyrazol-5-yl]-N,N-dimethylimidoformamide To Preparation 91 (550 mg, 1.44 mmol) in dichloromethane (10 ml) was added N,N-dimethylformamide dimethyl acetal (190 mg, 1.59 mmol) and the reaction mixture was stirred at 35° C. for 1 h. The reaction mixture was concentrated in vacuo and the residue was passed through a silica plug, eluting with dichloromethane. The filtrate was concentrated in vacuo to give Preparation 73 (370 mg).

$^1$H-NMR (CDCl3): 2.77-2.79 (3H), 3.08-3.11 (3H), 5.43-5.46 (1H), 5.55-5.57 (1H), 7.67-7.70 (2H), 8.63-8.66 (1H)

Preparation 74

N'-[3-cyano-1-[2,6-dichloro-4-(trifluoromethyl)phenyl]-4-(1-hydroxy-1-methylethyl)-1H-pyrazol-5-yl]-N,N-dimethylimidoformamide To a solution of Preparation 62 (1.0 g, 2.0 mmol) in tetrahydrofuran (15 ml), at −30° C. and under nitrogen, was added dropwise isopropylmagnesium chloride (2M in tetrahydrofuran, 1.2 ml, 2.4 mmol). After stirring for 1 h, acetone (5 ml) was added via syringe and the reaction mixture was allowed to warm to room temperature. To the reaction mixture was added water (7 ml) and solid sodium carbonate (approximately 20 g). The mixture was stirred for 15 min, filtered and the residue was washed with dichloromethane. The organic phase was then separated, dried and concentrated in vacuo. The residue was passed through a silica plug, eluting with dichloromethane, followed by diethyl ether. The filtrate was concentrated in vacuo to give the title compound (280 mg).

MS (ES): M/Z [MH+] 434.0; expected mass for $C_{17}H_{16}Cl_2F_3N_5O$+H is 434.1 $^1$H-NMR (CDCl3): 1.65-1.69 (6H), 2.79-2.82 (3H), 2.85-2.88 (3H), 3.36-3.41 (1H), 7.40-7.42 (1H), 7.65-7.69 (2H)

Preparation 75

N'-[3-cyano-1-{2,6-dichloro-4-[(trifluoromethyl)thio]phenyl}-4-(trifluoroacetyl)-1H-pyrazol-5-yl]-N,N-dimethylimidoformamide To a solution of Preparation 92 (8.50 g, 20.8 mmol) in anhydrous pyridine (100 ml) was added dropwise trifluoroacetic anhydride (8.75 g, 41.6 mmol). The reaction mixture was then stirred overnight at room temperature. The reaction mixture was concentrated in vacuo and the residue was purified by flash chromatography (silica) with gradient elution, toluene:dichloromethane [1:0 to 1:1]. The appropriate fractions were combined and concentrated to give Preparation 75 (7.1 g).

MS (ES): M/Z [MH+] 504.0; expected mass for $C_{16}H_9Cl_2F_6N_5OS$+H is 504.0 $^1$H-NMR (CDCl3): 2.78-2.81 (3H), 3.09-3.12 (3H), 7.70-7.73 (2H), 8.34-8.37 (1H)

Similarly prepared to Preparation 31 was:

Preparation 76

N-[1-[3-chloro-5-(trifluoromethyl)pyridin-2-yl]-3-cyano-4-(trifluoroacetyl)-1H-pyrazol-5-yl]-N,N-dimethylimidoformamide; from the compound of Preparation 93 (5.98 g, 15.6 mmol) to give the title compound (6.3 g).

MS (ES): M/Z [MH+] 439.0; expected mass for C15H9ClF6N6O+H is 439.1 $^1$H-NMR (CDCl3): 2.83-2.86 (3H), 3.11-3.14 (3H), 8.13-8.15 (1H), 8.33-8.35 (1H), 8.76-8.79 (1H)

Similarly prepared to Preparation 39 was:

Preparation 77

N'-[3-cyano-1-[2,6-dichloro-4-(difluoromethoxy)phenyl]-4-(trifluoroacetyl)-1H-pyrazol-5-yl]-N,N-dimethylimidoformamide; from the compound of Preparation 94 (0.50 g, 1.0 mmol) to give the title compound (425 mg).

MS (ES): M/Z [MH+] 470.0; expected mass for C16H10Cl2F5N5O2+H is 470.0

Similarly prepared to Preparation 48 was:

Preparation 78

N'-{4-{1-[chloro(difluoro)methyl]vinyl}-3-cyano-1-[2,6-dichloro-4-(trifluoromethyl)phenyl]-1H-pyrazol-5-yl}-N,N-dimethylimidoformamide; from the compound of Preparation 96 (1.20 g, 2.5 mmol) to give the title compound (1.1 g).

MS (ES): M/Z [MH+] 485.9; expected mass for C17H11Cl3F5N5+H is 486.0 $^1$H-NMR (CDCl3): 2.72-2.75 (3H), 2.93-2.95 (3H), 5.76-5.78 (1H), 6.18-6.20 (1H), 7.66-7.68 (2H), 7.74-7.77 (1H)

Preparation 79

5-amino-1-[2,6-dichloro-4-(pentafluorothio)phenyl]-4-iodo-1H-pyrazole-3-carbonitrile To a solution of Preparation 95 (40.0 g, 106 mmol) in acetonitrile (400 ml) was added N-iodosuccinimide (26.4 g, 117 mmol) and the reaction mixture was stirred at room temperature overnight. The reaction mixture was diluted with ethyl acetate (1 l) and washed with aqueous sodium thiosulphate solution (10%, 3×500 ml) and brine (500 ml). The organic phase was dried (MgSO$_4$) and concentrated in vacuo to give Preparation 79 (53 g) as a brown solid.

$^1$H-NMR (CDCl3): 3.87-3.94 (2H), 7.88-7.90 (2H)

Preparation 80

5-Amino-4-(2-bromo-acetyl)-1-(2,6-dichloro-4-trifluoromethyl-phenyl)-1H-pyrazole-3-carbonitrile may be prepared according to U.S. Pat. No. 6,069,157 or EP846686

Similarly prepared to Preparation 79 was:

Preparation 81

5-Amino-1-(2,6-dichloro-4-trifluoromethoxy-phenyl)-4-iodo-1H-pyrazole-3-carbonitrile; from the compound of Preparation 88 (5.0 g, 14.8 mmol) to give the title compound (6.8 g).

MS (ES): M/Z [MH+] 462.8; expected mass for C11H4Cl2F3IN4O+H is 462.9

Preparation 82

5-amino-1-[2,6-dichloro-4-(trifluoromethyl)phenyl]-4-iodo-1H-pyrazole-3-carbonitrile may be prepared according to U.S. Pat. No. 6,069,157, EP933363, WO9828278

Preparation 83

(1-fluorovinyl)(methyl)diphenylsilane

To a solution of lithium wire (2.08 g, 300 mmol) in dry tetrahydrofuran (150 ml) was added methyldiphenylsilyl chloride (15.8 ml, 75 mmol) and a catalytic amount of iodine. The reaction mixture was sonicated for 40 min and then stirred overnight at room temperature. The reaction mixture was cooled to −78° C. and 1,1-difluoroethylene (approx. 225 mmol) was passed through the mixture for 30 min. The mixture was stirred at −78° C. for 2 h and then warmed to room temperature.

The reaction mixture was quenched with saturated ammonium chloride solution and extracted with cyclohexane (×2). The combined extracts were washed with brine, dried (MgSO$_4$) and concentrated in vacuo. The residue was purified by column chromatography (silica, 1 kg) eluting with hexane, followed by cyclohexane. The appropriate fractions were combined and concentrated to give Preparation 83 (7 g) as a colourless oil.

$^1$H-NMR (CDCl3): 0.76-0.81 (3H), 4.82-5.01 (1H), 5.48-5.60 (1H), 7.39-7.51 (6H), 7.61-7.71 (4H)

Similarly prepared to Preparation 79 was:

Preparation 84

5-Amino-1-(2,6-difluoro-4-trifluoromethyl-phenyl)-4-iodo-1H-pyrazole-3-carbonitrile; from the compound of Preparation 90 (2.00 g, 6.9 mmol) to give the title compound (2.2 g).

$^1$H-NMR (CDCl3): 3.89-4.04 (2H), 7.39-7.45 (2H)

Preparation 85

Difluoro-acetyl chloride

To difluoroacetic acid (6.0 g, 3.93 ml, 62.5 mmol) at −10° C., was added phosphorous pentachloride (14.3 g, 68.8 mmol). The reaction mixture was stirred at 0° C. for 10 min and then heated to 80° C.

The reaction mixture was distilled and the product fraction collected at −78° C. to give Preparation 85 (30 g) [bp 25-30° C.].

$^1$H-NMR (CDCl3): 5.76-6.07 (1H)

Preparation 86

Chlorofluoroacetyl chloride

To phosphorus pentachloride (10.2 g, 49.1 mmol) was added dropwise chlorofluoroacetic acid (5.0 g, 44.6 mmol) at 0° C.

The reaction mixture was allowed to warm to room temperature and distilled at ambient pressure (×2) to give Preparation 86 (5.0 g, b.p. 65° C.).

$^1$H-NMR (CDCl3): 6.29-6.44 (1H)

Similarly prepared to Preparation 31 was:

Preparation 87

N'-{3-cyano-1-[2,6-dichloro-4-(trifluoromethoxy)phenyl]-1H-pyrazol-5-yl}-N,N-dimethylimidoformamide; from the compound of Preparation 88 (7.0 g, 20.8 mmol) to give the title compound (6.2 g).

MS (ES): M/Z [MH+] 392.0; expected mass for C14H10Cl2F3N5O+H is 392.0 $^1$H-NMR (CDCl3): 2.77-2.82 (3H), 3.00-3.04 (3H), 6.15-6.17 (1H), 7.27-7.31 (2H), 7.70-7.75 (1H)

Preparation 88

5-Amino-1-(2,6-dichloro-4-trifluoromethoxy-phenyl)-1H-pyrazole-3-carbonitrile

To sulphuric acid (18M, 54 ml) was added sodium nitrite (13.9 g, 201.2 mmol) and the solution was stirred at 15° C. for 1 h. To the solution was added acetic acid (200 ml), followed by 2,6-dichloro-4-(trifluoromethoxy)aniline (45.0 g, 182.9 mmol) in acetic acid (90 ml), ensuring the temperature of the solution did not rise above 20° C. After addition was complete, the mixture was heated at 50° C. for 1 h, cooled to room temperature and added dropwise to a solution of Preparation 46 (27.8 g, 182.9 mmol) in acetic acid (115 ml) and ice cold water (145 ml). The reaction mixture was then stirred overnight at room temperature. To the reaction mixture was added dichloromethane (500 ml) and the mixture was stirred for 10 min. The two phases were separated and the organic phase was washed with water (200 ml) and ammonia (0.88, 400 ml) was added dropwise, maintaining the temperature of the mixture below 10° C. This mixture was stirred overnight at room temperature and the organic phase was separated and concentrated in vacuo.

The residue was re-crystallised from toluene/pentane [2:1] to give Preparation 88 (22.4 g).

MS (ES): M/Z [MH+] 337.0; expected mass for C11H5Cl2F3N4O+H is 337.0 $^1$H-NMR (CDCl3): 3.66-3.82 (2H), 5.99-6.01 (1H), 7.35-7.38 (2H)

Similarly prepared to Preparation 31 was:

Preparation 89

N'-{3-cyano-1-[2,6-dichloro-4-(trifluoromethoxy)phenyl]-4-iodo-1H-pyrazol-5-yl}-N,N-dimethylimidoformamide; from the compound of Preparation 81 (6.8 g, 14.7 mmol) to give the title compound (6.2 g).

$^1$H-NMR (CDCl3): 2.76-2.79 (3H), 3.01-3.04 (3H), 7.27-7.30 (2H), 8.17-8.20 (1H)

Preparation 90

5-Amino-1-(2,6-difluoro-4-trifluoromethyl-phenyl)-1H-pyrazole-3-carbonitrile

A solution of Preparation 56 (400 mg, 1.19 mmol) in phosphorus oxychloride (20 ml) was heated at reflux for 1 h. The reaction mixture was quenched by addition to water and the subsequent mixture was extracted with dichloromethane. The combined extracts were then dried (MgSO4) and concentrated in vacuo. The residue was purified by column chromatography (silica), eluting with dichloromethane. The appropriate fractions were combined and concentrated to give Preparation 90 (250 mg).

MS (ES): M/Z [MH+] 289.0; expected mass for C11H5F5N4+H is 289.1 $^1$H-NMR (CDCl3): 3.76-3.87 (2H), 6.02-6.04 (1H), 7.37-7.43 (2H)

Preparation 91

5-Amino-1-(2,6-dichloro-4-trifluoromethyl-phenyl)-4-(2-fluoro-acetyl)-1H-pyrazole-3-carbonitrile To a solution of Preparation 80 (800 mg, 1.80 mmol) in toluene (20 ml) was added 18-Crown-6 (85.6 mg, 3.24 μand potassium fluoride (anhydrous, 210 mg, 3.60 mmol) in toluene (20 ml). The reaction mixture was then heated at 90° C. for 2 days.

The reaction mixture was concentrated in vacuo and the residue was passed through a silica plug, eluting with diethyl ether. The filtrate was concentrated in vacuo to give Preparation 91 (500 mg).

MS (ES): M/Z [MH+] 380.9; expected mass for C13H6Cl2F4N4O+H is 381.0 $^1$H-NMR (CDCl3): 5.38-5.40 (1H), 5.50-5.52 (1H), 5.84-5.90 (2H), 7.79-7.81 (2H), Similarly prepared to Preparation 31 was:

Preparation 92

N'-(3-cyano-1-{2,6-dichloro-4-[(trifluoromethyl)thio]phenyl}-1H-pyrazol-5-yl)-N,N-dimethylimidoformamide; from the compound of Preparation 70 (1.0 g, 2.93 mmol) to give the title compound (720 mg).

MS (ES): M/Z [MH+] 408.0; expected mass for C14H10Cl2F3N5S+H is 408.0 $^1$H-NMR (CDCl3): 2.80-2.84 (3H), 3.01-3.06 (3H), 6.18-6.22 (1H), 7.68-7.70 (2H), 7.71-7.73 (1H)

Preparation 93

5-Amino-1-(3-chloro-5-trifluoromethyl-pyridin-2-yl)-4-(2,2,2-trifluoro-acetyl)-1H-pyrazole-3-carbonitrile To a solution of Preparation 69 (4.50 g, 15.6 mmol) in pyridine (45 ml), at 0° C., was added dropwise trifluoroacetic anhydride (8.8 ml, 62.6 mmol). The reaction mixture was then stirred at room temperature for 3 h.

The reaction mixture was concentrated in vacuo and to the residue was added tetrahydrofuran (20 ml) and hydrochloric acid (10%, 20 ml). The reaction mixture was then heated at reflux for 1.5 h.

To the reaction mixture was added ethyl acetate and the two layers were separated. The aqueous layer was extracted with ethyl acetate (3×30 ml) and the combined organic phases were washed with hydrochloric acid (10%, 2×30 ml) and aqueous sodium hydrogen carbonate solution (3×30 ml), dried (MgSO4) and concentrated in vacuo to give Preparation 93 (6.1 g).

MS (ES): M/Z [MH+] 383.9; expected mass for C12H4ClF6N5O+H is 384.0 $^1$H-NMR (CDCl3): 7.54-7.64 (2H), 8.24-8.27 (1H), 8.67-8.69 (1H)

Similarly prepared to Preparation 79 was:

Preparation 94

N'-{3-cyano-1-[2,6-dichloro-4-(difluoromethoxy)phenyl]-4-iodo-1H-pyrazol-5-yl}-N,N-dimethylimidoformamide; from the compound of Preparation 63 (2.44 g, 6.5 mmol) to give the title compound (3.1 g).

MS (ES): M/Z [MH+] 500.0; expected mass for C14H10Cl2F2IN5O+H is 499.9

Preparation 95

5-amino-1-[2,6-dichloro-4-(pentafluorothio)phenyl]-1H-pyrazole-3-carbonitrile may be prepared according to WO 9306089, EP605469.

Similarly prepared to Preparation 39 was:

Preparation 96

N'-{4-[chloro(difluoro)acetyl]-3-cyano-1-[2,6-dichloro-4-(trifluoromethyl)phenyl]-1H-pyrazol-5-yl}-N,N-dimethylimidoformamide; from the compound of Preparation 62 (5.0 g, 10.0 mmol) to give the title compound (2.9 g).

MS (ES): M/Z [MH+] 487.9; expected mass for C16H9C13F5N5O+H is 488.0 $^1$H-NMR (CDCl3): 2.80-2.83 (3H), 3.09-3.13 (3H), 7.68-7.71 (2H), 8.28-8.31 (1H)

Preparation 97

4-Trifluoromethylthio-aniline may be prepared according to EP 546391 A2

Preparation 98

5-Amino-1-(2,6-dichloro-4-trifluoromethyl-phenyl)-4-(1-Hydroxy-2,2,2-trifluoro-1-trifluoromethyl-ethyl)-1H-pyrazole-3-carbonitrile 5-amino-3-cyano-1-(2,6-dichloro-4-trifluoromethylphenyl)pyrazole, see EP295117, (15 g, 46 mmol, 1 eq) was solubilised in hexafluoroacetone sesquihydrate and the reaction mixture was heated at 100° C. After 2 hours, a LC-MS showed completion (single peak [487]). After cooling to RT, ethyl acetate (500 ml) was added, and the whole crude was washed with water (50 ml) then brine (2×50 ml), then dried over magnesium sulphate, filtered and concentrated under vacuuo, yielding the title compound as a brown solid, containing traces of solvent (22 g), that is used as such in the next step.

Preparation 99

N'-[4-(1-Hydroxy-2,2,2-trifluoro-1-trifluoromethyl-ethyl)-5-cyano-2-(2,6-dichloro-4-trifluoromethyl-phenyl)-2H-pyrazol-3-yl]-N,N-dimethyl-formamidine The compound of Preparation 98 (22 g crude from above, estimate 46 mmol, 1 eq) is suspended in dichloromethane (DCM) under nitrogen. Dimethoxyacetal dimethylformamide (99+, 7 g, 8 ml, 56 mmol, 1.2 eq) is then added slowly to the reaction mixture (over 1 min.). The reaction mixture is heated to 40° C. and is left stirring for one hour. The crude mixture is then concentrated under vacuuo and diluted with ether (600 ml), then washed with water (2×50 ml) and dried over powdered MgSO$_4$, filtered and concentrated under vacuuo, leading to the titled compound as brown solid (20.5 g).

Preparation 100

N'-[4-(1-Chloro-2,2,2-trifluoro-1-trifluoromethyl-ethyl)-5-cyano-2-(2,6-dichloro-4-trifluoromethyl-phenyl)-2H-pyrazol-3-yl]-N,N-dimethyl-formamidine The compound of Preparation 99 (20.5 g, 37 mmol, 1 eq) was solubilised in anhydrous acetonitrile and thionyl chloride was added slowly via syringe (44 g, 27 ml, 370 mmol, 10 eq). The reaction mixture was heated to 85° C. for two hours to completion; 200 ml of cylcohexane were then added to the cooled mixture and the pale yellow powder was filtered off (9 g). The remaining crude was then adsorbed onto silica, dried out and eluted on a pad of silica with dichloromethane. The desired fractions were combined and concentrated to afford a pale yellow oil that solidified on standing (11 g) to give a combined yield of the titled compound of 20 g.

LCMS [561]

Preparation 101

N'-[5-Cyano-2-(2,6-dichloro-4-trifluoromethyl-phenyl)-4-(2,2-difluoro-1-trifluoromethyl-vinyl)-2H-pyrazol-3-yl]-N,N-dimethyl-formamidine The compound of Preparation 100 (20 g, 35 mmol) was dissolved in 500 ml of anhydrous THF and 150 ml of a 5 g/100 ml suspension of Rieke Zinc (7.5 g, 110 mmol, 3eq) was added. After 3 hours, LCMS shows quantitative conversion to the perfluoroisopropenyl compound (single peak [506]). The crude mixture was filtered through a pad of celite and then adsorbed onto silica. The silica pad was then eluted with toluene yielding the titled compound as a white solid (16 g)

Preparation 102

N'-[5-Cyano-2-(2,6-dichloro-4-trifluoromethyl-phenyl)-4-(2,2-difluoro-1-trifluoromethyl-cyclopropyl)-2H-pyrazol-3-yl]-N,N-dimethyl-formamidine Diazomethane is generated using the Aldrich diazald kit (procedure AL-180) on 15 grams of diazald. The freshly prepared solution of diazomethane is mixed with the compound of Preparation 101 (16 g, 31 mmol, solubilised in anhydrous THF) and the resulting yellow solution is left standing for 2 hours at RT. A LC-MS shows complete conversion (91% of titled compound [520], 5% of a by-product assumed to be the corresponding pyrazoline [548], and 4% of an unknown by-product). After concentration under vacuuo, the resulting yellow solid (17 g) was used without further purification in the next step.

What is claimed is:

1. A combination product comprising a compound of formula (I):

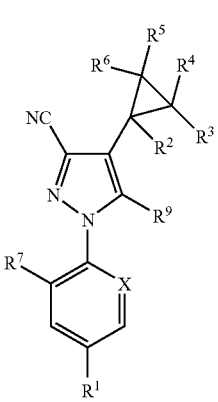

(I)

wherein:
R$^1$ is CF$_3$, OCF$_2$H, OCF$_3$, —SCF$_3$, —SOCF$_3$, —SO$_2$CF$_3$, or SF$_5$;
R$^2$ is H, fluoro, or C$_{1-4}$ alkyl optionally substituted by 1 to 5 halogen atoms independently selected from chloro and fluoro;
R$^3$, R$^4$, R$^5$, and R$^6$ are independently selected from H, Cl, F, or C$_{1-4}$ alkyl optionally substituted by 1 to 5 halogen groups independently selected from chloro and fluoro;
R$^7$ is Cl or fluoro;
X is CR$^8$ where R$^8$ is Cl or fluoro; and
R$^9$ is NR$^a$R$^b$;

R$^a$ is selected from hydrogen, C$_{1-6}$ alkyl, C$_{2-6}$ alkenyl, C$_{3-8}$ cycloalkyl, C(O)OC$_{1-6}$ alkyl and C$_{1-6}$ alkanoyl, wherein each of the above groups may include one or more optional substituents where chemically possible independently selected from halo, phenyl, hydroxy, —C(O)OH, —C(O)O C$_{1-6}$ alkyl, C$_{1-6}$ alkyl, C$_{1-6}$ haloalkyl, C$_{3-8}$ cycloalkyl, C$_{1-6}$ alkoxy, C$_{1-6}$ haloalkoxy, amino, C$_{1-6}$ alkyl amino and di C$_{1-6}$ alkyl amino;

R$^b$ is selected from hydrogen, C$_{1-6}$ alkyl, C$_{2-6}$ alkenyl, C$_{1-6}$ alkanoyl and C(O)OC$_{1-6}$ alkyl, wherein each of the above groups may include one or more optional substituents where chemically possible independently selected from, halo, phenyl, hydroxy, —COOH, —C(O)O C$_{1-6}$ alkyl, C$_{1-6}$ alkyl, C$_{1-6}$ haloalkyl, C$_{3-8}$ cycloalkyl, C$_{1-6}$ alkoxy, C$_{1-6}$ haloalkoxy, amino, C$_{1-6}$ alkyl amino and di C$_{1-6}$ alkyl amino;

or a pharmaceutically acceptable salt or prodrug thereof; with the proviso that at least one of R$^2$, R$^3$, R$^4$, R$^5$, or R$^6$ is fluoro, with one or more other biologically active compounds.

2. The combination of claim 1, wherein R$^1$ is CF$_3$ or SF$_5$.

3. The combination of claim 1, wherein R$^2$ is F, CF$_3$ or CHF$_2$.

4. The combination of claim 1, wherein R$^3$ and R$^4$ both represent fluoro and R$^5$ and R$^6$ represent hydrogen.

5. The combination of claim 1, wherein R$^2$ is CF$_3$, R$^3$ and R$^4$ both represent fluoro and R$^5$ and R$^6$ represent hydrogen.

6. The combination of claim 1, wherein X is CR$^8$ and R$^7$ and R$^8$ are both chloro.

7. The combination of claim 1, wherein R$^9$ is selected from NH$_2$, C$_{1-6}$ alkoxycarbonylamino, with optional substitution on the alkyl group by one or more fluoro groups, di-C$_{1-6}$ alkylamino and het, C$_{1-6}$ alkylamino, with optional substitution on the alkyl group by one or more fluoro groups, C$_{3-8}$ cycloalkyl, phenyl and het.

8. The combination of claim 1, wherein R$^9$ is NH$_2$.

9. The combination of claim 1, wherein the compound of formula (I) is selected from:

5-amino-1-[2,6-dichloro-4-pentafluorothiophenyl]-4-[2,2-difluoro-1-(trifluoromethyl)cyclopropyl]-1H-pyrazole-3-carbonitrile;

5-amino-1-[2,6-dichloro-4-(trifluoromethyl)phenyl]-4-[2,2-difluoro-1-(trifluoromethyl)cyclopropyl]-1H-pyrazole-3-carbonitrile;

5-amino-1-[2,6-dichloro-4-(trifluoromethyl)phenyl]-4-(1,2,2-trifluorocyclopropyl)-1H-pyrazole-3-carbonitrile;

5-amino-1-[2,6-dichloro-4-(trifluoromethyl)phenyl]-4-(pentafluorocyclopropyl)-1H-pyrazole-3-carbonitrile;

5-amino-4-(2,2-dichloro-1-fluorocyclopropyl)-1-[2,6-dichloro-4-(trifluoromethyl)phenyl]-1H-pyrazole-3-carbonitrile;

5-amino-1-[2,6-dichloro-4-pentafluorothiophenyl]-4-(pentafluorocyclopropyl)-1H-pyrazole-3-carbonitrile;

5-amino-1-[2,6-dichloro-4-pentafluorothiophenyl]-4-(1,2,2-trifluorocyclopropyl)-1H-pyrazole-3-carbonitrile;

5-amino-1-[2,6-dichloro-4-(trifluoromethyl)phenyl]-4-[1-(difluoromethyl)-2,2-difluorocyclopropyl]-1H-pyrazole-3-carbonitrile;

5-amino-1-[2,6-dichloro-4-(trifluoromethyl)phenyl]-4-(2,2-difluorocyclopropyl)-1H-pyrazole-3-carbonitrile;

5-amino-4-[2,2-difluoro-1-(trifluoromethyl)cyclopropyl]-1-[2,6-difluoro-4-(trifluoromethyl)phenyl]-1H-pyrazole-3-carbonitrile;

5-amino-1-[2,6-dichloro-4-pentafluorothiophenyl]-4-[1-(difluoromethyl)-2,2-difluorocyclopropyl]-1H-pyrazole-3-carbonitrile;

5-amino-4-{1-[chloro(fluoro)methyl]-2,2-difluorocyclopropyl}-1-[2,6-dichloro-4-(trifluoromethyl)phenyl]-1H-pyrazole-3-carbonitrile;

5-amino-1-[2,6-dichloro-4-(trifluoromethyl)phenyl]-4-[1-(difluoromethyl)-2,2,3,3-tetrafluorocyclopropyl]-1H-pyrazole-3-carbonitrile;

5-amino-1-[2,6-dichloro-4-(trifluoromethyl)phenyl]-4-[2,2,3,3-tetrafluoro-1-(trifluoromethyl)cyclopropyl]-1H-pyrazole-3-carbonitrile;

1-[2,6-dichloro-4-(trifluoromethyl)phenyl]-4-[2,2-difluoro-1-(trifluoromethyl)cyclopropyl]-5-(methylamino)-1H-pyrazole-3-carbonitrile;

5-amino-1-[2,6-dichloro-4-(trifluoromethoxy)phenyl]-4-[2,2-difluoro-1-(trifluoromethyl)cyclopropyl]-1H-pyrazole-3-carbonitrile;

5-amino-1-[2,6-dichloro-4-(trifluoromethoxy)phenyl]-4-[1-(difluoromethyl)-2,2,3,3-tetrafluorocyclopropyl]-1H-pyrazole-3-carbonitrile;

5-amino-1-[2,6-dichloro-4-(trifluoromethoxy)phenyl]-4-[1-(difluoromethyl)-2,2-difluorocyclopropyl]-1H-pyrazole-3-carbonitrile;

5-amino-1-[2,6-dichloro-4-(trifluoromethyl)phenyl]-4-[2,2-difluoro-1-(fluoromethyl)cyclopropyl]-1H-pyrazole-3-carbonitrile;

5-amino-1-[2,6-dichloro-4-(trifluoromethyl)phenyl]-4-(2,2-difluoro-1-methylcyclopropyl)-1H-pyrazole-3-carbonitrile;

5-amino-1-{2,6-dichloro-4-[(trifluoromethyl)thio]phenyl}-4-[2,2-difluoro-1-(trifluoromethyl)cyclopropyl]-1H-pyrazole-3-carbonitrile;

ethyl 3-cyano-1-[2,6-dichloro-4-(trifluoromethyl)phenyl]-4-[2,2-difluoro-1-(trifluoromethyl)cyclopropyl]-1H-pyrazol-5-ylcarbamate;

1-[2,6-dichloro-4-(trifluoromethyl)phenyl]-4-[2,2-difluoro-1-(trifluoromethyl)cyclopropyl]-5-(2-oxo-1,3-oxazolidin-3-yl)-1H-pyrazole-3-carbonitrile;

2-(dimethylamino)ethyl 3-cyano-1-[2,6-dichloro-4-(trifluoromethyl)phenyl]-4-[2,2-difluoro-1-(trifluoromethyl)cyclopropyl]-1H-pyrazol-5-ylcarbamate;

2,2,2-trifluoroethyl 3-cyano-1-[2,6-dichloro-4-(trifluoromethyl)phenyl]-4-[2,2-difluoro-1-(trifluoromethyl)cyclopropyl]-1H-pyrazol-5-ylcarbamate;

5-amino-1-{2,6-dichloro-4-[(trifluoromethyl)sulfonyl]phenyl}-4-[2,2-difluoro-1-(trifluoromethyl)cyclopropyl]-1H-pyrazole-3-carbonitrile;

5-amino-1-[2,6-dichloro-4-(difluoromethoxy)phenyl]-4-[2,2-difluoro-1-(trifluoromethyl)cyclopropyl]-1H-pyrazole-3-carbonitrile;

5-amino-1-[2,6-dichloro-4-pentafluorothiophenyl]-4-[1-(difluoromethyl)-2,2,3,3-tetrafluorocyclopropyl]-1H-pyrazole-3-carbonitrile;

Isopropyl 3-cyano-1-[2,6-dichloro-4-(trifluoromethyl)phenyl]-4-[2,2-difluoro-1-(trifluoromethyl)cyclopropyl]-1H-pyrazol-5-ylcarbamate; and 5-amino-4-{1-[chloro(difluoro)methyl]-2,2-difluorocyclopropyl}-1-[2,6-dichloro-4-(trifluoromethyl)phenyl]-1H-pyrazole-3-carbonitrile, or a pharmaceutically acceptable salt thereof.

10. The combination of claim 1, wherein the combination comprises a compound of formula (I), or a pharmaceutically acceptable salt thereof, and one or more other anti-parasitic agents.

11. The combination of claim 10, wherein the one or more other anti-parasitic agents are selected from ivermectin, avermectin, abamectin, emamectin, eprinomectin, doramectin, selamectin, moxidectin, nemadectin, albendazole, cambendazole, fenbendazole, flubendazole, mebendazole, oxfendazole, oxibendazole, parbendazole, tetramisole, levamisole, pyrantel pamoate, oxantel, morantel, triclabendazole, praziquantel, epsiprantel, fipronil, lufenuron, ecdysone, tebufenozide and imidacloprid.

12. A pharmaceutical composition comprising a compound of formula (I) of claim 1, or a pharmaceutically acceptable salt thereof, one or more further biologically active compounds, and a pharmaceutically suitable excipient.

13. A compound of claim 1 which is 5-amino-1-[2,6-dichloro-4-(trifluoromethyl)phenyl]-4-[2,2-difluoro-1-(trifluoromethyl)cyclopropyl]-1H-pyrazole-3-carbonitrile, or a pharmaceutically acceptable salt thereof.

14. A compound of claim 1 which is 5-amino-1-[2,6-dichloro-4-(trifluoromethyl)phenyl]4-(1,2,2-trifluorocyclopropyl)-1H-pyrazole-3-carbonitrile, or a pharmaceutically acceptable salt thereof.

15. A compound of claim 1 which is 5-amino-1-[2,6-dichloro-4-pentafluorothiophenyl]-4-[2,2-difluoro-1-(trifluoromethyl)cyclopropyl]-1H-pyrazole-3-carbonitrile, or a pharmaceutically acceptable salt thereof.

16. A compound of claim 1 which is 5-amino-1-[2,6-dichloro-4-(trifluoromethyl)phenyl]-4-(pentafluorocyclopropyl)-1H-pyrazole-3-carbonitrile, or a pharmaceutically acceptable salt thereof.

* * * * *